(12) United States Patent
Nachmias et al.

(10) Patent No.: US 10,595,854 B2
(45) Date of Patent: Mar. 24, 2020

(54) SURGICAL CUTTING DEVICE

(71) Applicant: T.A.G. Medical Devices—Agriculture Cooperative Ltd., Kibbutz Gaaton (IL)

(72) Inventors: Shai Nachmias, Nahariya (IL); Ran Weisman, Kfar-Vradim (IL); Aryeh Mirochinik, Kiryat Yam (IL)

(73) Assignee: T.A.G. Medical Devices—Agriculture Cooperative Ltd., Kibbutz Gaaton (IL)

( * ) Notice: Subject to any disclaimer, the term of this patent is extended or adjusted under 35 U.S.C. 154(b) by 216 days.

(21) Appl. No.: 15/751,867

(22) PCT Filed: Aug. 11, 2016

(86) PCT No.: PCT/IL2016/050881
§ 371 (c)(1),
(2) Date: Feb. 11, 2018

(87) PCT Pub. No.: WO2017/025971
PCT Pub. Date: Feb. 16, 2017

(65) Prior Publication Data
US 2018/0235600 A1    Aug. 23, 2018

Related U.S. Application Data

(60) Provisional application No. 62/203,741, filed on Aug. 11, 2015.

(51) Int. Cl.
A61B 17/04    (2006.01)
A61B 17/00    (2006.01)

(52) U.S. Cl.
CPC ............... A61B 17/0467 (2013.01); *A61B 2017/00367* (2013.01); *A61B 2017/00477* (2013.01); *A61B 2017/0474* (2013.01)

(58) Field of Classification Search
CPC ........ A61B 17/0467; A61B 2017/0474; A61B 2017/00477; A61B 2017/00367
See application file for complete search history.

(56) References Cited

U.S. PATENT DOCUMENTS 3,372,477 A * 3/1968 Hoppe ............... A61B 17/0467
606/138
3,802,074 A * 4/1974 Hoppe ............... A61B 17/0467
30/134

(Continued)

FOREIGN PATENT DOCUMENTS

| EP | 2415404 | 2/2012 |
|---|---|---|
| WO | WO 03/059174 | 7/2003 |
| WO | WO 2017/025971 | 2/2017 |

OTHER PUBLICATIONS

International Preliminary Report on Patentability dated Feb. 22, 2018 From the International Bureau of WIPO Re. Application No. PCT/IL2016/050881. (12 Pages).

(Continued)

*Primary Examiner* — Julian W Woo

(57) ABSTRACT

A device for suture thread cutting, containing:
a handle;
a stationary external element having a channel at the distal end, and a proximal end connected to said handle, said channel is fitted and shaped for holding a suture thread;
a movable cutter having a cutting edge, partially inserted into said handle, said cutting edge is configured to move between a first position and a second position in said channel;
wherein in said first position the suture thread is retained within the channel and in said second position the suture thread is cut.

14 Claims, 59 Drawing Sheets

(56) References Cited

U.S. PATENT DOCUMENTS

| | | | | |
|---|---|---|---|---|
| 3,995,619 A * | 12/1976 | Glatzer | A61B | 10/0275 |
| | | | | 600/550 |
| 5,423,837 A * | 6/1995 | Mericle | A61B | 17/0469 |
| | | | | 289/17 |
| 6,254,620 B1 * | 7/2001 | Koh | A61B | 17/0467 |
| | | | | 30/278 |
| 7,699,856 B2 * | 4/2010 | Van Wyk | A61B | 17/0467 |
| | | | | 606/138 |
| 7,879,055 B1 * | 2/2011 | Stone | A61B | 17/0467 |
| | | | | 606/170 |
| 7,905,892 B2 | 3/2011 | Nobles et al. | | |
| 7,992,571 B2 * | 8/2011 | Gross | A61B | 17/0485 |
| | | | | 128/898 |
| 8,252,005 B2 * | 8/2012 | Findlay, III | A61B | 17/0467 |
| | | | | 606/139 |
| 8,282,659 B2 * | 10/2012 | Oren | A61B | 17/0467 |
| | | | | 606/148 |
| 8,465,512 B2 | 6/2013 | Rosenhan | | |
| 8,568,428 B2 | 10/2013 | McClurg et al. | | |
| 8,585,720 B2 * | 11/2013 | Gross | A61B | 17/0467 |
| | | | | 606/148 |
| 8,597,307 B2 * | 12/2013 | Miller | A61B | 17/0467 |
| | | | | 606/138 |
| 8,777,968 B2 * | 7/2014 | Evans | A61B | 17/0467 |
| | | | | 606/139 |
| 8,834,497 B2 * | 9/2014 | Snell | A61B | 17/0467 |
| | | | | 606/148 |
| 8,911,457 B2 * | 12/2014 | Koogle, Jr. | A61B | 17/0467 |
| | | | | 606/148 |
| 8,911,461 B2 * | 12/2014 | Traynor | A61B | 17/0467 |
| | | | | 606/139 |
| 9,247,935 B2 * | 2/2016 | George | A61B | 17/0469 |
| 2003/0181926 A1 | 9/2003 | Dana et al. | | |
| 2004/0254598 A1 * | 12/2004 | Schumacher | A61B | 17/0467 |
| | | | | 606/170 |
| 2005/0234481 A1 | 10/2005 | Waller | | |
| 2010/0049213 A1 * | 2/2010 | Serina | A61B | 17/0467 |
| | | | | 606/139 |
| 2010/0324597 A1 | 12/2010 | Shikman | | |
| 2012/0158045 A1 | 6/2012 | Pipenhagen | | |

OTHER PUBLICATIONS

Invitation Pursuant to Rule 137(4) EPC and Article 94(3) EPC dated Sep. 10, 2018 From the European Patent Office Re. Application No. 16757086.0. (2 Pages).

Communication Relating to the Results of the Partial International Search dated Nov. 16, 2016 From the International Searching Authority Re. Application No. PCT/IL2016/050881. (8 Pages).

International Search Report and the Written Opinion dated Jan. 19, 2017 From the International Searching Authority Re. Application No. PCT/IL2016/050881. (8 Pages).

Communication Pursuant to Article 94(3) EPC dated Jan. 15, 2019 From the European Patent Office Re. Application No. 16757086.0. (4 Pages).

* cited by examiner

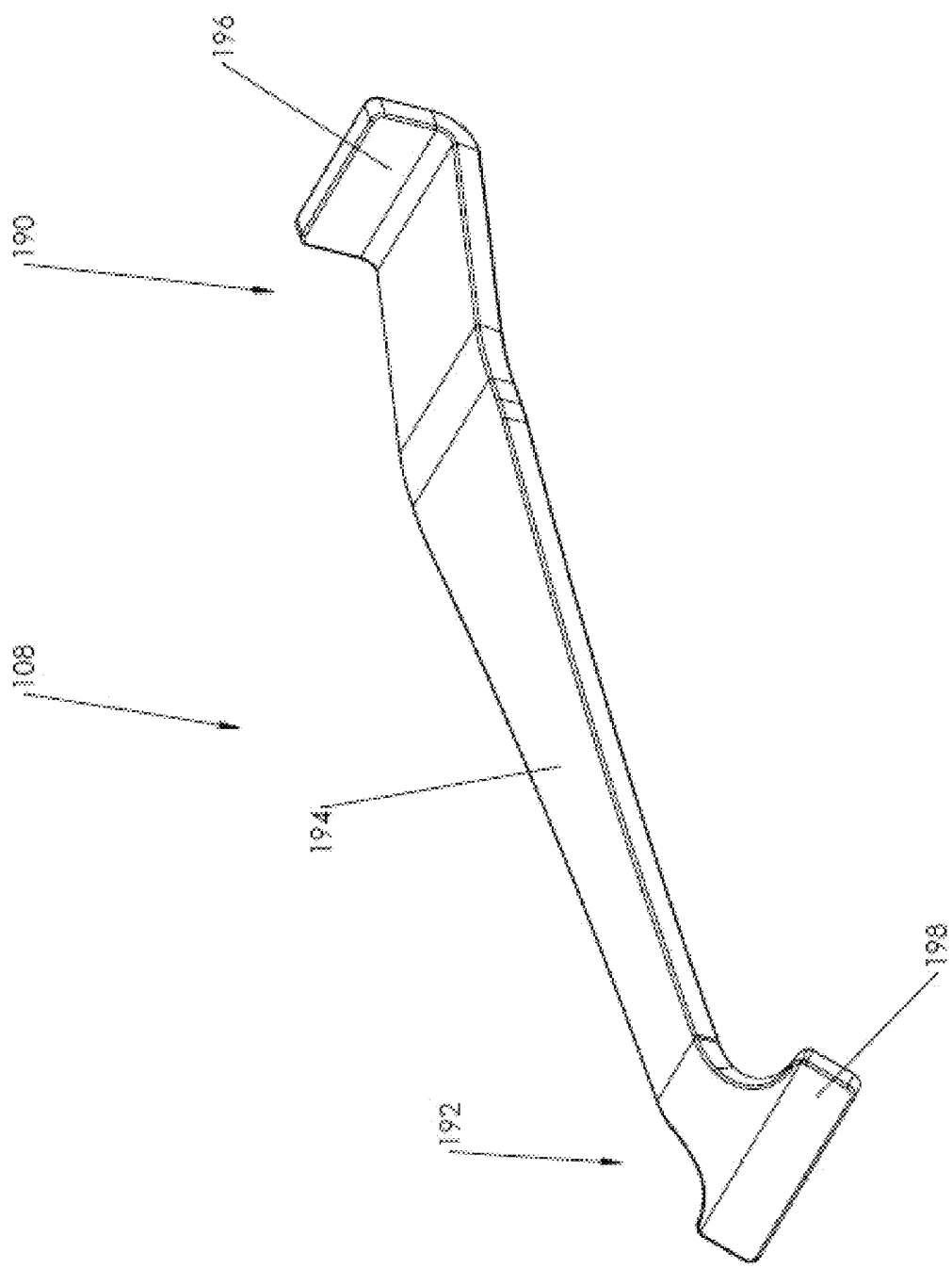

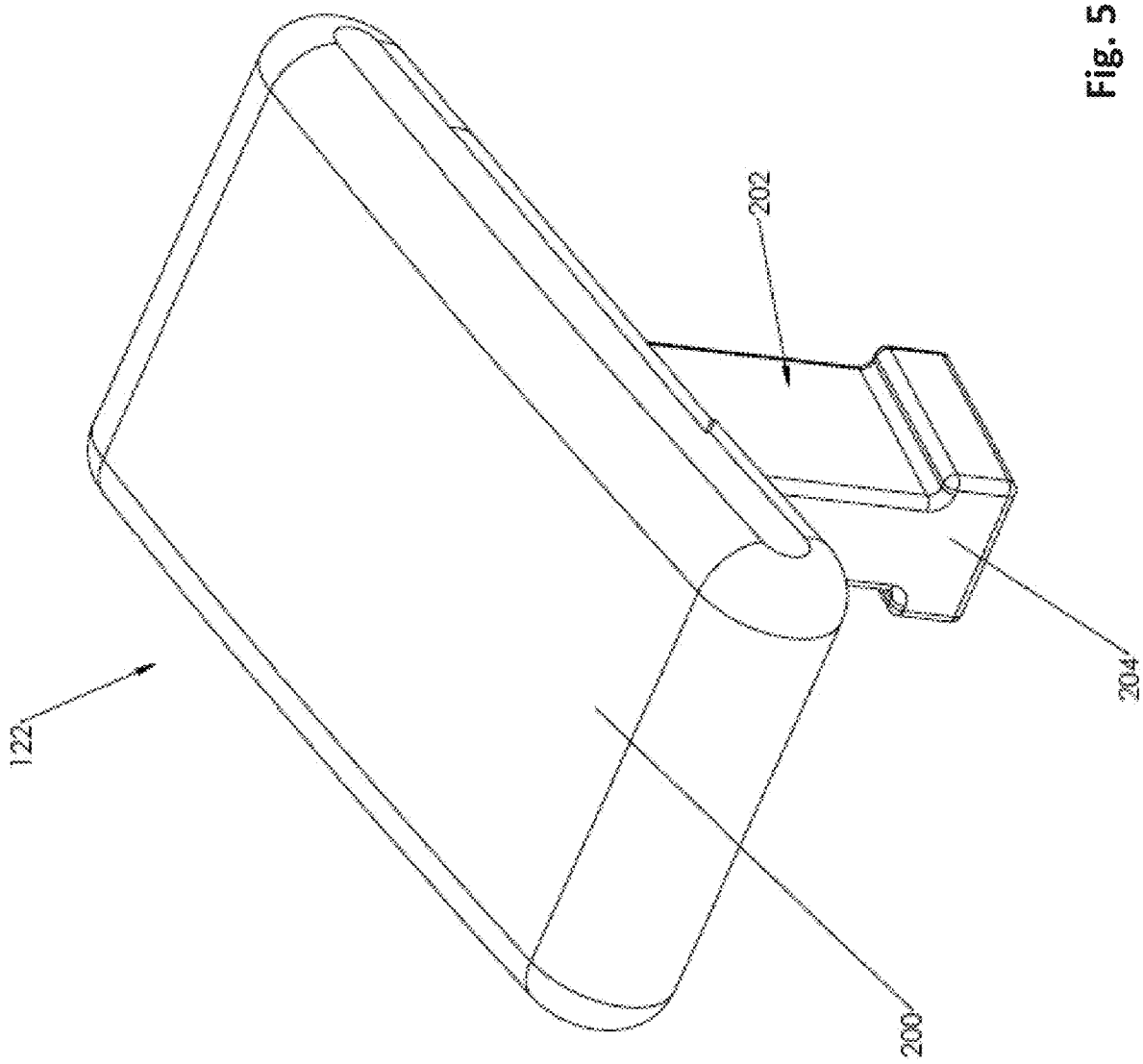

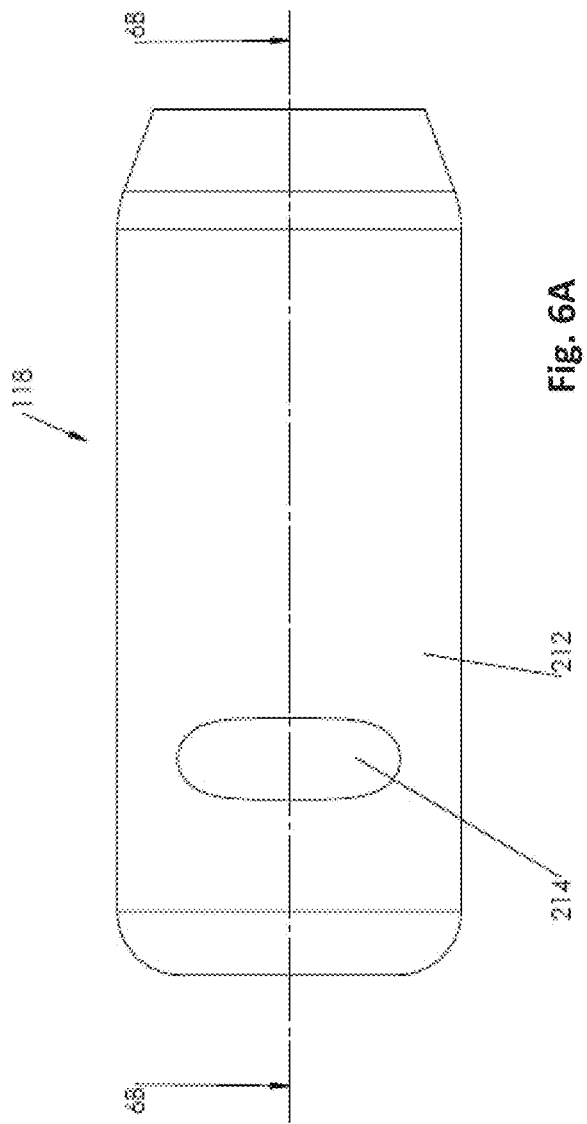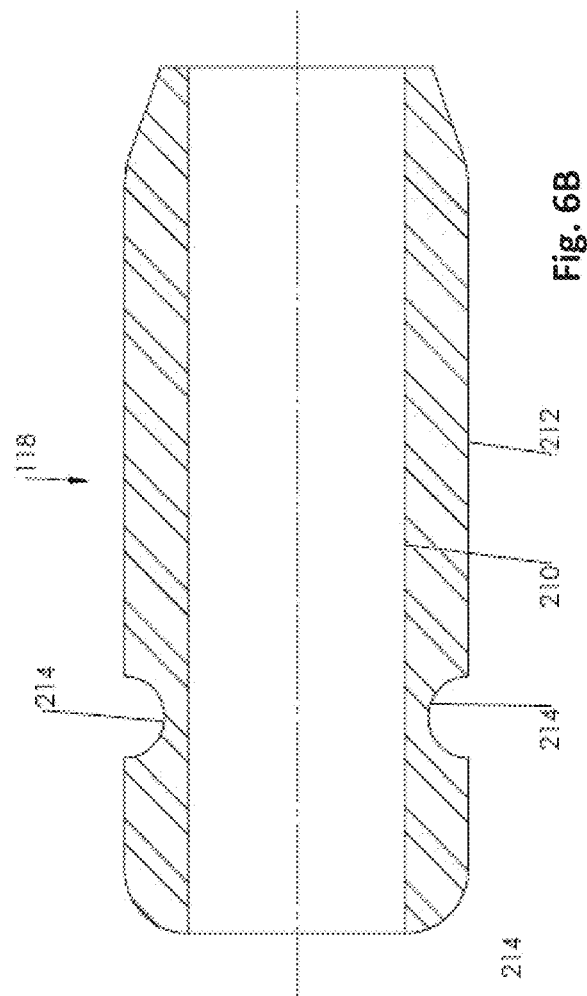

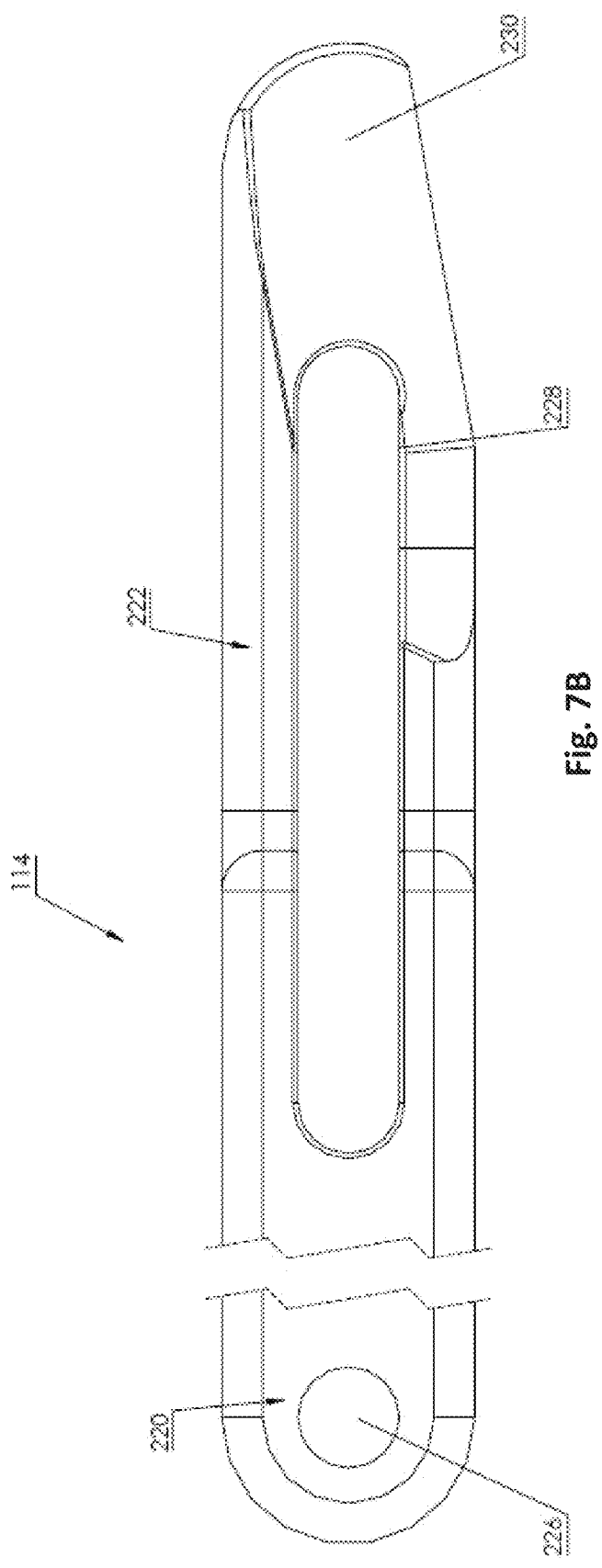
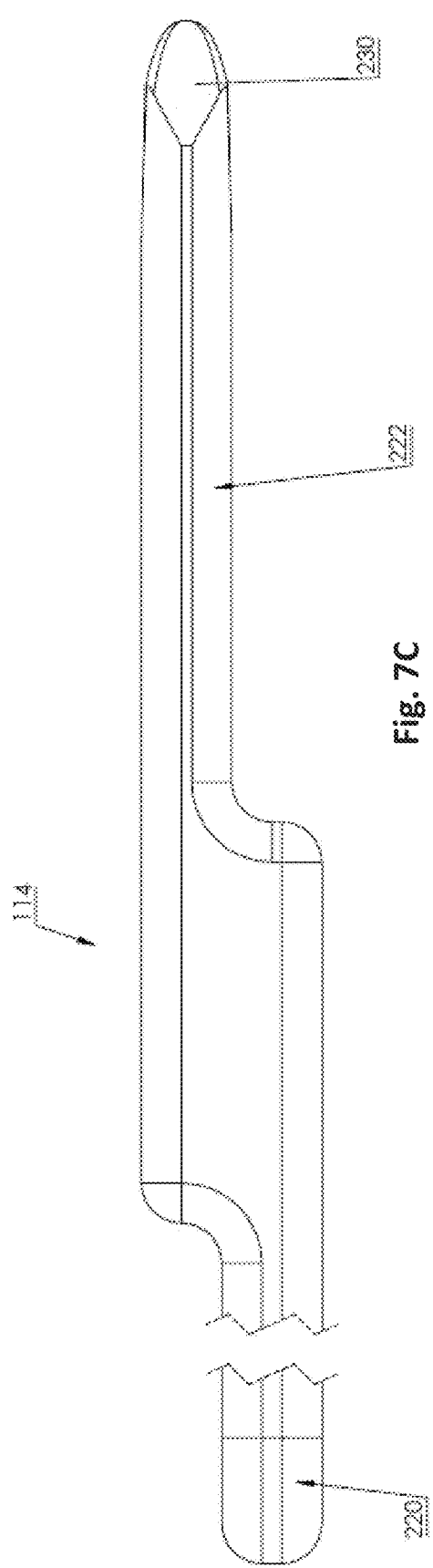
Fig. 7B
Fig. 7C

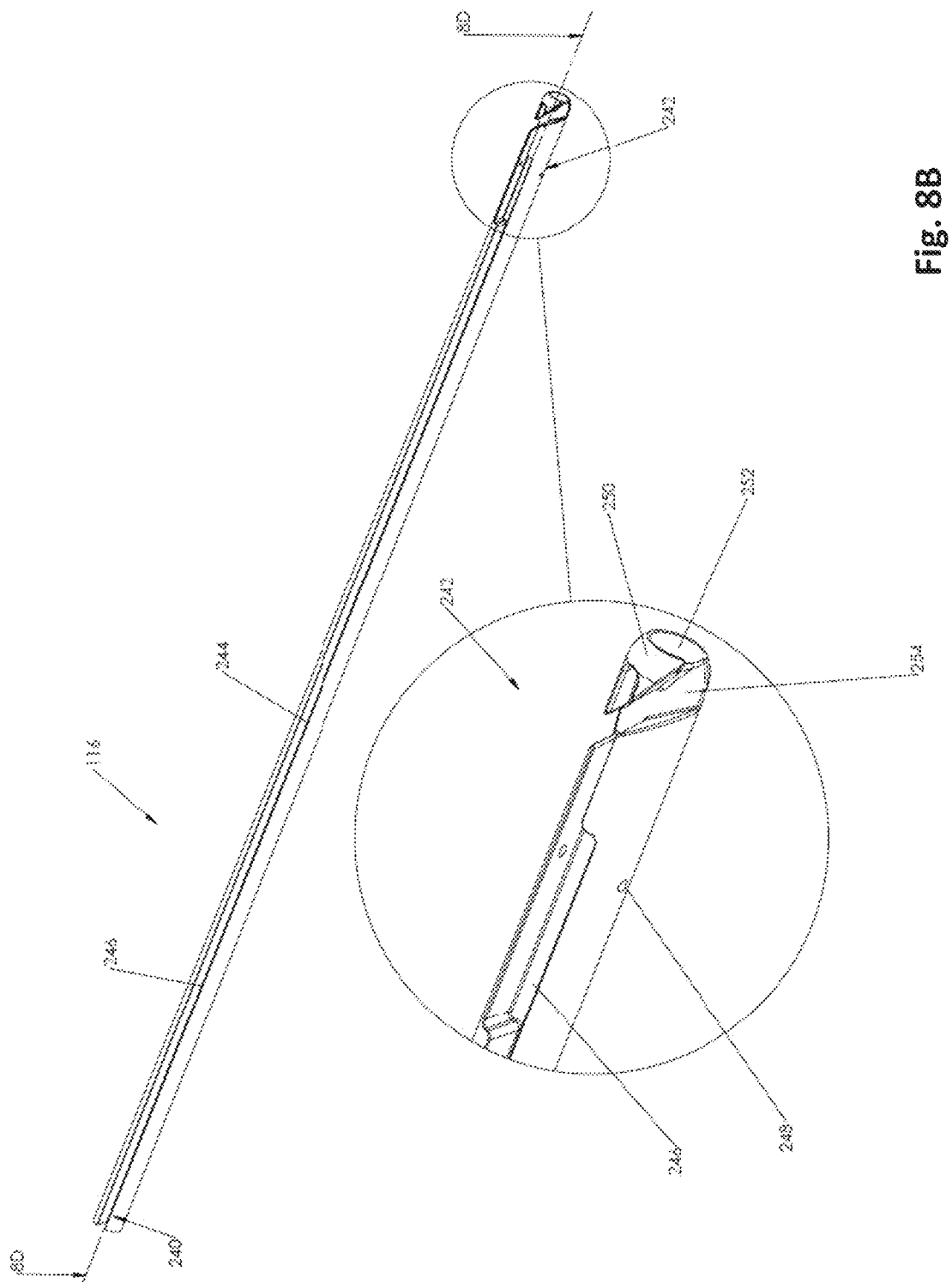

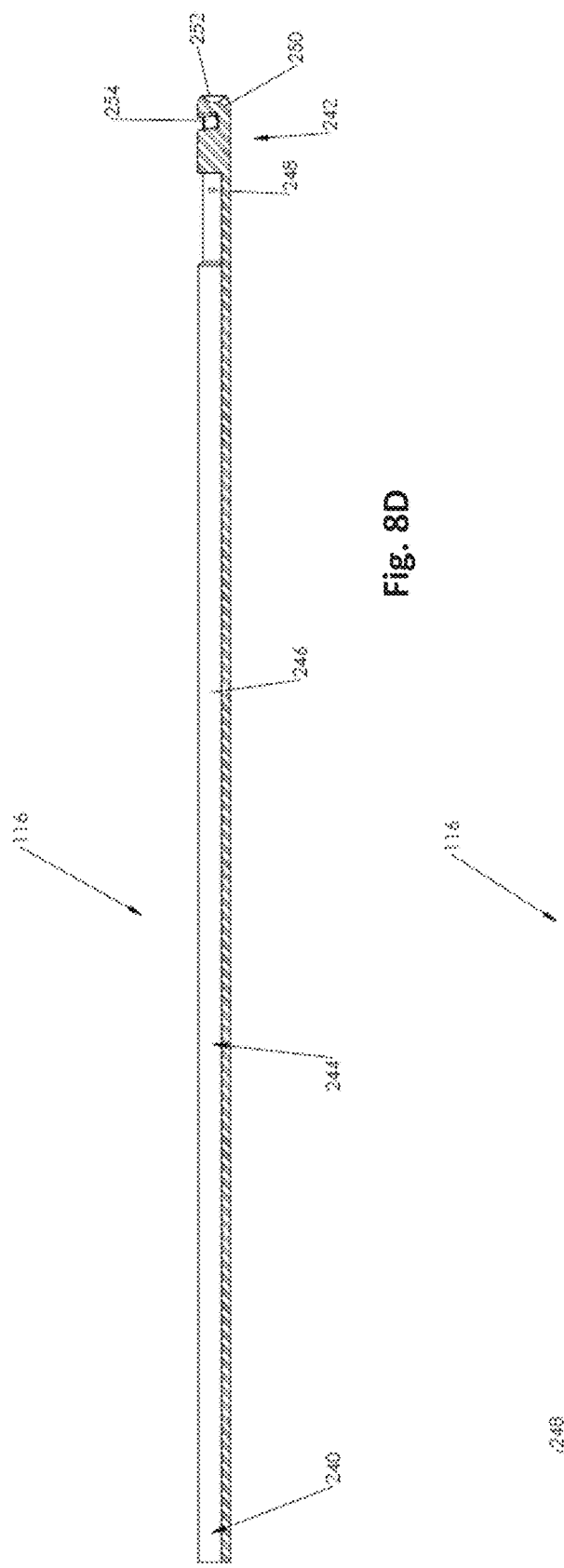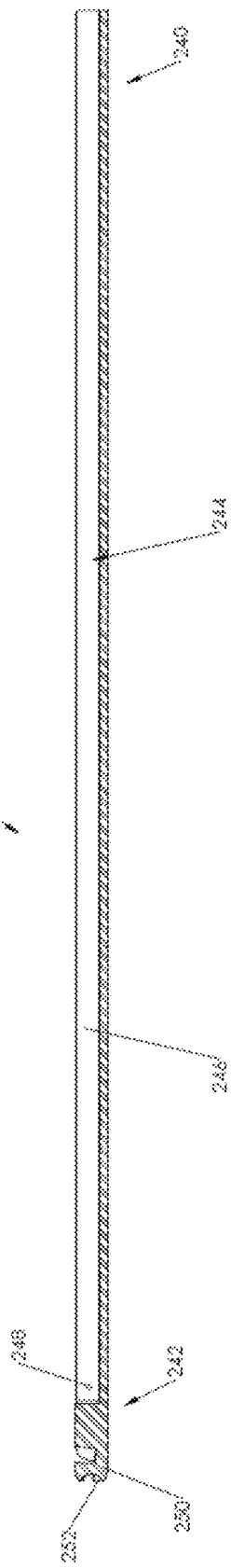

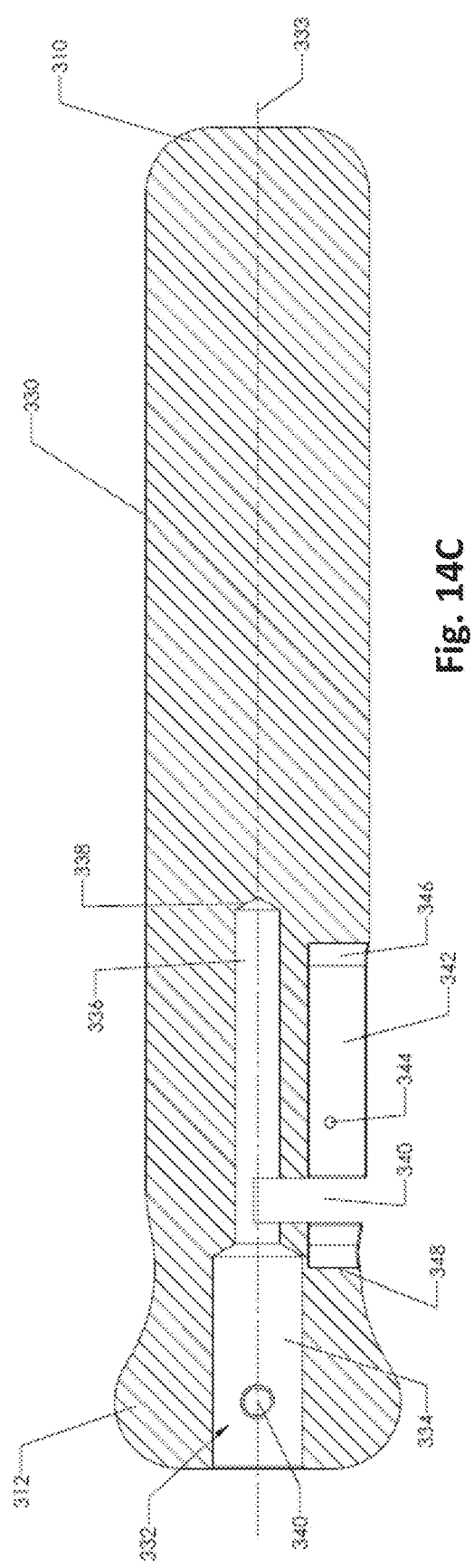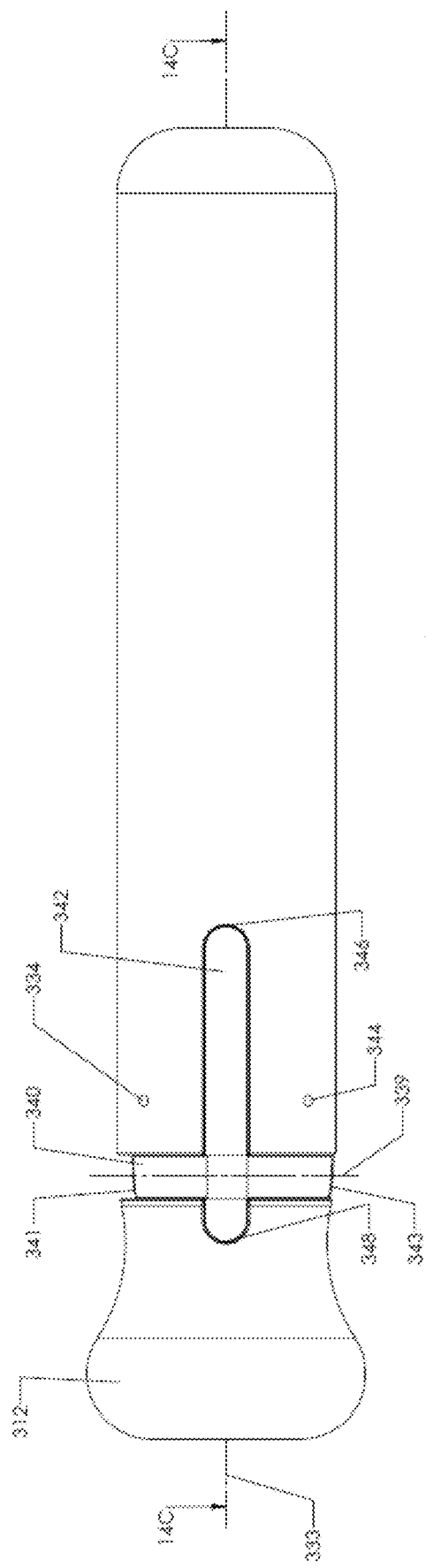

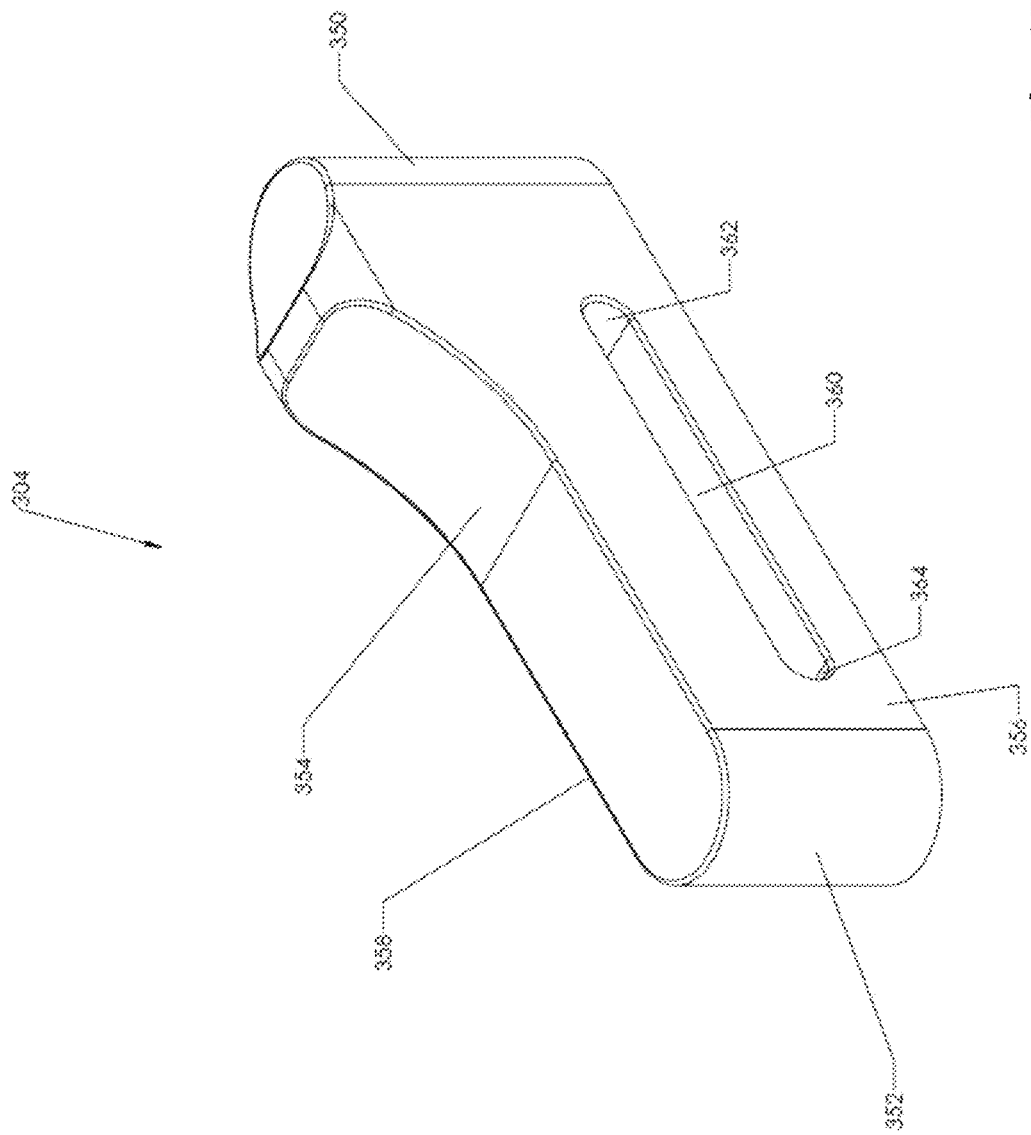

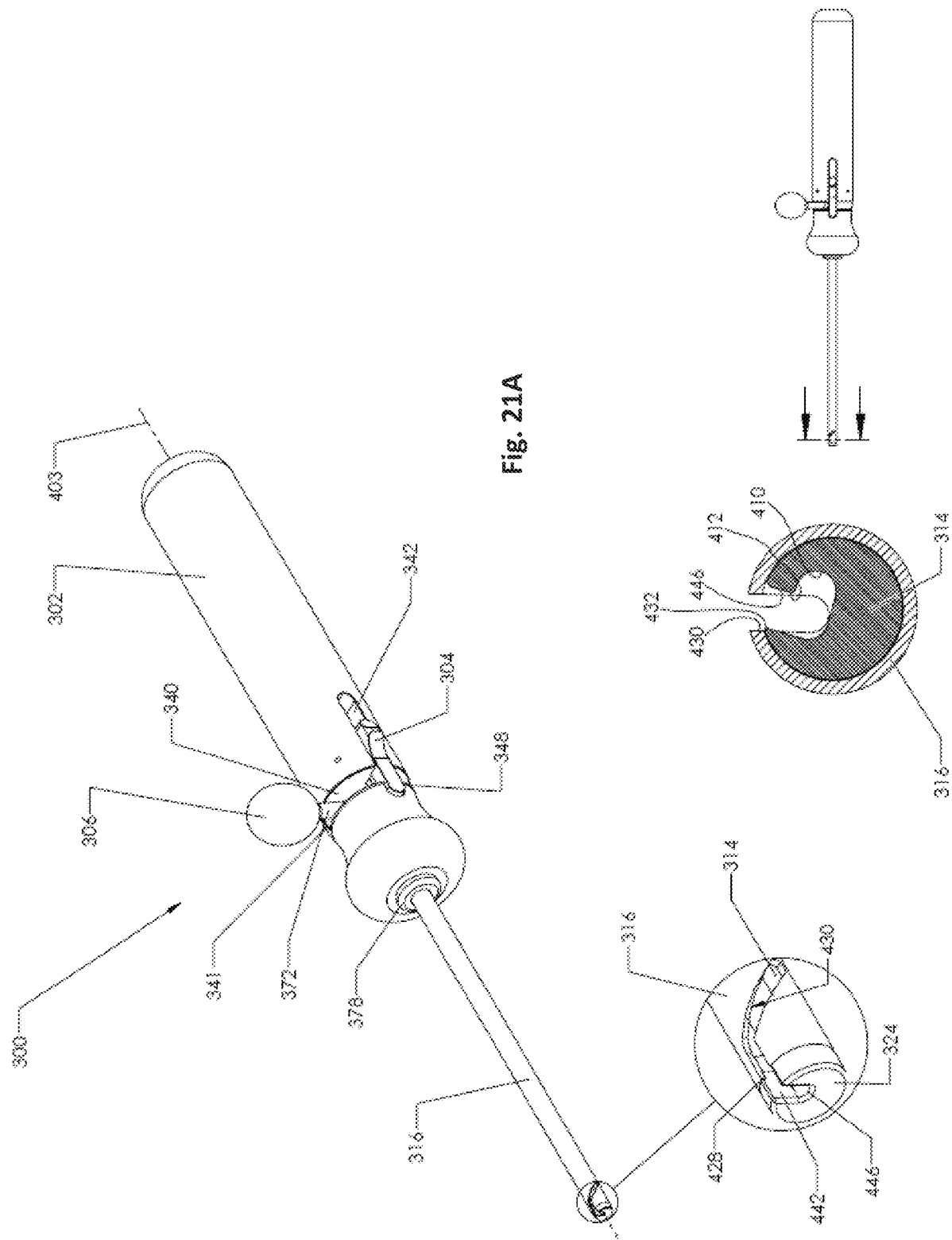

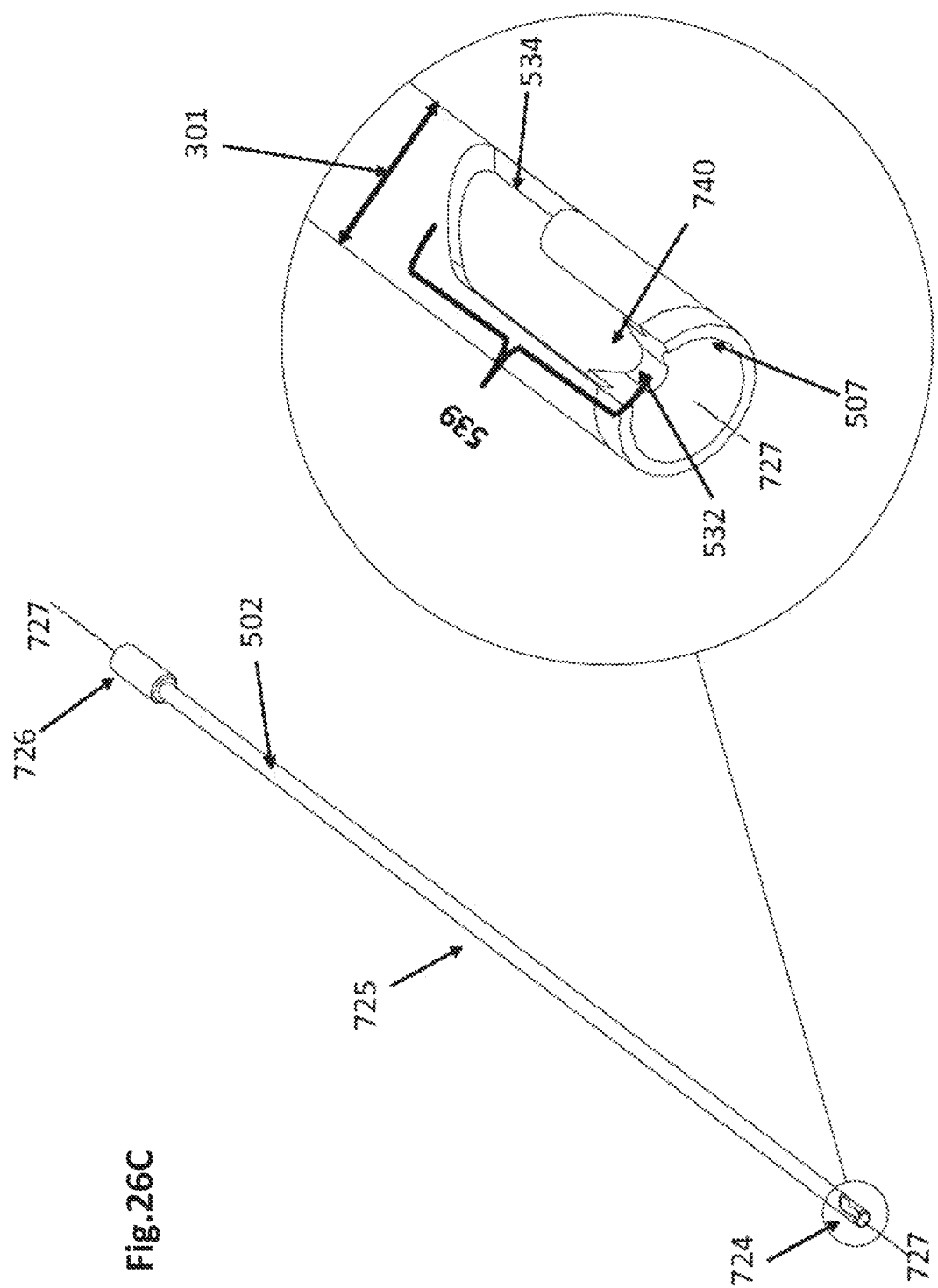

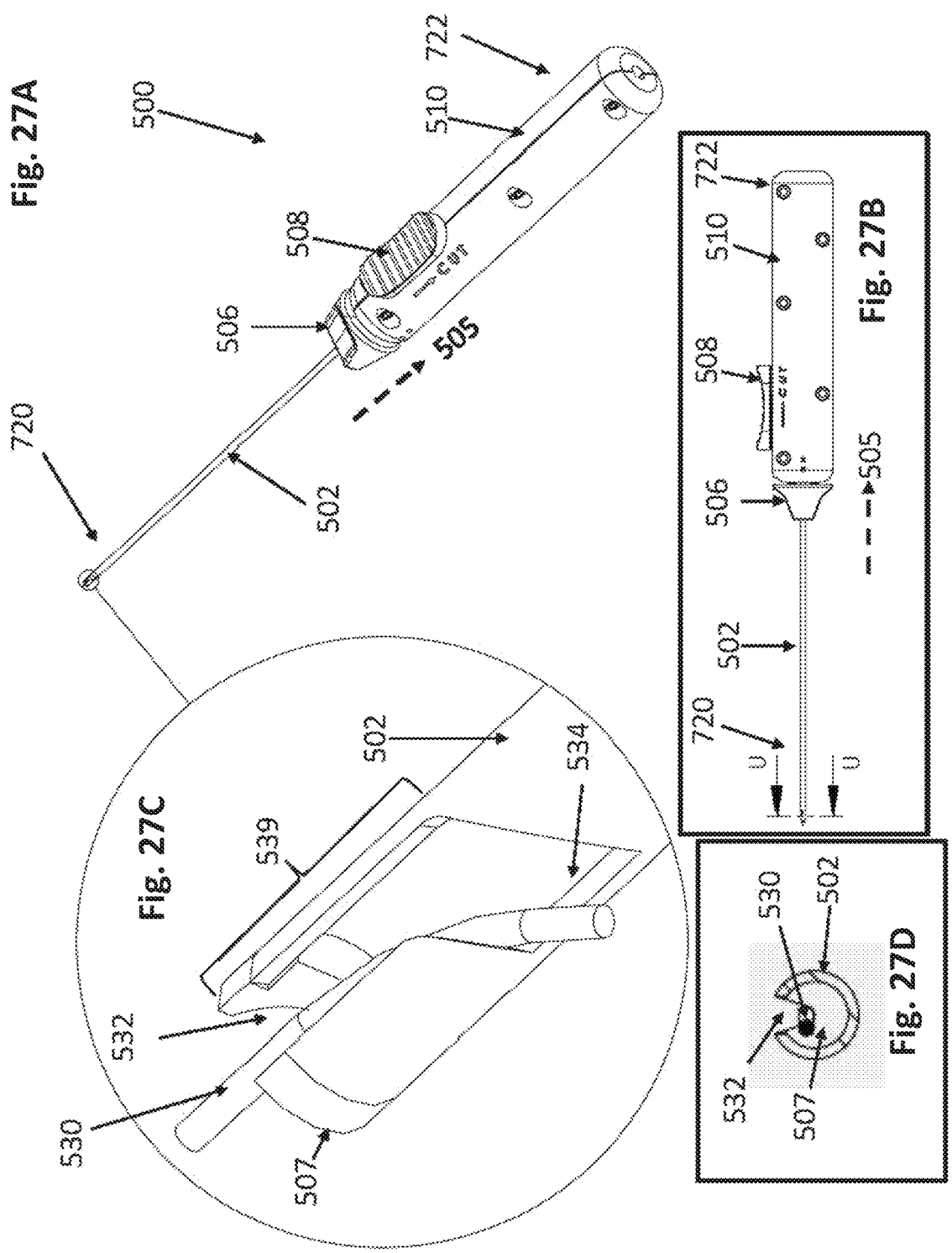

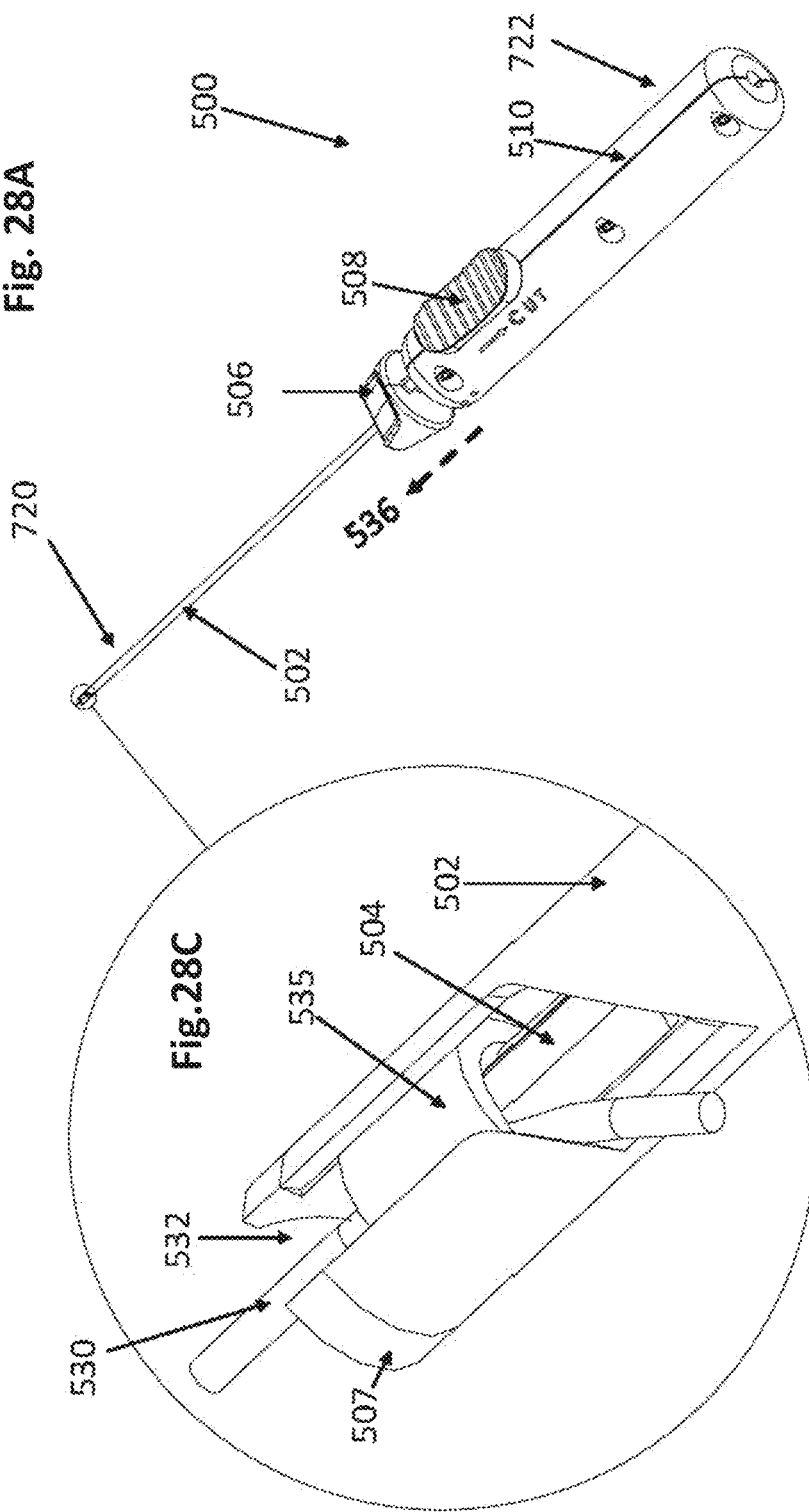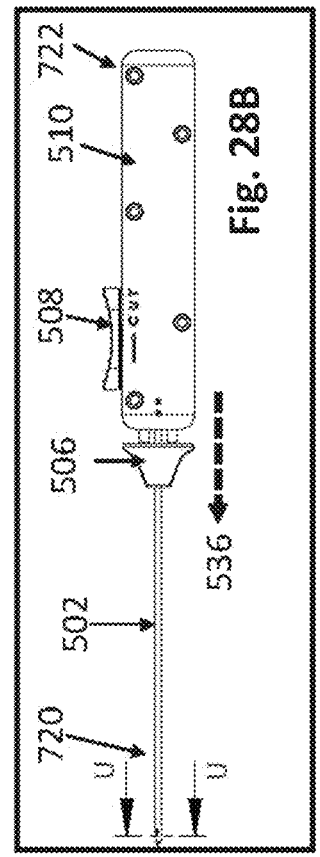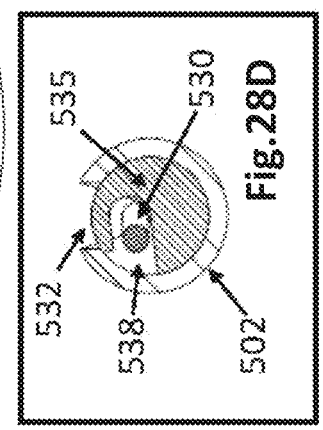

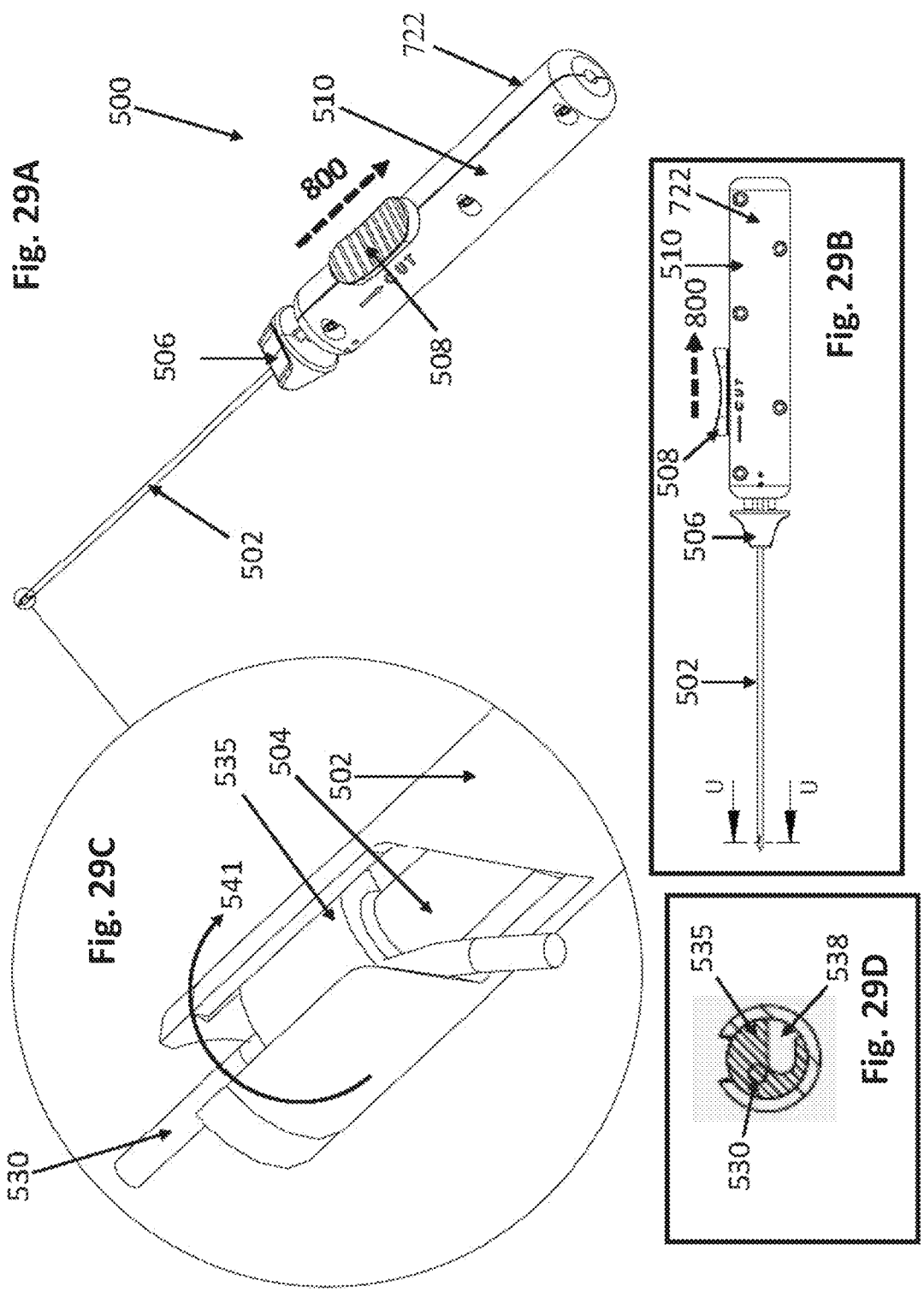

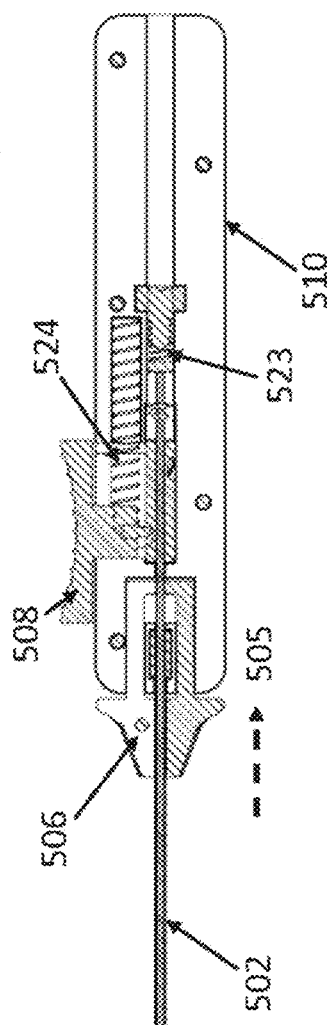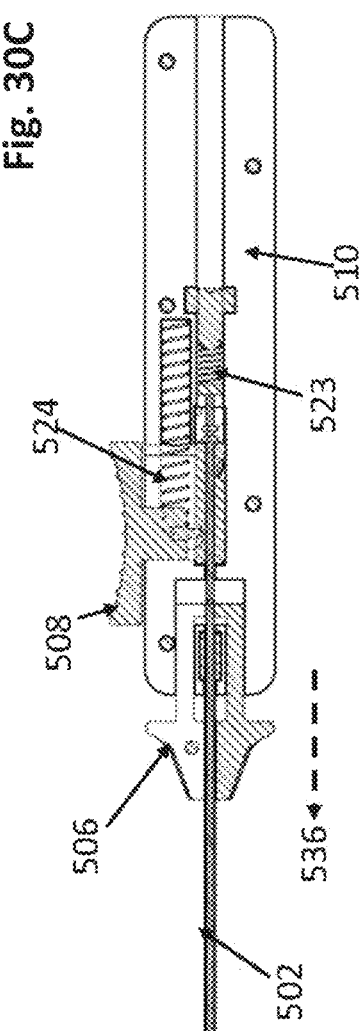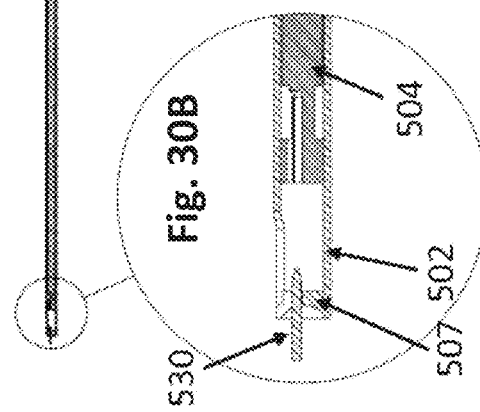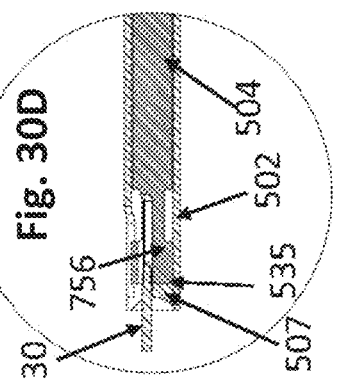

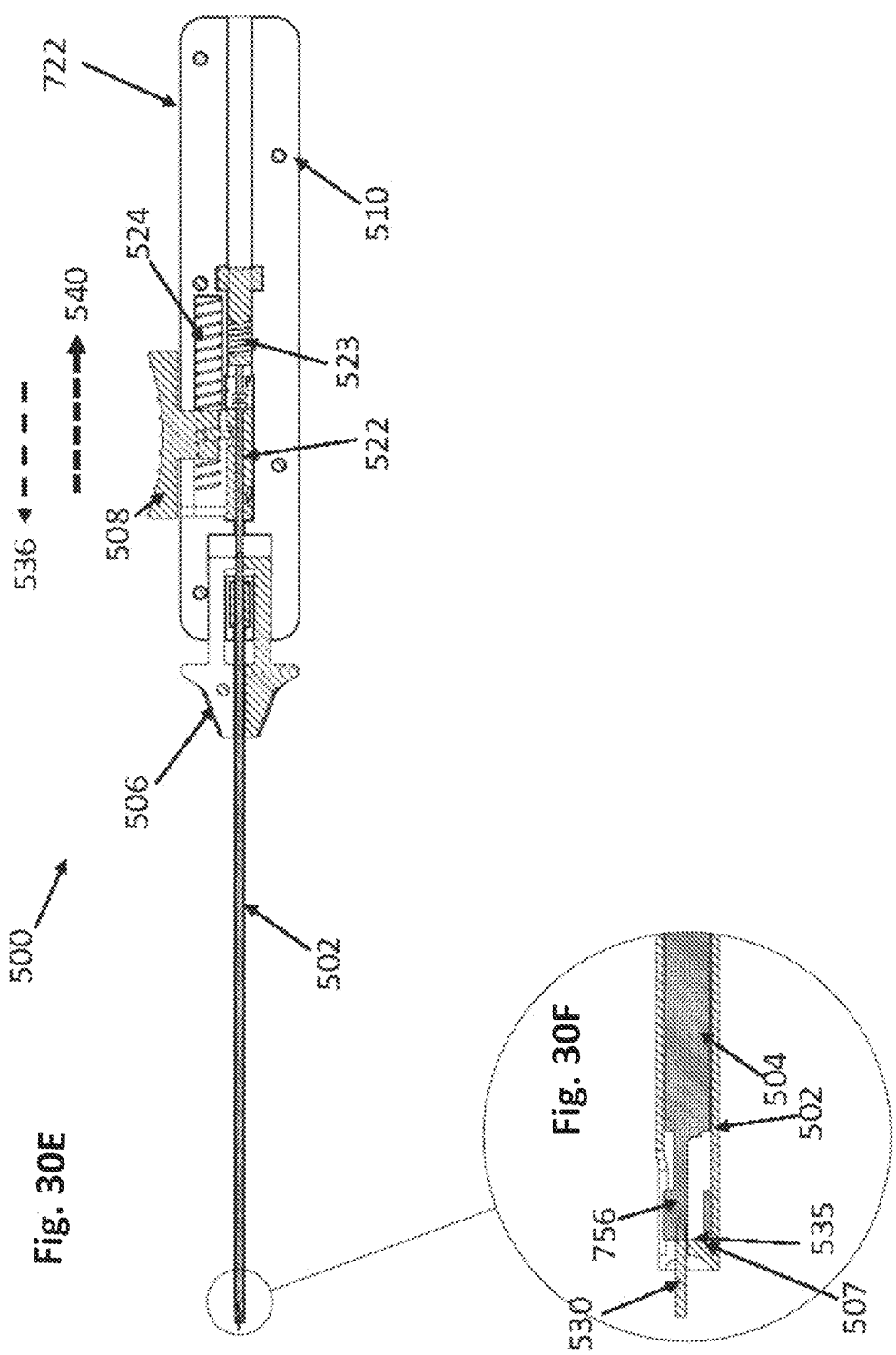

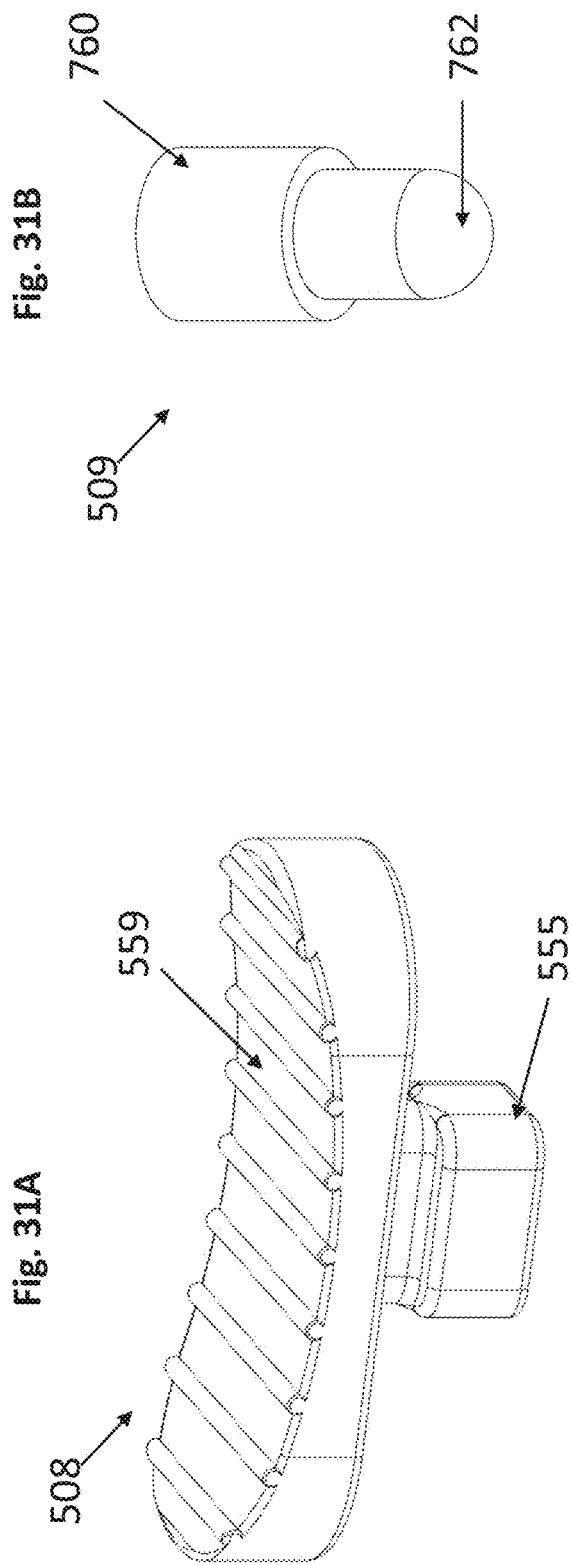

SURGICAL CUTTING DEVICE

RELATED APPLICATIONS

This application is a National Phase of PCT Patent Application No. PCT/IL2016/050881 having International filing date of Aug. 11, 2016, which claims the benefit of priority under 35 USC § 119(e) of U.S. Provisional Patent Application No. 62/203,741 filed on Aug. 11 2015.The contents of the above applications are all incorporated by reference as if fully set forth herein in their entirety.

FIELD AND BACKGROUND OF THE INVENTION

The present invention, in some embodiments thereof, relates to a cutting device and, more particularly, but not exclusively, to a surgical cutting device configured to retain and cut suture threads.

Physicians often close a surgery wound within a patient tissue using sutures. Surgical cutting devices are often used for cutting the ends of sutures employed to close the surgery wound within the patient's tissue.

Additional background art includes U.S. Patent Application No. 2012/0158045, U.S. Patent Application No. 2012/0158045, U.S. Patent Application No. 2003/0181926, U.S. Pat. Nos. 8,568,428, 8,465,512, and 7,905,892.

SUMMARY OF THE INVENTION

The present invention seeks to provide an improved cutting device, including a handle with a lever at least partially inserted therein; an internal cutting element having a cutting edge at its distal end, which is inserted into an external tubular element and wherein both the internal cutting element and the external tubular element are arranged along a mutual longitudinal axis and configured to be attached to the handle. The internal cutting element is slidably movable relative to the external tubular element upon force exertion on the lever in order to selectively obtain a partially-actuated orientation of the cutting device where a surgical suture is retained therein and a cutting orientation of the cutting device where the surgical suture is cut.

Preferably, the cutting device also includes a connecting element operatively connected to the lever and the lever is slidably guided within a longitudinal groove formed in the handle element by means of a first connecting pin which is adapted to slidably travel along a longitudinal opening formed in the lever.

In accordance with an embodiment of the present invention in the partially-actuated orientation, the connecting element is partially deformed following force exertion on the lever by a hand of a user.

Preferably, the cutting device also includes a locking button which is operative to retain the surgical suture within the cutting device in the partially-actuated orientation.

In accordance with an embodiment of the present invention, the slidable travel of the first connecting pin provides for a linear movement of the internal cutting element.

Preferably, the locking button is displaceable sideways in order to assume the cutting orientation.

Still preferably, a longitudinal groove is formed within internal cutting element and a second connecting pin that is inserted within the longitudinal groove connects the internal cutting element with the external tubular element and slidable travel of the second connecting pin provides for angular movement of said internal cutting element.

In accordance to an embodiment of the present invention, the external tubular element includes a diagonally extending groove at its distal end for receiving the surgical suture therein.

Yet preferably, the cutting orientation when the surgical suture is retained within the diagonally extending groove, the cutting edge of the internal cutting element protrudes distally of the diagonally extending groove to enable cutting of the surgical suture.

In accordance to an embodiment of the present invention, in the partially-activated orientation, the cutting edge of the internal cutting element partially protrudes into the diagonally extending groove in order to retain the surgical suture within the cutting device.

In accordance to an alternative embodiment of the present invention, a cutting device, including a handle with a rotating button partially inserted therein; an internal cutting element, which is inserted into an external cutting element and wherein both the internal cutting element and the external tubular element are arranged along a mutual longitudinal axis and configured to be attached to the handle. The internal cutting element is rotatable relative to the external tubular element upon force exertion on the rotating button in order to selectively obtain a partially-actuated orientation of the cutting device where a surgical suture is retained therein and a cutting orientation of the cutting device where the surgical suture is cut.

Preferably, the internal cutting element has a distalmost wall surface and the external cutting element has a distal circumferential edge and wherein the distalmost wall surface is coplanar with the distal circumferential edge.

In accordance with the alternative embodiment of the present invention, the cutting device also includes a biasing element which is disposed within the handle and is adapted to exert constant force on the internal cutting element to provide for the distalmost wall surface being coplanar with the distal circumferential edge.

Preferably, the internal cutting element includes an opening at its distal end, which forms a gap partially along a circumference of the distal end and the external cutting element includes a spirally-shaped groove at its distal end.

Still preferably, in a non-actuated orientation the gap is aligned with a part of the spirally-shaped groove in order to allow insertion of the surgical suture into the cutting device.

Yet preferably, in a partially-actuated orientation the gap is not aligned with a part of the spirally-shaped groove but the opening is partially aligned with the spirally-shaped groove in order to allow retention of the surgical suture within the cutting device.

Still preferably, in a cutting orientation the gap is entirely not aligned with the spirally-shaped groove and the opening is not aligned with the spirally-shaped groove in order to allow cutting of the surgical suture by the cutting device.

In accordance with the alternative embodiment of the present invention, The cutting device also includes a locking button which is axially displaceable in order to block rotation of the rotating button and thus enable retention of the surgical suture within the cutting device in the partially-actuated orientation.

Preferably, the locking button is configured to be longitudinally displaced in order to allow further rotation of the rotating button which allows the cutting device to assume the cutting orientation.

Following are some examples of some embodiments of the invention:

EXAMPLE 1

A device for suture thread cutting, comprising:
a handle;
a stationary external element having a channel at the distal end, and a proximal end connected to said handle, said channel is fitted and shaped for holding a suture thread;
a movable cutter having a cutting edge, partially inserted into said handle, said cutting edge is configured to move between a first position and a second position in said channel;
wherein in said first position the suture thread is retained within the channel and in said second position the suture thread is cut.

EXAMPLE 2

The cutting device of example 1, further comprising:
an aligning element connected to said distal end of said stationary external element comprising an opening;
wherein said opening of said aligning element is fitted to connect the distal end of said channel.

EXAMPLE 3

The cutting device of example 2, wherein said opening of said aligning element is a U-shaped opening.

EXAMPLE 4

The cutting device of example 3, wherein said cutter comprises a distal flange having an opening.

EXAMPLE 5

The cutting device of example 4, wherein said opening is a U-shaped opening.

EXAMPLE 6

The cutting device of example 4, wherein said opening of said flange is aligned with said opening of said aligning element or spaced-apart from said opening of said aligning element for insertion of said thread into said channel.

EXAMPLE 7

The cutting device of example 4, wherein said U-shaped opening of said flange is rotated in at least 90° degrees relative to said U-shaped opening of said aligning element when cutter is in a first position to retain said thread.

EXAMPLE 8

The cutting device of example 5, wherein said U-shaped opening of said flange is rotated in at least 180° degrees relative to said U-shaped opening of said aligning element when cutter is in a second position to cut said thread.

EXAMPLE 9

The cutting device of example 8, wherein said U-shaped opening of said flange comprises a cutting edge configured to apply shear forces on said thread when said flange is rotated in at least 180° degrees relative to said U-shaped opening of said aligning element to cut said thread.

EXAMPLE 10

The cutting device of example 4, wherein in said first position to retain said thread, said flange is moved towards said aligning element of said stationary external element.

EXAMPLE 11

The cutting device of example 9, wherein said cutting edge of said movable cutter moves to a third position, wherein in said third position the suture thread is inserted into said cutting device.

EXAMPLE 12

The cutting device of example 1, wherein said channel is a diagonally extending channel crossing said stationary external element.

EXAMPLE 13

The cutting device of example 1, wherein said handle further comprises a lever configured to selectively move said cutter to said first position and to said second position upon force exertion on said lever.

EXAMPLE 14

The cutting device of example 13, further comprising a locking button operative to retain said cutter in said first position for retaining said thread.

EXAMPLE 15

The cutting device of example 14, wherein said locking button is displaced sideway to move said cutter to said second position for cutting said thread.

EXAMPLE 16

The cutting device of example 13, wherein said lever further comprises a channel;
and wherein movement of a pin within said channel to a proximal direction upon force exertion on said lever, generates a movement of said cutter in a distal direction.

EXAMPLE 17

The cutting device of example 14, wherein said lever further comprises a recess for locking said locking button when said cutter is in said first position for retaining said thread.

EXAMPLE 18

The device of example 1, further comprising a bushing connected to said cutter; wherein said movement of said bushing in a proximal direction retracts said cutter to assume a thread insertion state.

EXAMPLE 19

The device of example 18, further comprising a movable button functionally connected to said cutter; wherein axial sliding of said movable button in a proximal direction rotates said cutter to assume said second position for cutting said thread.

EXAMPLE 20

The device of example 1, wherein said handle further comprising a rotating button partially inserted within said handle;
wherein rotating of said rotating button moves said cutter to said first position for retaining said thread, and to said second position for cutting said thread.

EXAMPLE 21

The cutting device of example 20, comprising an axially displaceable locking button for blocking rotation of said rotating button when said cutter is in said first position for retaining said thread.

EXAMPLE 22

The cutting device of example 21, wherein said locking button is configured to be longitudinally displaced to allow further rotation of said locking button to assume said second position for cutting said thread.

EXAMPLE 23

The cutting device of example 1, wherein said suture thread is cut using shear forces produced by relative rotation between said cutter and said external cutting element.

EXAMPLE 24

A device for suture thread cutting, comprising:
a handle;
a stationary external element, having a channel at the distal end, and a proximal end connected to said handle;
an internal cutter partially inserted into said handle;
wherein said internal cutter is moved within said channel to cut a suture thread inserted into said channel.

EXAMPLE 25

The device of example 24, further comprising a movable button partially inserted into said handle and operatively connected to said internal cutter.

EXAMPLE 26

The device of example 25, further comprising a movement converter placed within said handle and connected to said internal cutter; wherein a connecting member of said movable button is placed within a helical groove on the circumference of said movement converter.

EXAMPLE 27

The device of example 26, wherein movement of said movable button in an axial direction away from said thread, rotates said movement converter and said internal cutter for cutting said thread.

EXAMPLE 28

The device of example 24, wherein movement of said internal cutter within said channel for cutting said thread applies shear forces on said thread.

EXAMPLE 29

The device of example 24, wherein said internal cutter comprises a cutting edge.

EXAMPLE 30

The cutting device of example 24, further comprising a lever partially inserted into said handle; wherein said internal cutter slides in an axial direction towards said channel upon force exertion on said lever.

EXAMPLE 31

The cutting device of example 24, further comprising a rotation button partially inserted into said handle; wherein said rotation of said rotation button rotates said internal cutter within said channel for cutting said thread.

EXAMPLE 32

A device for suture thread cutting, comprising:
a handle;
a stationary external element, having a channel at the distal end, and a proximal end connected to said handle;
an internal cutter partially inserted into said handle, said internal cutter is moved within said channel to cut a suture thread inserted into said channel;
a movable button partially inserted into said handle and operatively connected to said internal cutter;
wherein movement of said movable button in an axial direction away from said thread rotates said internal cutter for cutting said thread.

EXAMPLE 33

The device of example 32, further comprising a movement converter placed within said handle and connected to said internal cutter; wherein a connecting member of said movable button is placed within a helical groove on the circumference of said movement converter.

EXAMPLE 34

The device of example 33, wherein said movement of said movable button rotates said movement converter.

EXAMPLE 35

A method for cutting a suture thread by a cutting device, comprising:
inserting a suture thread into a channel at the distal end of said cutting device sliding a movable button of said cutting device in an axial direction towards the proximal end of said cutting device to cause rotation of an internal cutter of said cutting device.

EXAMPLE 36

The method of example 35, further comprising:
manually moving a bushing connected to said internal cutter in an axial direction towards the proximal end of said cutting device before said inserting.

EXAMPLE 37

The method of example 36, further comprising:
retaining said thread within said channel before said sliding.

EXAMPLE 38

The method of example 35, wherein said rotation further comprises applying shear forces on said thread.

EXAMPLE 39

A method for cutting a suture thread by a cutting device, comprising:
inserting a suture thread into said cutting device;
retaining said suture thread within said cutting device by moving an internal element of said cutting device, wherein said retaining allows freely moving of said suture thread within said cutting device; and
cutting said suture thread by further moving said internal element.

EXAMPLE 40

The method of example 39, further comprising:
sliding said cutting device along said thread, before said cutting.

EXAMPLE 41

The method of example 40, wherein said sliding further comprises pushing a knot towards the sutured tissue.

EXAMPLE 42

The method of example 39, wherein said cutting further comprises applying shear forces on said thread by a cutting edge of said internal element.

EXAMPLE 43

The method of example 39, wherein said cutting further comprises rotating said internal element.

EXAMPLE 44

The method of example 39, wherein said cutting further comprises sliding said internal element in an axial direction.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 4 is a simplified pictorial view illustration of a connection element, connecting between the lever of FIG. 3 and the handle of FIGS. 2A and 2B, according to some embodiments of the invention;

FIG. 5 is a simplified pictorial view illustration of a locking button of the cutting device of FIG. 1C, according to some embodiments of the invention;

FIGS. 6A and 6B are simplified respective elevation and sectional views of a bushing of the cutting device of FIG. 1C, according to some embodiments of the invention; section being taken along lines 6B-6B in FIG. 6A;

FIGS. 7B and 7C are simplified broken-out section views of the cutting element of FIG. 7A, according to some embodiments of the invention;

FIGS. 8A and 8B are simplified pictorial view illustrations of an external tubular element of the cutting device of FIG. 1C, shown from two opposite sides, according to some embodiments of the invention;

FIGS. 8C and 8D are simplified sectional illustrations of an external tubular element of the cutting device of FIGS. 8A and 8B, according to some embodiments of the invention; section lines being taken along lines 8C-8C in FIG. 8A and along lines 8D-8D in FIG. 8B;

FIGS. 14A-14C are simplified respective pictorial view, elevation view and section view illustrations of a handle of the cutting device of FIG. 13, according to some embodiments of the invention; FIG. 14C is taken along lines 14C-14C in FIG. 14B;

FIG. 15 is a simplified pictorial view illustration of a locking button, which is configured to be partially inserted into the handle of FIGS. 14A-14C, according to some embodiments of the invention;

FIG. 17B is taken along lines 17B-17B in FIG. 17A;

FIGS. 21A and 21B are simplified respective pictorial view and elevation view illustrations of an assembled cutting device of FIG. 13 in a non-actuated orientation, according to some embodiments of the invention;

FIG. 26C is a schematic illustration depicting an external element of the cutting device, according to some embodiments of the invention;

FIGS. 27A-27D are schematic illustration depicting the device of FIG. 26A in a thread insertion position, according to some embodiments of the invention;

FIGS. 28A-28D are schematic illustration depicting the device of FIG. 26A in a thread retention position, according to some embodiments of the invention;

FIGS. 29A-29D are schematic illustration depicting the device of FIG. 26A in a thread cutting position, according to some embodiments of the invention;

FIGS. 30A and 30B are cross-section illustrations depicting the device of FIG. 26A in a thread insertion position, according to some embodiments of the invention;

FIGS. 30C and 30D are cross-section illustrations depicting the device of FIG. 26A in a thread retention position, according to some embodiments of the invention;

FIGS. 30E and 30F are cross-section illustrations depicting the device of FIG. 26A in a thread cutting position, according to some embodiments of the invention;

FIG. 31A is a schematic illustration depicting a cutting control element of the cutting device, according to some embodiments of the invention;

FIG. 31B is a schematic illustration depicting a connecting pin of the cutting control element, according to some embodiments of the invention;

FIG. 31C is a schematic side view depicting a movement converter element of the cutting device, according to some embodiments of the invention;

FIG. 31D is a schematic front view depicting the movement converter element of FIG. 31C, according to some embodiments of the invention;

Figure 1A:
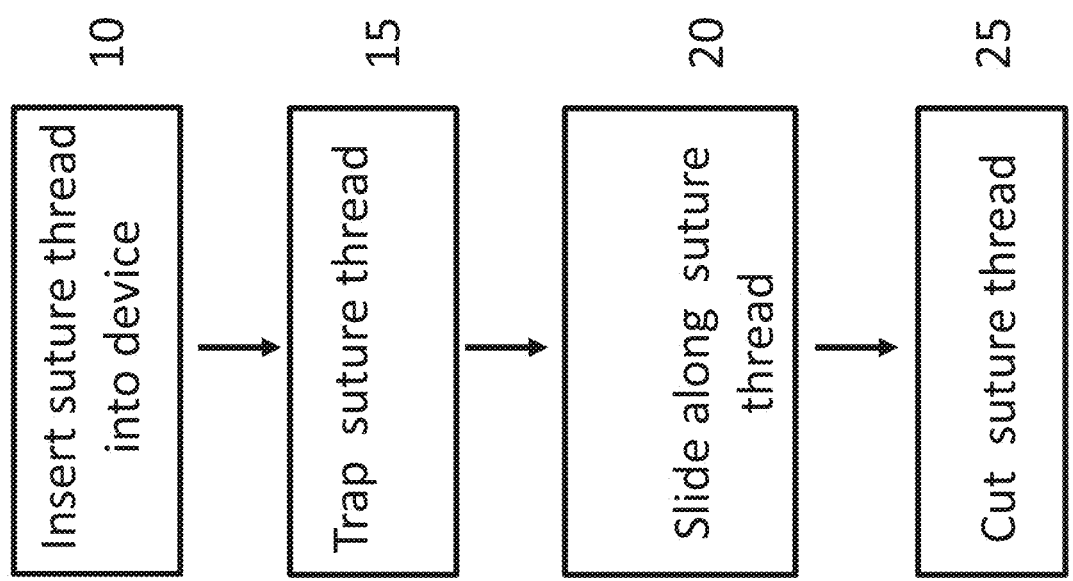
FIG. 1A is a general flow chart of the cutting process using the device, according to some embodiments of the invention.

DESCRIPTION OF SPECIFIC EMBODIMENTS
OF THE INVENTION

The present invention, in some embodiments thereof, relates to a cutting device and, more particularly, but not exclusively, to a surgical cutting device configured to retain and cut suture threads.

An aspect of some embodiments relates to a cutting element of a suture cutting device configured to capture and cut a suture thread. In some embodiments, the cutting element is selectively positionable in a thread retention state and in a thread cutting state. Optionally, the cutting element is selectively positionable in a thread insertion state.

In some embodiments, the cutting element is positioned in a thread insertion state, when a retention control element connected to the cutting element is moved towards the proximal end of the suture cutting device. In some embodiments, in a thread insertion state a groove in the cutting device is opened to allow, for example, the insertion or loading of a suture thread into the device. Optionally, opening of the groove in the cutting device allows, for example to unload a thread. In some embodiments, after the insertion of the suture thread, the cutting element is manually moved towards the distal end of the suture cutting device, for example to capture the thread. Alternatively, after the insertion of the suture thread, a biasing element, for example a coil spring relaxes and moves the cutting element towards the distal end of the device.

In some embodiments, in a thread retention state the thread is retained within the cutting device. In some embodiments, in a thread retention state the thread moves in a closed section of the cutting device, optionally formed by the cutting element and an external element of the cutting device. In some embodiments, in a thread retention state the cutting device can slide along the thread, for example, to reach a desired cutting location. Alternatively, the cutting device slides along the thread to push a knot towards the sutured tissue.

In some embodiments, the cutting element is further selectively moved to a thread cutting state. In some embodiments, the cutting element slides in an axial direction toward the distal end of the cutting device to make contact between a cutting edge of the cutting element and the thread for example, to allow cutting of the thread. Alternatively, the cutting element is rotated to allow, for example contact between a cutting edge of the cutting element and the thread. In some embodiments, when the cutting edge of the cutting element is in contact with the thread, the cutting edge applies shear forces on the thread. Optionally, the applied shear forces allow for example, cutting of the thread.

An aspect of some embodiments relates to an inner cutting element, configured to cut a suture thread by moving inside an external element of a suture cutting device. In some embodiments, the cutting element slides in an axial direction within the external element to allow for example, cutting of the thread. Alternatively, the cutting element rotates within the elongated element to allow for example, cutting of the thread. Optionally, the inner cutting element is configured to rotate while sliding in an axial direction within the elongated element. In some embodiments, movement of the inner cutting element generates shear forces on the thread which optionally, cut the thread.

In some embodiments, it is a potential advantage of the cutting device that the inner cutting element moves entirely within the external element of the suture cutting device. Optionally, the inner cutting element does not protrude out from the external element of the cutting device. In some embodiments, movement of the inner cutting element within the external element prevents any direct contact between the inner cutting element and the tissue. In some embodiments, avoiding a direct contact between the inner cutting element and the tissue allows, for example to prevent direct application of force by the cutting device on the tissue.

An aspect of some embodiments relates to a cutting element of a suture cutting device configured to cut a thread when a cutting control element is moved away, for example in an axial direction, from the thread location. In some embodiments, when the cutting control element is moved away from the thread, the cutting element slides in an axial direction towards the thread. Alternatively, the movement of the cutting control element away from the thread is converted into a rotational movement of the cutting element. Optionally, the movement of the cutting control element is converted to a rotational movement of the cutting element while it slides in an axial direction towards the thread. In some embodiments, a potential advantage of the cutting device is that the force applied by the user on the device is not applied at the direction of the tissue.

An aspect of some embodiments relates to a cutting element of a suture cutting device configured to cut a suture thread by a rotational movement. In some embodiments, the cutting element is rotated within an external element of the cutting device. Optionally, rotation of the cutting element applies shear forces on the thread. In some embodiments, rotation of the cutting element allows, for example, to apply shear forces that are not in the direction of the tissue.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Cutting Process

Reference is now made to FIG. 1A, a general process for cutting a suture thread, according to some exemplary embodiments of the invention.

According to some exemplary embodiments, a suture thread is inserted into the cutting device at 10. Optionally, the ending portion of the suture thread is inserted into the cutting device. In some embodiments, the suture thread in inserted through an opening in the cutting device, for example through an opening at the distal end of the cutting device.

According to some exemplary embodiments, after the thread is inserted into the device, a retaining mechanism is activated at 15. In some embodiments, activation of the retaining mechanism prevents the release of the thread from the cutting device. In some embodiments, activation of the retaining mechanism forms a closed loop around the thread.

According to some exemplary embodiments, after the thread is retained, the device slides on the thread at 20, for example by passing the thread through openings in the device, until a desired cutting point is reached. Optionally, the desired cutting point is in close proximity to the suture knot.

According to some exemplary embodiments, when the desired cutting point is reached, a cutting mechanism is activated at 25. In some embodiments, a cutting mechanism is activated after a security switch is moved to a position that permits cutting of the thread. In some embodiments, a cutting mechanism is activated by moving an inner cutting element through the thread. In some embodiments, the inner cutting element applies shear forces on the thread, for example to cut the thread.

In some embodiments, the cutting mechanism is activated by pressing a lever, for example a lever connected to a handle of the cutting device. Alternatively, the cutting mechanism is activated by turning or moving a handle.

Exemplary Cutting Device

Figure 1B:
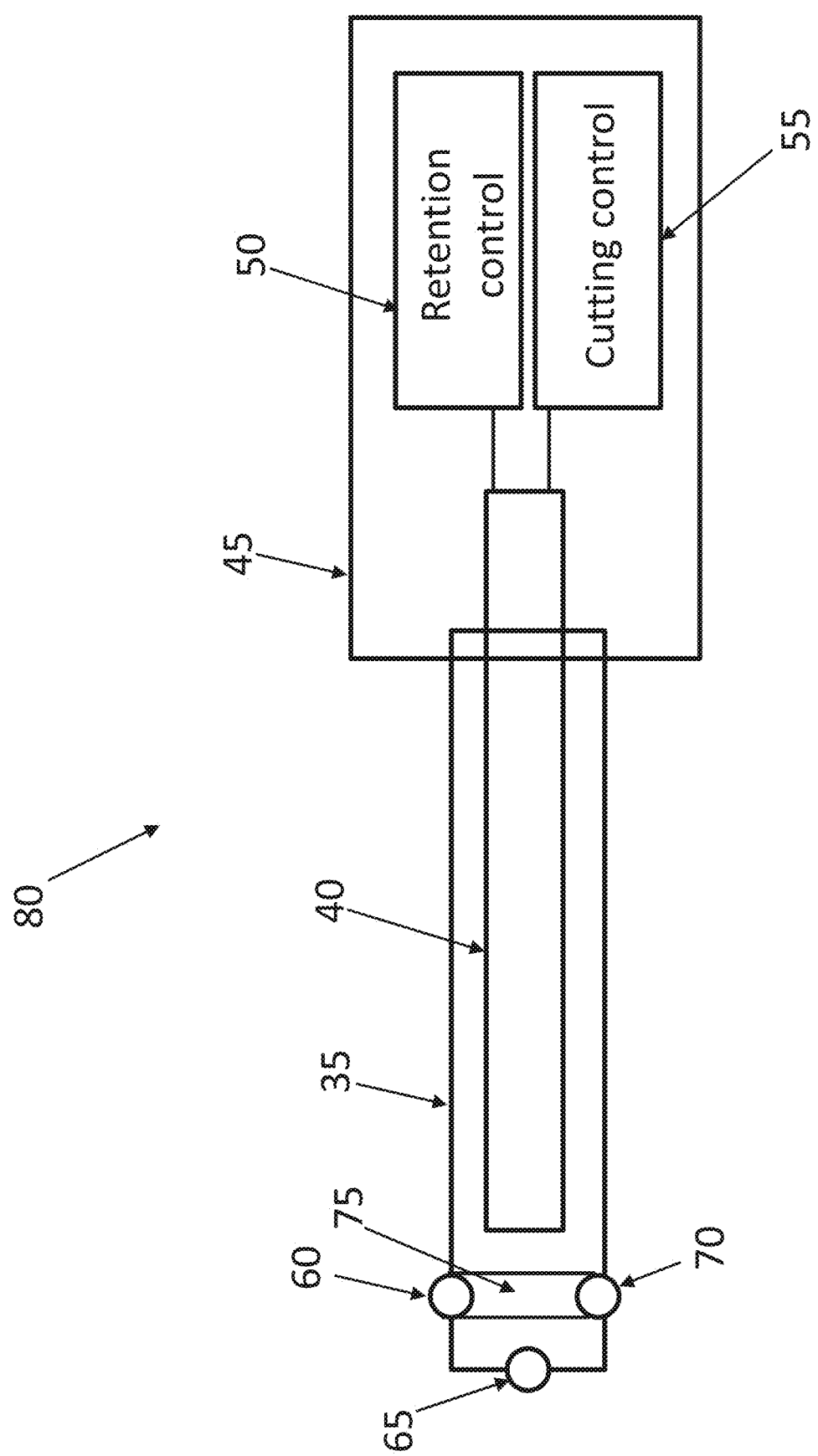
FIG. 1B is a block diagram depicting a suture cutting device, according to some embodiments of the invention.

Reference is now made to FIG. 1B depicting the main components of a suture cutting device, according to some exemplary embodiments of the invention.

According to some embodiments, cutting device 80 comprises a stationary external element, for example elongated element 35, connected to a handle 45. In some embodiments, elongated element 35 comprises at least one opening at its distal end, for example 1, 2, 3 openings. In some embodiments, elongated element 35 comprises at least one opening at its distal front edge, for example opening 65, and an additional opening in one of the sides, for example opening 70. Optionally, the additional opening is located on the circumference of elongated element 35. Alternatively, elongated element 35 comprises two side openings, for example openings 60 and 70. Optionally, both opening 60 and opening 70 are positioned on the circumference of elongated element 35. In some embodiments, opening 60 and opening 70 are parts of a channel 75 in the circumference of the stationary external element, for example elongated element 35. Optionally, channel 75 is fitted and shaped to allow, for example the insertion of a suture thread. In some embodiments, the suture thread has in approximation a diameter of 0.4 mm, for example 0.35 mm, 0.32 mm, 0.3 mm or less. In some embodiments, insertion of a suture thread through an opening, for example channel 75 in a stationary external element, is a potential advantage of the cutting device. In some embodiments, insertion or loading of a thread into a fixed element prevents, for example direct application of force on the tissue by a movable element of the cutting device.

According to some embodiments, cutting device 80 comprises a cutting element 40 connected to handle 45 and positioned within a stationary external element, for example elongated element 35. In some embodiments, cutting element 40 is configured to slidably move and/or rotate inside elongated element 35. In some embodiments, cutting element 40 comprises a cutting edge, optionally at the distal end of cutting element 40. Optionally, cutting element 40 comprises a channel at the distal end. In some embodiments, the channel comprises a cutting edge at the distal end of the channel. In some embodiments, a suture thread is inserted into the channel of the cutting element, when the channel of the cutting element is aligned with a channel of the stationary external element, for example channel 75. In some embodiments, after the insertion of the suture thread, the cutting element is moved to the proximal end of the cutting device, for example to allow the cutting edge of the cutting element channel to cut the suture thread.

According to some embodiments, cutting device 80 comprises a retention mechanism configured to capture and retain a suture thread. In some embodiments, the retention mechanism is controlled by retention control 50 located in handle 45 and connected to cutting element 40. In some embodiments, retention control 50 controls the linear movement of cutting element 40 within elongated element 35. Optionally, the retention mechanism comprises a biasing element, for example a coil spring.

According to some embodiments, cutting device 80 comprises a cutting mechanism configured to cut a suture thread. In some embodiments, the cutting mechanism is controlled by a cutting control 55, located in handle 45 and connected to cutting element 40. In some embodiments, cutting control 55 controls the linear movement of cutting element 40 within elongated element 35. Alternatively, cutting control 55 controls the rotation of cutting element 40 within elongated element 35.

Exemplary Cutting Device Operated by Lever Pressing

Figure 1C:
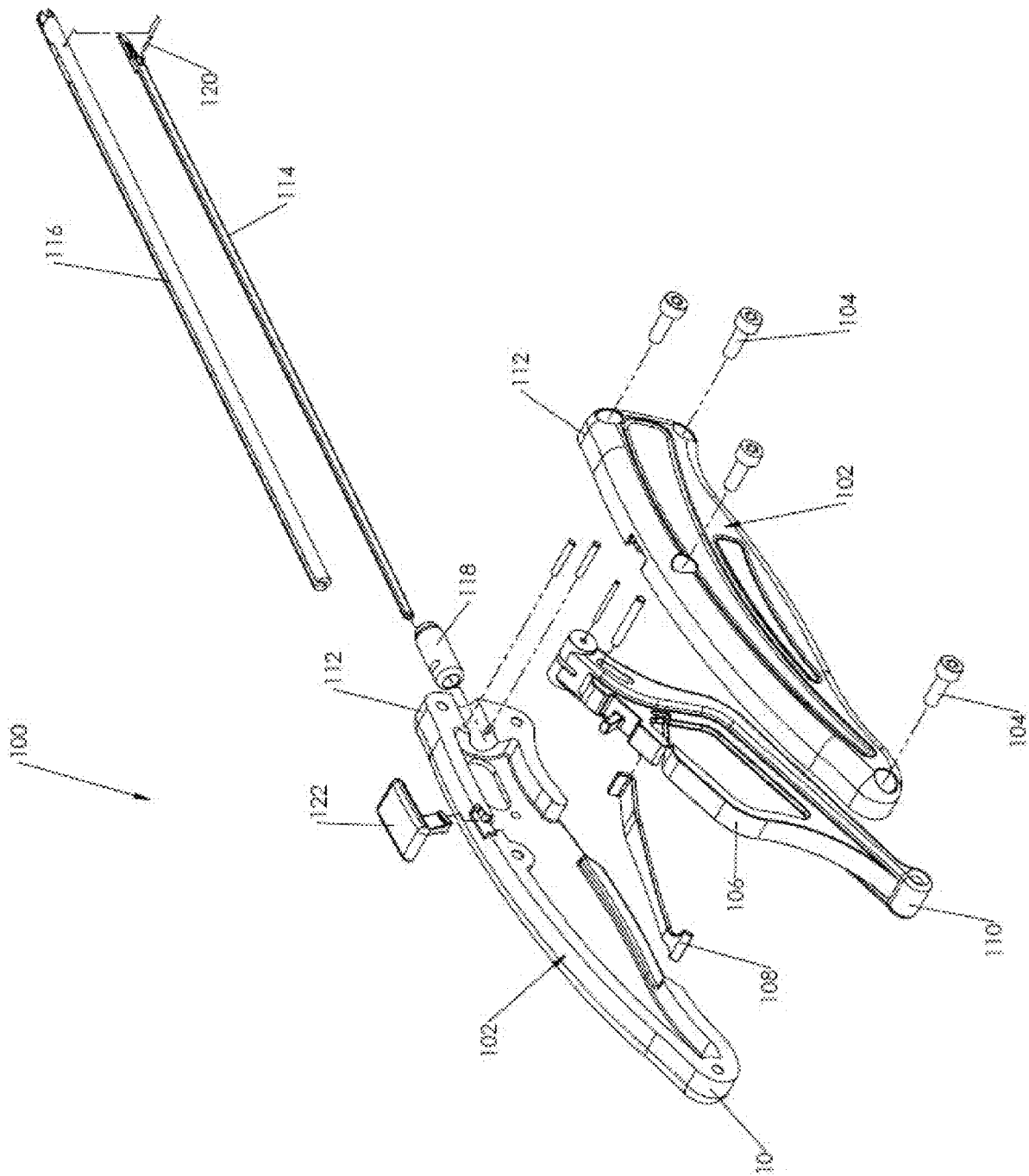
FIG. 1C is a simplified exploded view illustration of a cutting device constructed and operative, according to some embodiments of the invention.

Reference is now made to FIG. 1C, depicting a simplified exploded view illustration of a cutting device 100 constructed and operative, according to some exemplary embodiments of the invention.

According to some exemplary embodiments, for example as seen in FIG. 1C, the cutting device 100 includes a handle 102, typically made of two symmetrical portions, which are attached to each other using bolts 104, or alternatively using any other connection means.

In some embodiments, partially inserted into the handle 102 is a lever 106, configured for operating the cutting device 100 and, optionally enable cutting orientation thereof. In some embodiments, the lever 106 is connected to handle 102 by means of connection element 108.

According to some exemplary embodiments, for example as seen in FIG. 1C handle 102 has a proximal end 110 and a distal end 112. In some embodiments, a cutting element 114, which is enclosed within an external tubular element 116 is partially inserted into the distal end 112 of handle 102 by means of a bushing 118. In some embodiments, the cutting element 114 is slidably attached to the external tubular element 116 using a pin 120.

According to some exemplary embodiments, a locking button 122 is partially disposed within handle 102 and optionally, configured to lock the cutting device 100 in the partially-activated orientation.

Figure 2A:
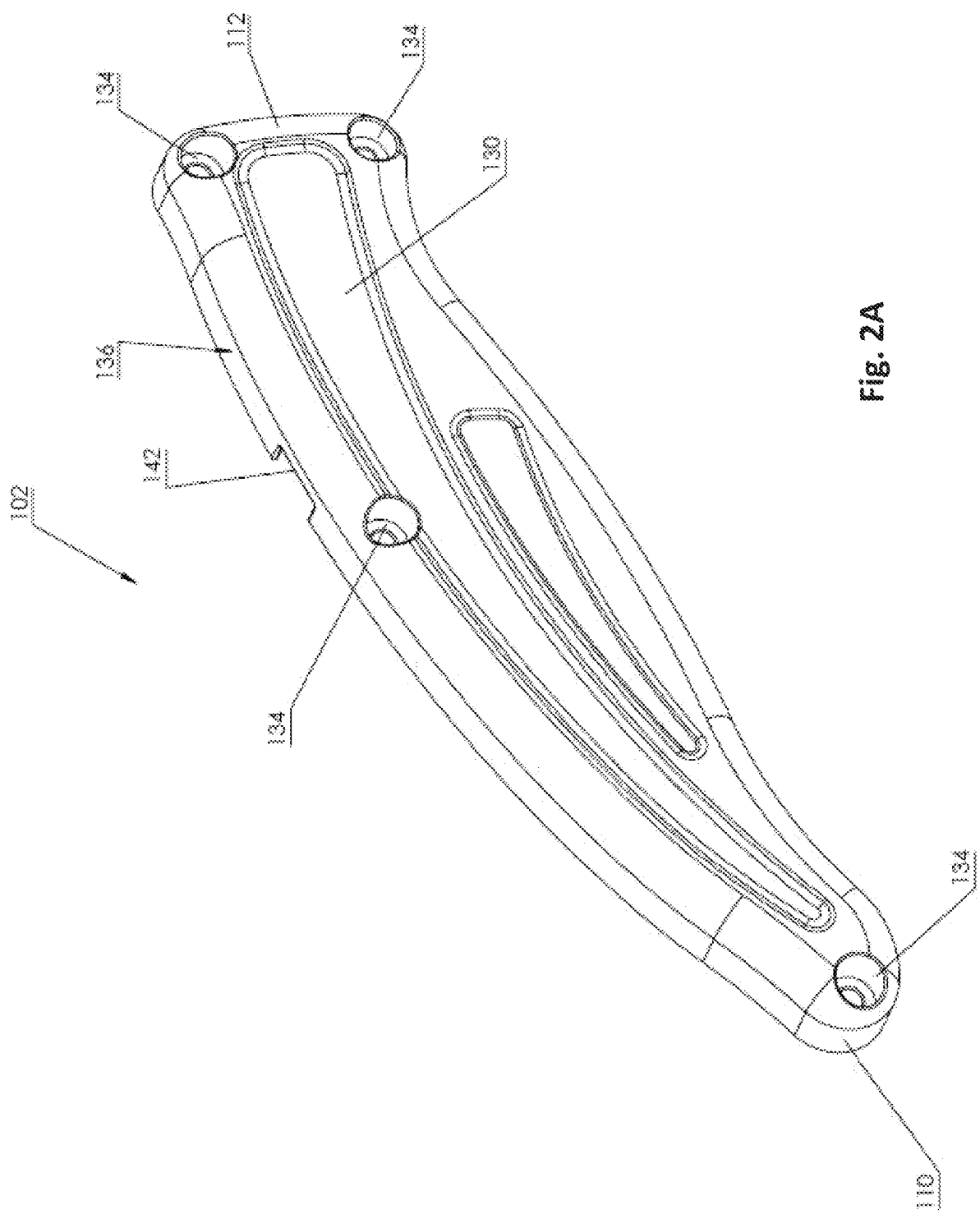
FIGS. 2A and 2B are simplified pictorial view illustrations of a handle of the cutting device of FIG. 1C, according to some embodiments of the invention.
Figure 2B:
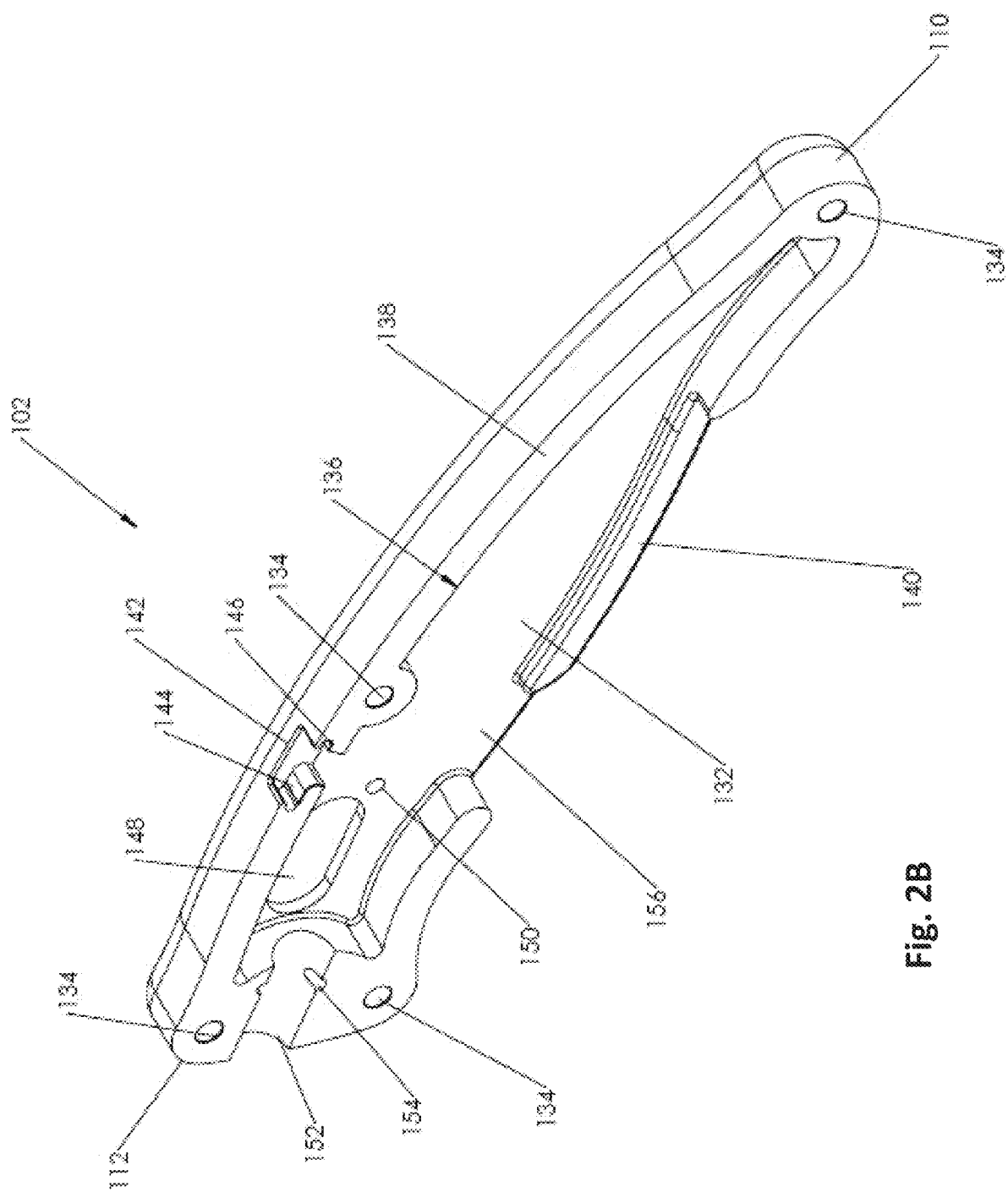

Reference is now made to FIGS. 2A and 2B, which are simplified pictorial view illustrations of handle 102 of the cutting device 100 of FIG. 1C, according to some embodiments of the device.

It is appreciated that any form of handle 102 can be used for the cutting device 100 in accordance with some embodiments of the present invention. In some embodiments, handle 102 has a proximal end 110 and a distal end 112, an outer surface 130 and an inner surface 132.

According to some exemplary embodiments, handle 102 includes several apertures 134 for insertion of bolts 104 for attachment of the two parts of handle 102. In some embodiments, the inner surface 132 of handle 102 is formed as an internal recess in handle 102. In some embodiments, there is a circumferential edge 136 inwardly extending from inner surface 132. Optionally, when the two parts of handle 102 are assembled, circumferential edges 136 of both parts 102 are positioned adjacent one another. In some embodiments, circumferential edge 136 includes an upper portion 138 and a lower portion 140. In some embodiments, an opening 142 is formed at the upper portion 138 of circumferential edge 136 typically adjacent the distal end 112 of handle 102 for insertion of locking button 122 therein.

According to some embodiments, opening 142 has a proximally extending protrusion 144 that extends from its distal end and a proximally extending recess 146 that extends from its proximal end.

It is additionally seen in FIGS. 2A and 2B that a longitudinal groove 148 is formed on inner surface 132 adjacent the distal end 112 of handle 102 for moveable connection of the lever 106 with handle 102, in accordance with some embodiments. In some embodiments, an opening 150 is formed proximally of groove 148.

In some embodiments, a generally cylindrical groove 152 is formed at the distal end 112 of handle 102 for insertion of bushing 118 therein. Optionally, two recesses 154 for insertion of pins are formed on the groove 152.

Figure 3:
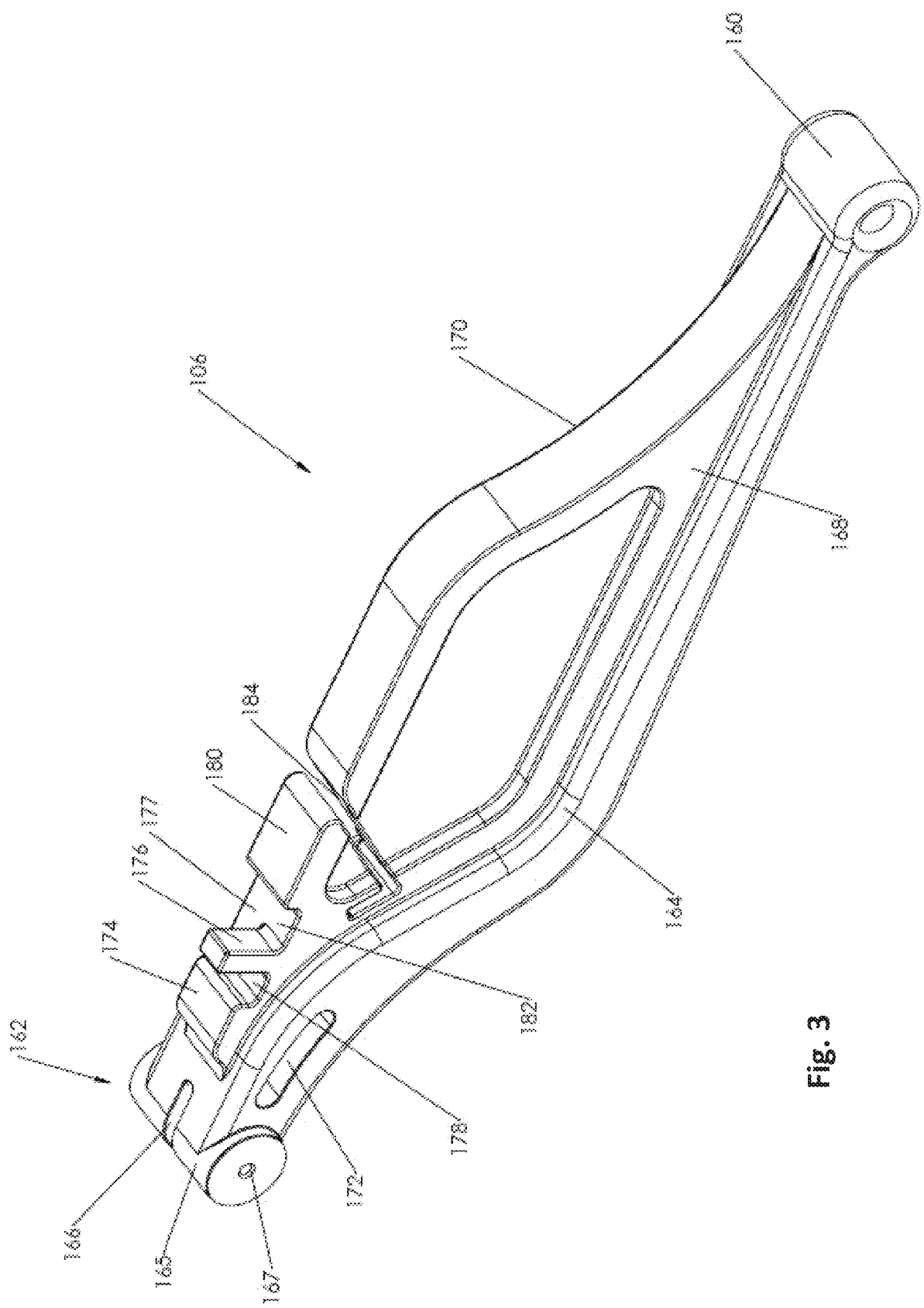
FIG. 3 is a simplified pictorial view illustration of a lever, which is configured to be partially inserted into the handle of FIGS. 2A and 2B, according to some embodiments of the invention.

As specifically seen in FIG. 2B, an opening 156 is formed through circumferential edge 136, through which the lever 106 protrudes out of handle 102, in accordance with some embodiments of the invention Reference is now made to FIG. 3, which is a simplified pictorial view illustration of the lever 106, which is configured to be partially inserted into the handle 102 of FIGS. 2A and 2B, according to some embodiments of the invention.

According to some exemplary embodiments, the lever 106 has a proximal end 160, a distal end 162 and an intermediate grasping portion 164. In some embodiments, a generally cylindrical element 165 is formed at the distal end 162 of lever 106, optionally for insertion into longitudinal groove 148 of handle 102. The cylindrical element 165 has a groove 166 for insertion of cutting element 114 and a through bore 167 for insertion of a connecting pin therethrough.

According to some embodiments, the lever 106 has a first side surface 168 and a second side surface 170. It is seen in FIG. 3 that a longitudinal opening 172 is formed from first side surface 168 to second side surface 170 and is disposed adjacent the distal end 162 of lever 106, in accordance with some embodiments of the invention.

According to some embodiments, a first upwardly extending protrusion 174 is generally disposed adjacent the distal end 162 of the lever 106 above the longitudinal opening 172. In some embodiments, slightly proximally spaced from the first protrusion 174 is a second protrusion 176, which is spaced from the first protrusion 174 by a recess 178. In some embodiments, it is noted that the second protrusion 176 extends upwardly to a greater extent than the first protrusion 174 and it is further noted that the second protrusion 176 is narrower than first protrusion 174 and leaves a gap 177 laterally of second protrusion 176.

It is additionally seen in FIG. 3 that a third protrusion 180 is slightly spaced from the second protrusion 176, which is spaced from the second protrusion 176 by a recess 182, I accordance with some embodiments of the invention.

Additionally, an L-shaped recess 184 is formed proximally and adjacent to the third protrusion 180.

Reference is now made to FIG. 4, which is a simplified pictorial view illustration of the connection element 108, connecting between the lever 106 of FIG. 3 and the handle 102 of FIGS. 2A and 2B, according to some embodiments of the invention.

In some embodiments, the connection element 108 is integrally made of a relatively resilient material, such as a resilient metal and generally functions as a leaf spring.

It is seen in FIG. 4 that connection element 108 has a proximal end 190, a distal end 192 and an intermediate portion 194, in accordance with some embodiments of the invention. In some embodiments, the proximal end 190 has a protrusion 196 adapted for insertion into the handle element 102. Additionally, the distal end 192 has a protrusion 198 for insertion into the lever element 106.

Reference is now made to FIG. 5, which is a simplified pictorial view illustration of the locking button 122 of the cutting device 100 of FIG. 1C, according to some embodiments of the invention.

In some embodiments, the locking button 122 has a gripping portion 200 and a generally longitudinal protrusion 202 extending generally perpendicularly from the gripping portion 200. In some embodiments, longitudinal protrusion 202 is formed in an inverted T-shape, having a laterally extending portion 204 at the free end of longitudinal protrusion 202, which is distanced from the gripping portion 200.

Reference is now made to FIGS. 6A and 6B, which are simplified respective elevation and sectional views of the bushing 118 of the cutting device 100 of FIG. 1C, according to some embodiments of the invention, section being taken along lines 6B-6B in FIG. 6A.

According to some embodiments, bushing 118 is a generally cylindrical hollow element having an inner surface 210 and an outer surface 212. Generally two diametrically opposed recesses 214 are formed on the outer surface 212 of bushing 118 for engagement with connection pins.

Figure 7A:
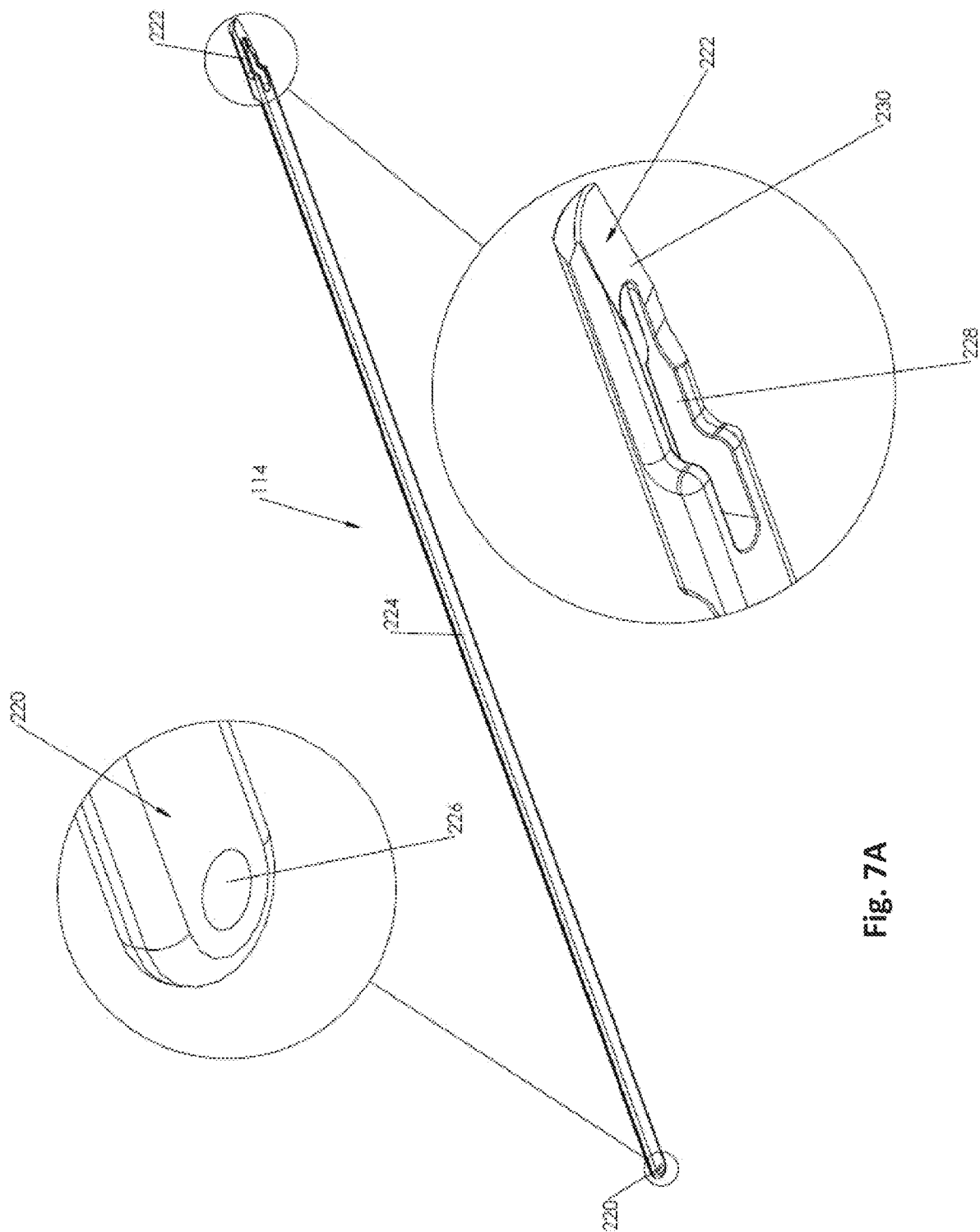
FIG. 7A is a simplified pictorial view illustration of a cutting element of the cutting device of FIG. 1C, according to some embodiments of the invention.

Reference is now made to FIG. 7A, which is a simplified pictorial view illustration of the cutting element 114 of the cutting device 100 of FIG. 1C and to FIGS. 7B and 7C, which are simplified broken-out section views of the cutting element 114 of FIG. 7A, according to some embodiments of the invention.

According to some embodiments, the cutting element 114 has a proximal end 220, a distal end 222 and an intermediate portion 224. In some embodiments, the cutting element 114 is an integrally formed longitudinal element, preferably made of metal.

In some embodiments, there is a through bore 226 in the proximal end 220 for insertion of a connection pin therethrough. It is additionally seen in FIGS. 7A-7C that there is a longitudinal groove 228 formed in the distal end 222 of the cutting element 114 for slidable movement of pin 120 therealong. In some embodiments, the longitudinal groove 228 is disposed adjacent the distal end 222 and preferably extends slightly proximally therefrom. In some embodiments, a cutting edge 230 is formed on the distal end 222 of the cutting element 114.

Figure 8A:
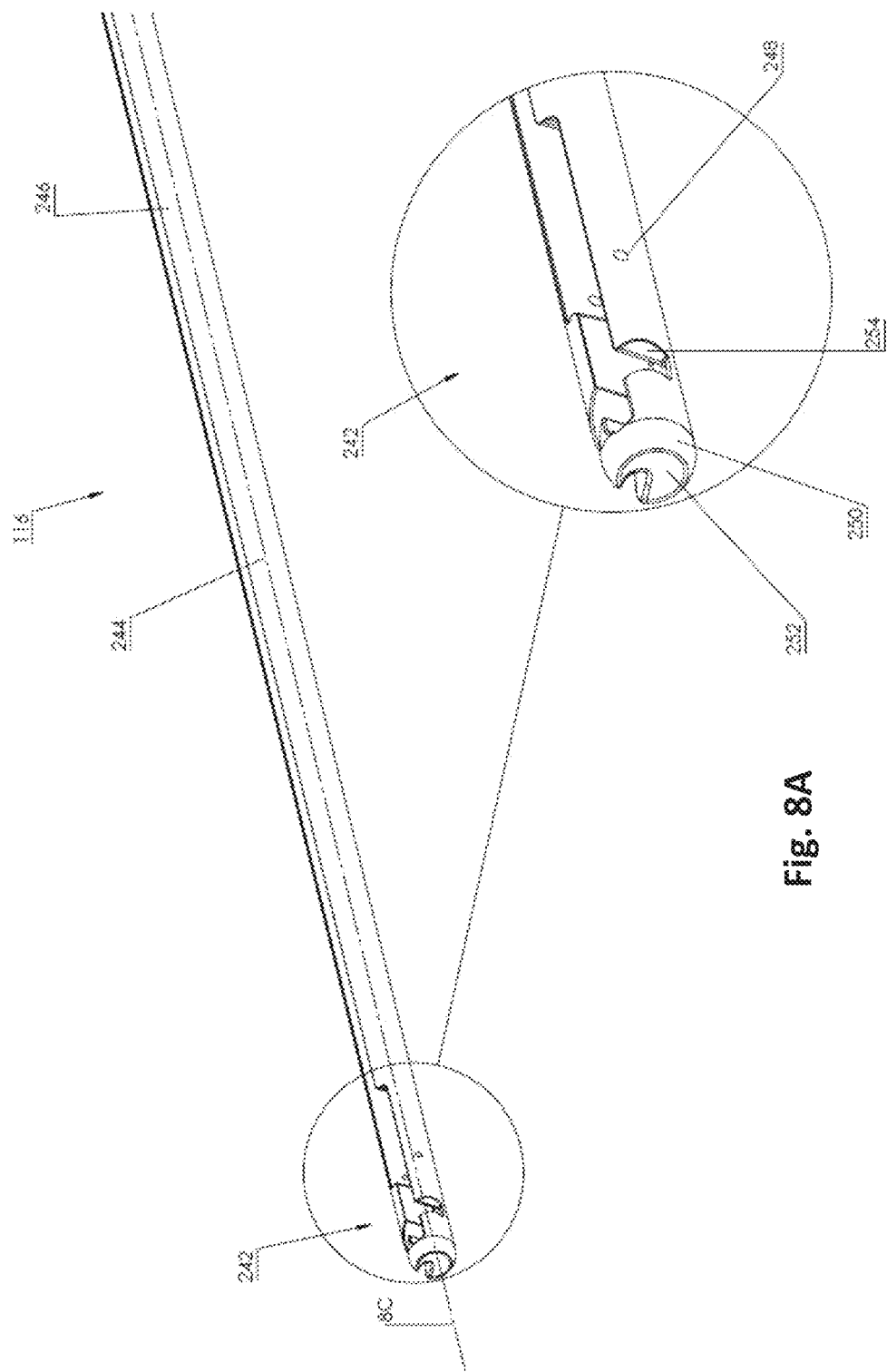

Reference is now made to FIGS. 8A and 8B, which are simplified pictorial view illustrations of the external tubular element 116 of the cutting device 100 of FIG. 1C, shown from two opposite sides and to FIGS. 8C and 8D, which are simplified sectional illustrations of the external tubular element 116 of the cutting device 100 of FIGS. 8A and 8B, according to some embodiments of the invention, section lines being taken along lines 8C-8C in FIG. 8A and along lines 8D-8D in FIG. 8B.

According to some embodiments, the external tubular element 116 has a proximal end 240, a distal end 242 and an intermediate portion 244. In some embodiments, the external tubular element 116 is an integrally formed longitudinal element, preferably made of metal.

It is seen in FIGS. 8A-8D that a longitudinal groove 246 longitudinally extends through the proximal end 240 and the intermediate portion 244 of external tubular element 116 forming a partial enclosure for the cutting element 114, which is inserted therethrough, in accordance with some embodiments of the invention.

In some embodiments, a through opening 248 is formed proximally to distal end 242 of the external tubular element 116 for insertion of pin 120 therethrough. In some embodiments, the distal end 242 terminates at a distal flange 250, having a distally facing surface 252.

According to some embodiments, a diagonally extending groove 254 is formed at the distal end 242 for example, for insertion of a surgical suture therein. As used herein, the term/phrase surgical suture means suture thread. In some embodiments, the diagonally extending groove 254 intersects the longitudinal groove 246.

Figure 9A:
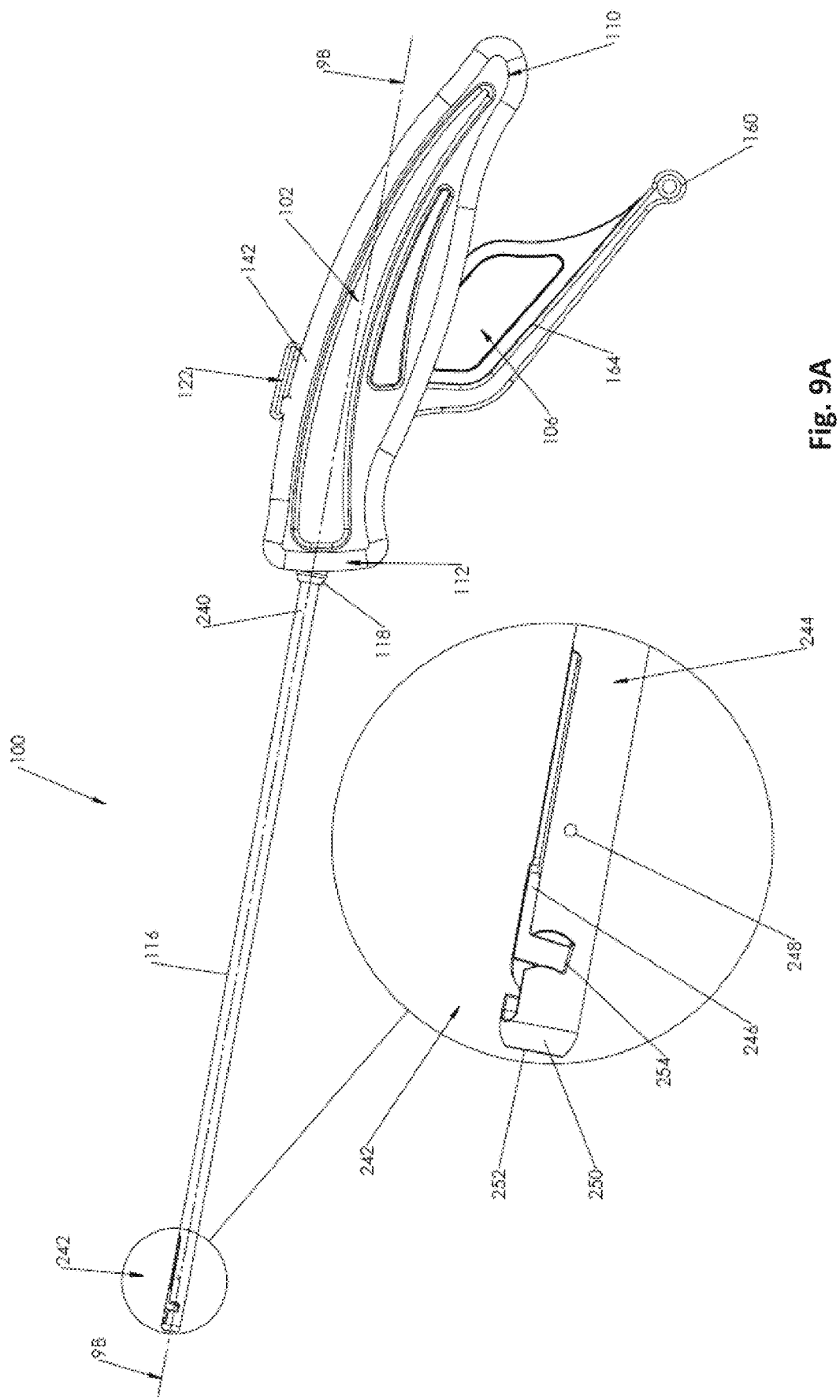
FIG. 9A is a simplified pictorial view illustration of an assembled cutting device of FIG. 1C in a non-actuated orientation, according to some embodiments of the invention.
Figure 9B:
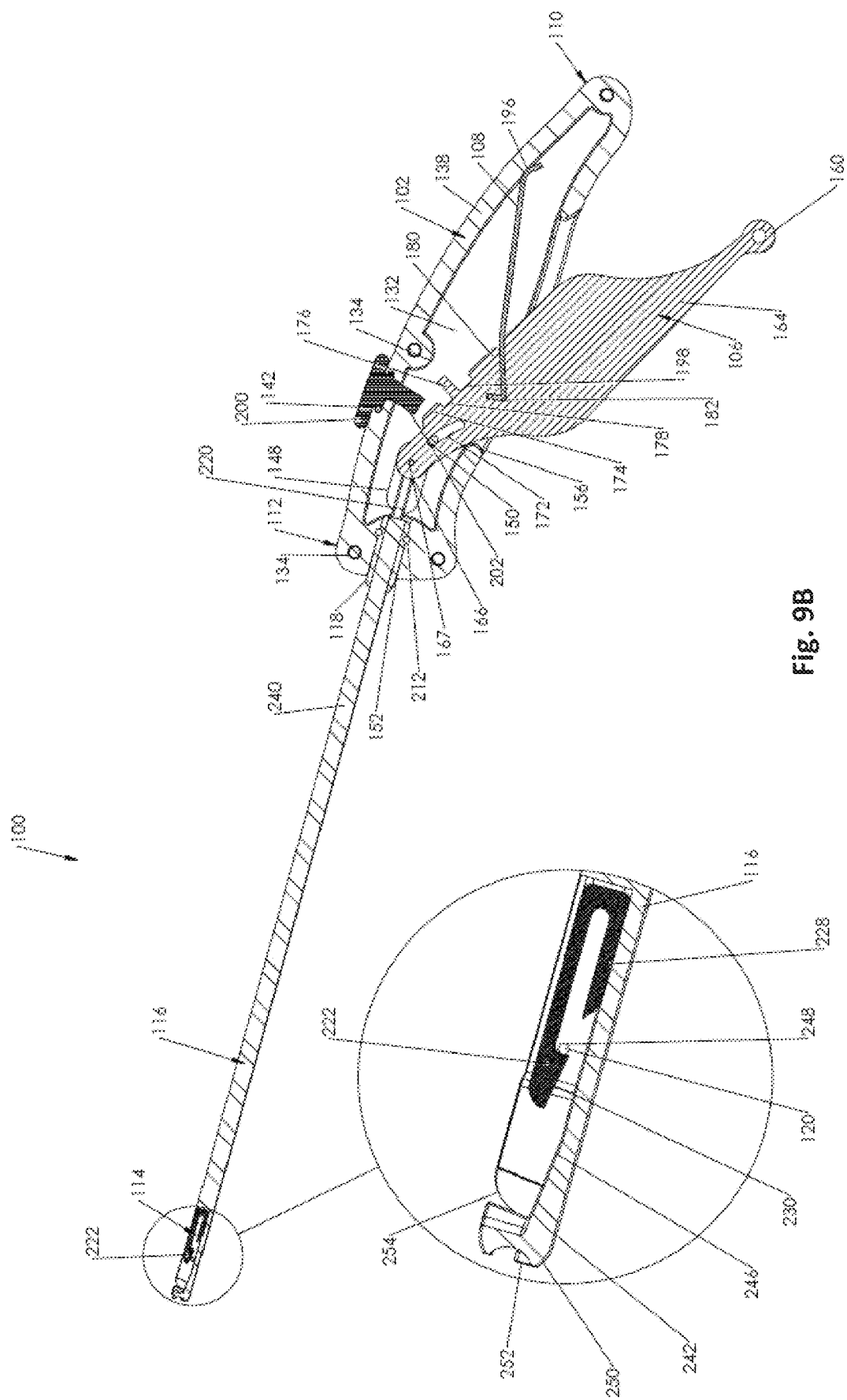
FIG. 9B is a simplified sectional illustration of the assembled cutting device of FIG. 9A in a non-actuated orientation, according to some embodiments of the invention; section being taken along lines 9B-9B in FIG. 9A.

Reference is now made to FIG. 9A, which is a simplified pictorial view illustration of an assembled cutting device 100 of FIG. 1C in a non-actuated orientation and to FIG. 9B, which is a simplified sectional illustration of the assembled cutting device 100 of FIG. 9A in a non-actuated orientation, according to some embodiments of the invention, section being taken along lines 9B-9B in FIG. 9A.

It is a particular feature of some embodiments of the present invention that cutting device 100 can be introduced through the same portal of the surgical suture and the use of an additional portal is obviated due to the particular structure of cutting device 100, which receives the surgical suture within diagonally extending groove 254.

In some embodiments, the cutting device 100 is shown in non-actuated orientation, for example in a retention state in FIGS. 9A and 9B. In some embodiments, the lever 106 is partially inserted into the handle element 102, such that the intermediate portion 164 of lever 106 extends through opening 156 of handle element 102. Additionally, connection element 108 is inserted into the L-shaped recess 184 of lever 106 and is supported against the circumferential edge 136 of handle element 102. Optionally, the connecting element 108 is disposed in a non-deformed orientation in this non-actuated orientation of FIGS. 9A and 9B.

In some embodiments, the locking button 122 is inserted into opening 142 of the handle element 102 and the generally longitudinal protrusion 202 of locking button 122 is disengaged from lever 106.

It is further seen that, in some embodiments, the cylindrical element 165 of lever 106 is slidably guided within longitudinal groove 148 of handle element 102. Additionally, a connecting pin is adapted to slidably travel along longitudinal opening 172 of lever 106.

In some embodiments, bushing 118 is inserted into cylindrical groove 152 of handle element using connecting pins that are inserted between recesses 154 of handle element 102 and recesses 214 of bushing 118.

According to some embodiments, for example as seen in FIG. 9B, the cutting element 114 is inserted through groove 166 of cylindrical element 165 and is connected thereto using a connection pin. In some embodiments, the cutting element 114 is disposed within the external cylindrical element 116 and the distal end 222 of cutting element 114 is spaced proximally from the distal flange 250 of the external cylindrical element 116 by a first distance.

In some embodiments, a connection pin is inserted through longitudinal groove 228 of the cutting element 114 and lies adjacent the cutting edge 230 thereof. In this orientation, the distal end 222 of cutting element 114 does not protrude into the diagonally extending groove 254 of external cylindrical element 116.

Figure 10A:
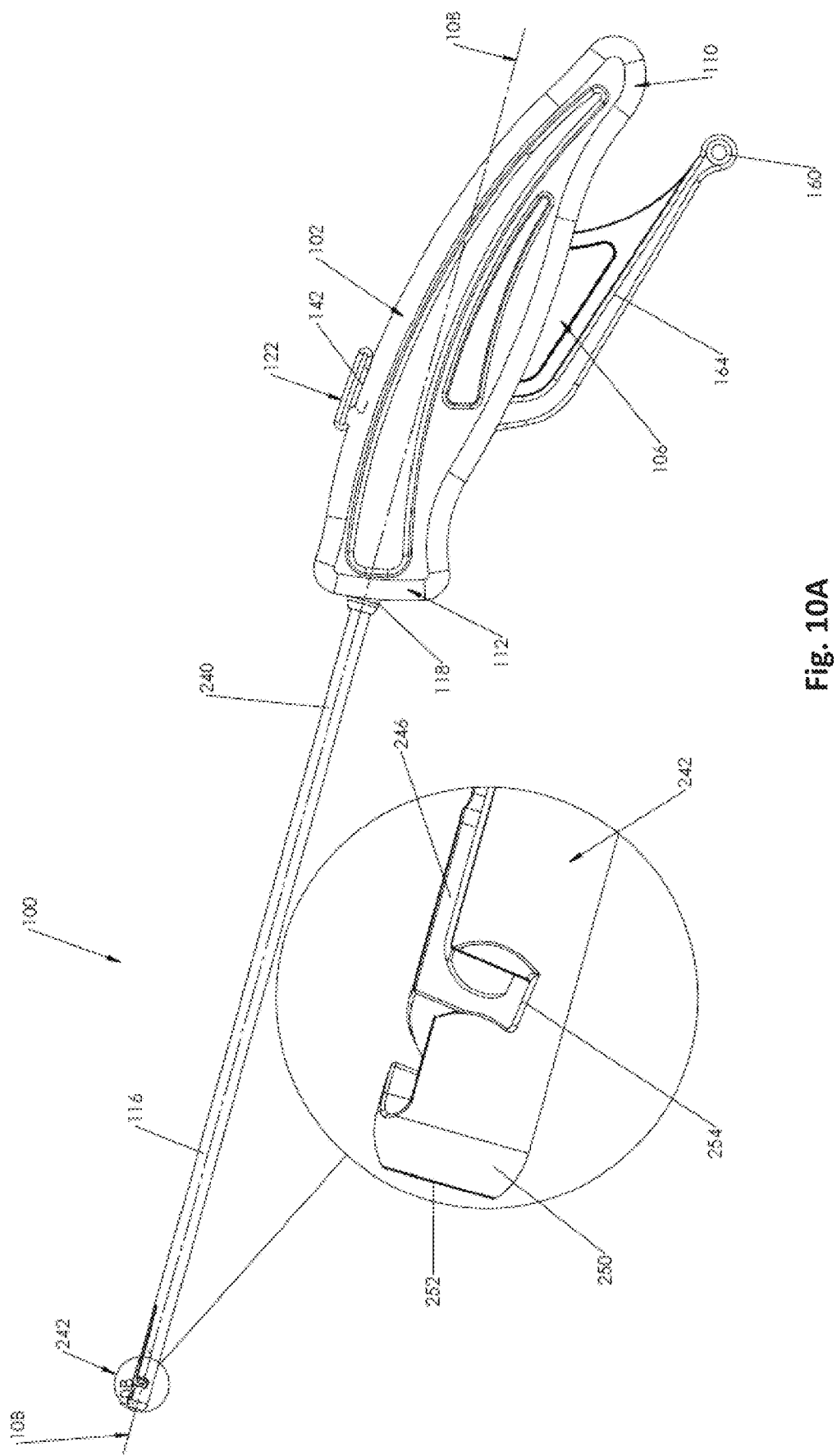
FIG. 10A is a simplified pictorial view illustration of an assembled cutting device of FIG. 1C in a partially-actuated orientation, according to some embodiments of the invention.
Figure 10B:
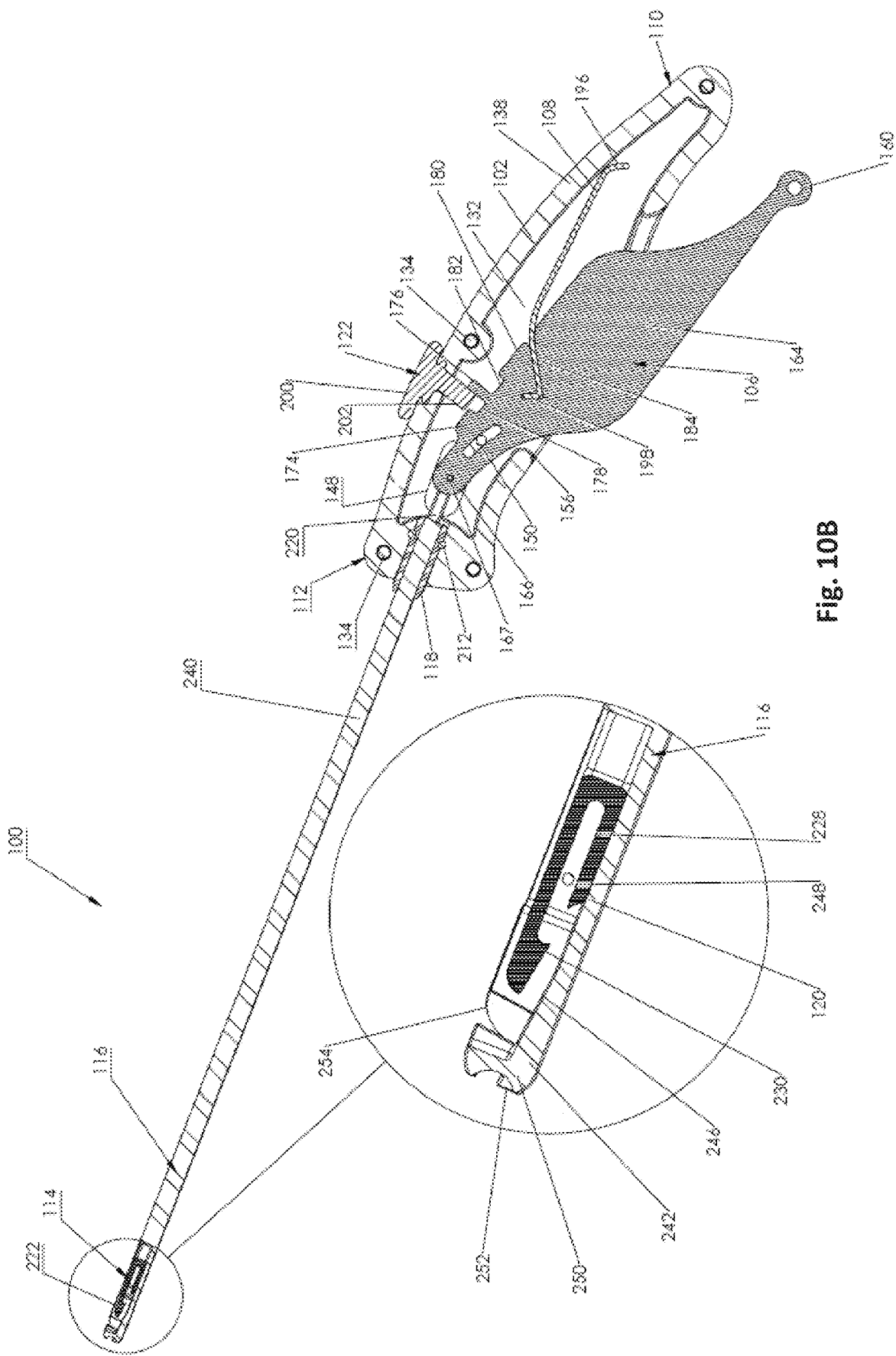
FIG. 10B is a simplified sectional illustration of the assembled cutting device of FIG. 10A in a partially-actuated orientation, according to some embodiments of the invention; section being taken along lines 10B-10B in FIG. 10A.

Reference is now made to FIG. 10A, which is a simplified pictorial view illustration of an assembled cutting device 100 of FIG. 1C in a partially-actuated orientation and to FIG. 10B, which is a simplified sectional illustration of the assembled cutting device 100 of FIG. 10A in a partially-actuated orientation, according to some embodiments of the invention, section being taken along lines 10B-10B in FIG. 10A.

According to some embodiments, the cutting device 100 is shown in a partially actuated orientation in FIGS. 10A and 10B, where the surgical suture is retained by the cutting device 100, but the cutting function is not yet enabled. In some embodiments, the lever 106 remains partially inserted into the handle element 102, such that the intermediate portion 164 of lever 106 extends through opening 156 of handle element 102. In some embodiments, connection element 108 is inserted into the L-shaped recess 184 of lever 106 and is supported against the circumferential edge 136 of handle element 102. It is appreciated that in this partially-actuated orientation, optionally, the connecting element 108 is partially deformed following pressing the lever 106 by a hand of a user.

In some embodiments, the locking button 122 remains inserted into opening 142 of the handle element 102 and the generally longitudinal protrusion 202 of locking button 122 is now inserted into recess 178 of lever 106, such that the longitudinal protrusion 202 lies distally against second protrusion 176 of lever 106.

It is a particular feature of some embodiments of the present invention that in this partially-actuated orientation, for example when the cutting device is in a retention state and the locking button 122 is locked within recess 178 of lever 106, the surgical suture is retained within the cutting device 100, but cutting of the suture is not yet enabled.

It is further seen that in some embodiments, the cylindrical element 165 of lever 106 is slidably guided within longitudinal groove 148 of handle element 102. Additionally, a connecting pin is adapted to slidably travel along longitudinal opening 172 of lever 106.

It is a particular feature of some embodiments of the present invention that a pin within groove 172 of lever 106 has moved proximally following pressing the lever 106 by the user and since the lever 106 is connected to the cutting element 114, movement of the pin within groove 172 provides for a linear movement of the cutting element 114 in a distal direction.

In some embodiments, bushing 118 remains inserted into cylindrical groove 152 of handle element using connecting pins that are inserted between recesses 154 of handle element 102 and recesses 214 of bushing 118.

It is particularly seen in FIG. 10B that the cutting element 114 is inserted through groove 166 of cylindrical element 165 and is connected thereto using a connection pin, in accordance with some embodiments of the invention. In some embodiments, the cutting element 114 is disposed within the external cylindrical element 116 and the distal end 222 of cutting element 114 is now distally displaced and spaced proximally from the distal flange 250 of the external cylindrical element 116 by a second distance, which is smaller than the first distance.

It is further seen that a connection pin that is inserted through longitudinal groove 228 of the cutting element 114 and lies proximally to the cutting edge 230 thereof, in accordance with some embodiments of the invention. In some embodiments, in this orientation, the distal end 222 of cutting element 114 partially protrudes into the diagonally extending groove 254 of external cylindrical element 116, to provide for retention of the surgical suture which is placed within the diagonally extending groove 254.

Figure 11A:
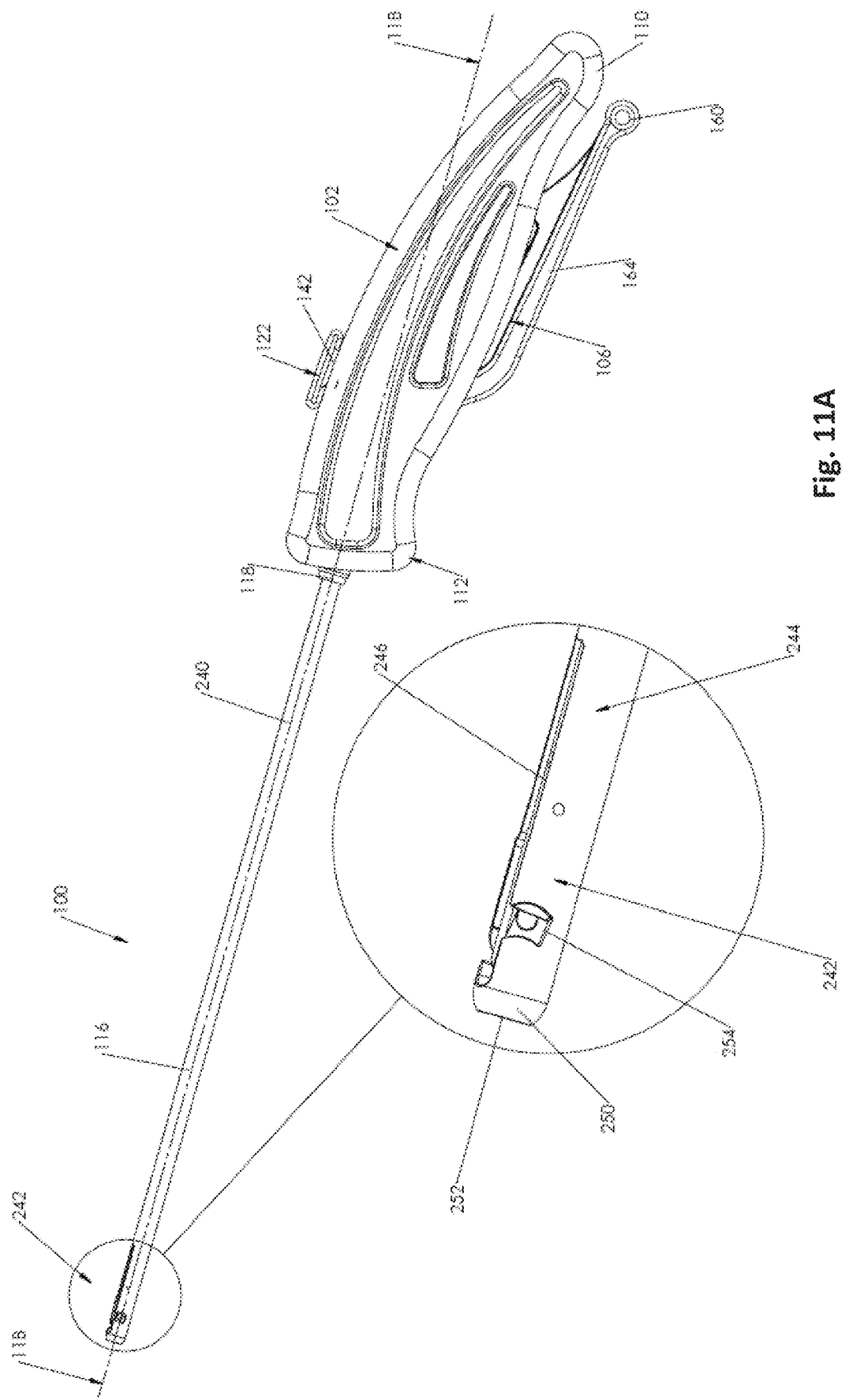
FIG. 11A is a simplified pictorial view illustration of an assembled cutting device of FIG. 1C in cutting orientation, according to some embodiments of the invention.
Figure 11B:
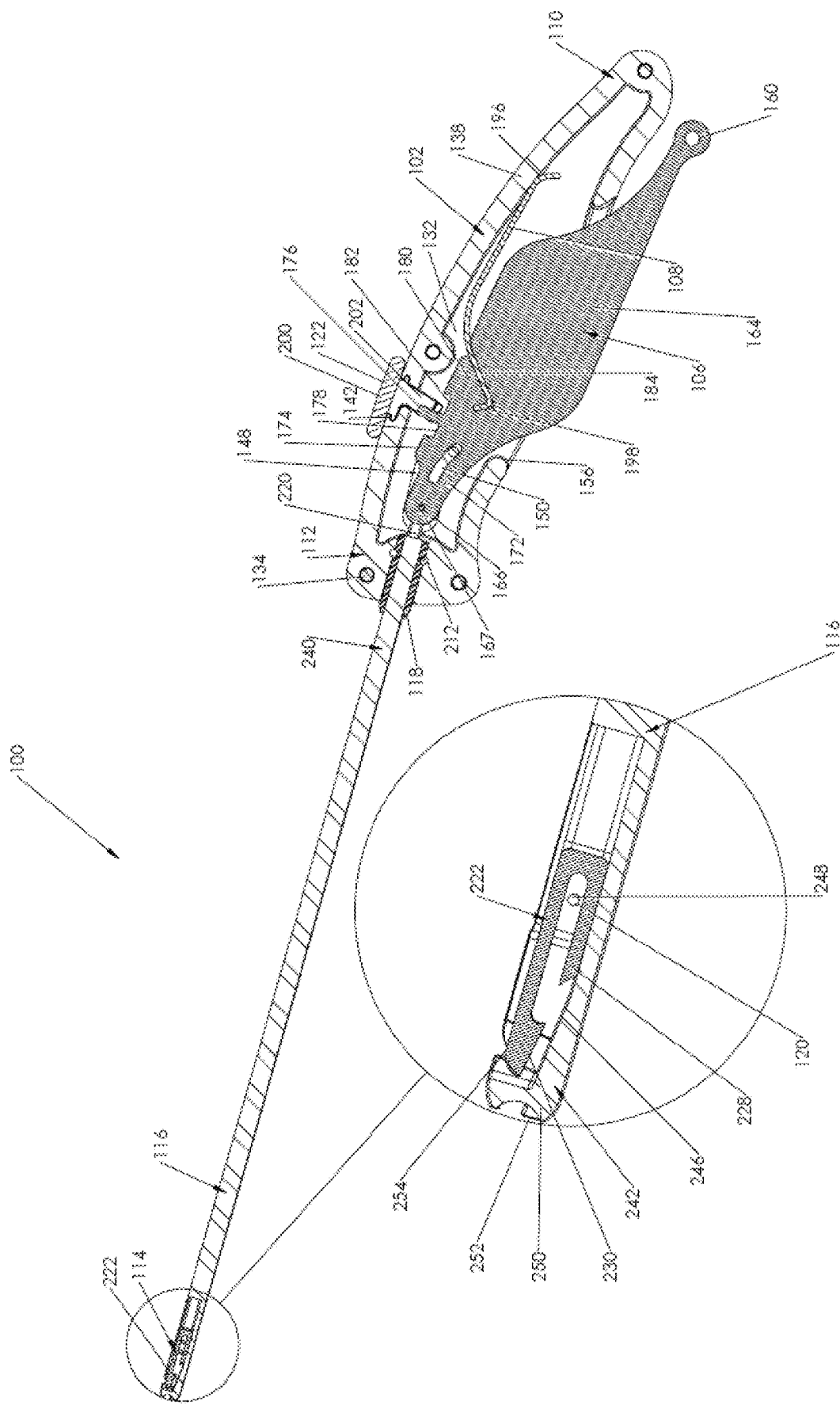
FIG. 11B is a simplified sectional illustration of the assembled cutting device of FIG. 11A in a cutting orientation, according to some embodiments of the invention; section being taken along lines 11B-11B in FIG. 11A.

Reference is now made to FIG. 11A, which is a simplified pictorial view illustration of an assembled cutting device 100 of FIG. 1C in cutting orientation and to FIG. 11B, which is a simplified sectional illustration of the assembled cutting device 100 of FIG. 11A in a cutting orientation, according to some embodiments of the invention, section being taken along lines 11B-11B in FIG. 11A.

According to some embodiments, the cutting device 100 is shown in a cutting orientation in FIGS. 11A and 11B, where the surgical suture is cut by the cutting device 100. In some embodiments, the lever 106 remains partially inserted into the handle element 102, such that the intermediate portion 164 of lever 106 extends through opening 156 of handle element 102. Additionally, connection element 108 is inserted into the L-shaped recess 184 of lever 106 and is supported against the circumferential edge 136 of handle element 102. It is appreciated that in this cutting orientation, optionally, the connecting element 108 is fully deformed following further pressing the lever 106 by a hand of a user.

It is a particular feature of some embodiments of the present invention that the locking button 122 is moved sideways in order to assume a cutting orientation.

According to some embodiments, the locking button 122 remains inserted into opening 142 of the handle element 102 and while the locking button 122 is moved sideways, the generally longitudinal protrusion 202 of locking button 122 passes through sap 177 and is now inserted into recess 182 of lever 106, such that the longitudinal protrusion 202 lies distally against third protrusion 180 of lever 106.

It is a particular feature of some embodiments of the present invention that in this cutting orientation where the locking button 122 is locked within recess 182 of lever 106, the surgical suture can be cut by the cutting element 114.

It is appreciated that in some embodiments, the connecting pin which is positioned in groove 228 of cutting element 114 provides for a minor angular movement of the distal end 222 of cutting element 114, thus allows a predetermined cutting angle.

It is further seen that in some embodiments, the cylindrical element 165 of lever 106 is slidably guided within longitudinal groove 148 of handle element 102. Additionally, a connecting pin is adapted to slidably travel along longitudinal opening 172 of lever 106.

It is a particular feature of some embodiments of the present invention that a pin within groove 172 of lever 106 has further moved proximally following further pressing the lever 106 by the user and since the lever 106 is connected to the cutting element 114, movement of the pin within groove 172 provides for a further linear movement of the cutting element 114 in a distal direction.

In some embodiments, bushing 118 remains inserted into cylindrical groove 152 of handle element using connecting pins that are inserted between recesses 154 of handle element 102 and recesses 214 of bushing 118.

It is particularly seen in FIG. 11B that in some embodiments, the cutting element 114 is inserted through groove 166 of cylindrical element 165 and is connected thereto using a connection pin. Additionally, the cutting element 114 is disposed within the external cylindrical element 116 and the distal end 222 of cutting element 114 is now further distally displaced and disposed adjacent the distal flange 250 of the external cylindrical element 116, thus enabling cutting the surgical suture positioned in the diagonally extending groove 254 of externally cylindrical element 116 by the cutting edge 230.

It is further seen that, in some embodiments, a connection pin that is inserted through longitudinal groove 228 of the cutting element 114 and lies more proximally to the cutting edge 230 thereof. Additionally, in this orientation, the distal end 222 of cutting element 114 fully protrudes into the diagonally extending groove 254 of external cylindrical element 116, for example, to provide for cutting of the surgical suture which is placed within the diagonally extending groove 254.

It is noted that, in some embodiments, the cutting edge 230 of cutting element 114 protrudes distally of the diagonally extending groove 254 of external tubular element 116 to enable cutting of the surgical suture which is retained within the diagonally extending groove 254.

Figure 12:
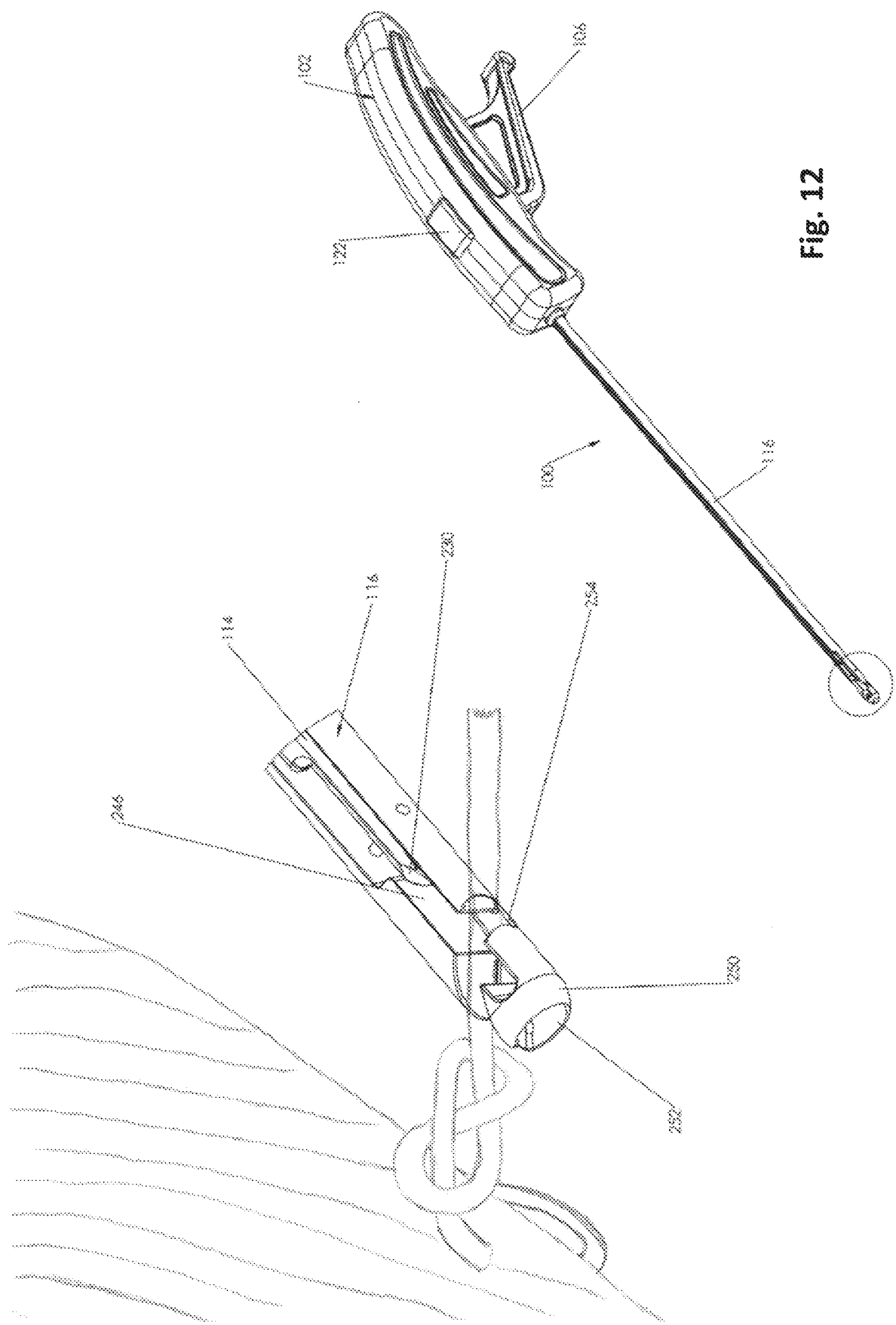
FIG. 12 is a simplified pictorial view illustration of the operation of the cutting device of FIG. 1C, shown with a surgical suture, according to some embodiments of the invention.

Reference is now made to FIG. 12, which is a simplified pictorial view illustration of the operation of the cutting device 100 of FIG. 1C, shown with a surgical suture 260, according to some embodiments of the invention.

According to some embodiments, an operative orientation, for example a cutting orientation of the cutting device 100 is seen in FIG. 12. In some embodiments, following tying a surgical suture, the suture 260 is placed within a diagonally extending groove 254 of the external cylindrical element 116. In some embodiments, once the cutting device 100 assumes a partially-activated orientation, for example a retention orientation, the cutting element 114 partially protrudes into the diagonally extending groove 254 and thus retains the surgical suture in an S-shaped manner. Further, in some embodiments, when the lever 106 is further pressed by the user and the locking button 122 is moved sideways, the cutting element 114 is optionally further advanced distally and thus the cutting edge 230 of cutting element 114 cuts the surgical suture as close as possible to the knot. In some embodiments, this proximity to the knot is provided by the fact that the suture 260 is positioned in a diagonal manner and the distance between the knot and the cutting point is minimized.

It is further noted that in some embodiments the cutting device 100 can be disposable and may be used for several times during a single procedure.

Exemplary Cutting Device Operated by Button Rotation

Figure 13:
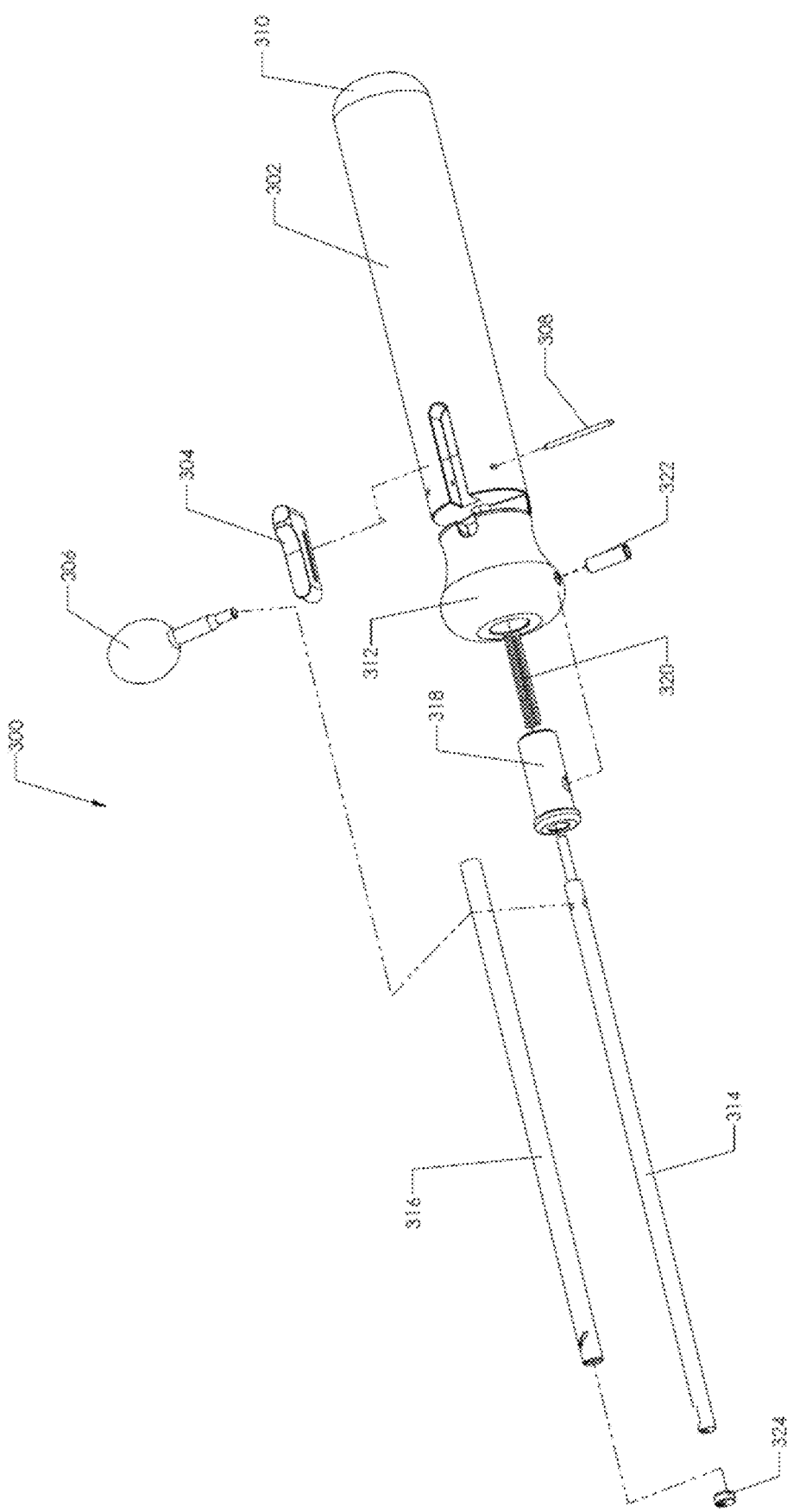
FIG. 13 is a simplified exploded view illustration of a cutting device constructed and operative, according to some embodiments of the invention.

Reference is now made to FIG. 13, depicting a simplified exploded view illustration of a cutting device 300 constructed and operative, according to some exemplary embodiments of the invention.

It is seen in FIG. 13, that in some embodiments, the cutting device 300 includes a handle 302, which is integrally made, typically from a plastic material.

According to some embodiments, partially inserted into the handle 302 is a locking button 304 and a rotating button 306, configured for operating the cutting device 300 and enable cutting orientation thereof. In some embodiments, the locking button 304 is slidably connected to handle 302 by means of a connecting pin 308.

It is seen in FIG. 13 that in some embodiments, the handle 302 has a proximal end 310 and a distal end 312. In some embodiments, an internal cutting element 314, which is enclosed within an external cutting element 316 is partially inserted into the distal end 312 of handle 302 by means of a bushing 318. Additionally, the internal element 314 is attached to the rotating button 306 and a biasing element 320, optionally in a form of a coil spring, is disposed within the handle 302, between the handle and internal cutting element 314. In some embodiments, the bushing 318 is connected to the handle 302 by means of connecting pin 322.

It is further seen in FIG. 13 that in some embodiments, the external cutting element 316 is fixedly connected to bushing 318 and aligning element 324 is fixedly connected to external cutting element 316.

According to some embodiments, a locking button 304 is partially disposed within handle 302 and configured to lock the cutting device 300 in the partially-activated orientation, for example in a retention orientation.

Figure 14A:
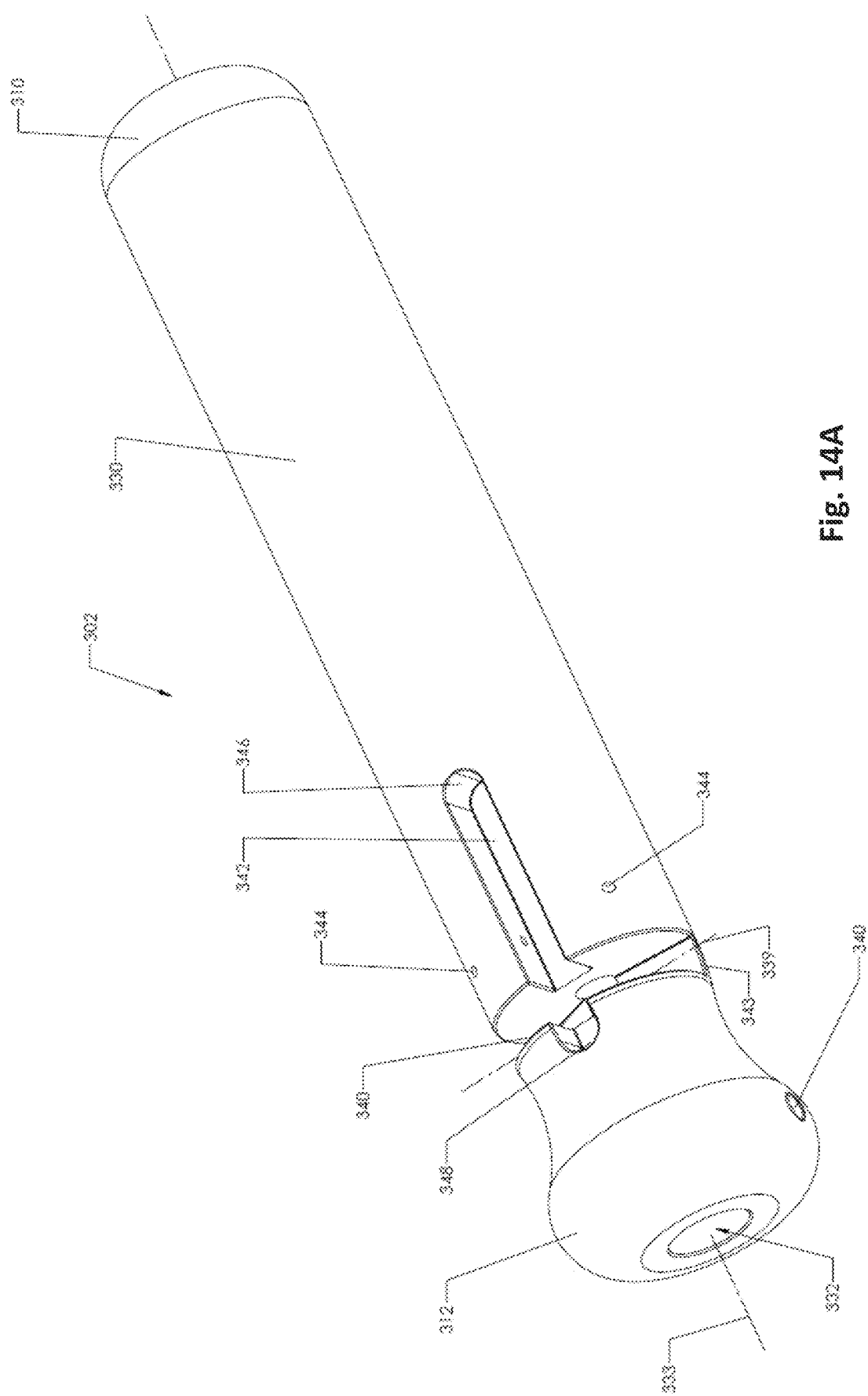

Reference is now made to FIGS. 14A-14C, which are simplified respective pictorial view, elevation view and section view illustrations of the handle 302 of cutting device 300 of FIG. 13, according to some embodiments of the invention. FIG. 14C is taken along lines 14C-14C in FIG. 14B.

It is appreciated that any form of handle 302 can be used for the cutting device 300 in accordance with some embodiments of the present invention. In some embodiments, handle 302 has a proximal end 310 and a distal end 312 and an outer surface 330.

As specifically seen in FIG. 14C, in some embodiments, there is an internal recess 332 formed in the distal end 312 of handle 302 and extends along a longitudinal axis 333. In some embodiments, internal recess 332 has a distal generally cylindrical portion 334 of a first diameter and a proximal generally cylindrical portion 336 of a second diameter, which is smaller than the first diameter. Optionally, proximal portion 336 of internal recess 332 terminates at a distally facing wall 338.

It is further seen that in some embodiments, a through bore 340 is formed at the distal end 312 of handle 302 for insertion of connecting pin 322 therein, and extends transversely to longitudinal axis 333, along axis 339.

It is further seen in FIGS. 14B and 14C that in some embodiments, a first groove 340 is formed proximally to distal end 312 of handle 302 and extends along axis 339 for at least partial insertion of the rotating button 306 therein. It is appreciated that optionally, first groove 340 extends internally such that it partially intersects with the proximal portion 336 of internal recess 332. In some embodiments, the first groove 340 defines a first edge 341 and a second edge 343.

It is additionally seen in FIGS. 14B and 14C that according to some exemplary embodiments, a second generally longitudinal groove 342 is formed proximally to distal end 312 of handle 302 and extends along longitudinal axis 333, which is disposed transversely to axis 339 for at least partial insertion of the locking button 304 therein. It is appreciated that in some embodiments, second generally longitudinal groove 342 extends internally such that it partially intersects with the first groove 340. In some embodiments, the second groove 342 defines a proximal curved wall 346 and a distal curved wall 348.

It is further seen that in some embodiments, a through bore 344 is formed distally of first groove 340 and adjacent thereto for insertion of connecting pin 308 therein, and extends transversely to longitudinal axis 333, along an axis parallel to axis 339.

Reference is now made to FIG. 15, which is a simplified pictorial view illustration of locking button 304, which is configured to be partially inserted into the handle 302 of FIGS. 14A-14C, according to some embodiments of the invention.

In some embodiments, the locking button 304 has a proximal end 350, a distal end 352 and an intermediate grasping portion 354. Grasping portion 354 optionally includes a protrusion for easier grasping by a finger of a user. In some embodiments, locking button 304 has a first side wall 356 and a second side wall 358. Additionally, a generally longitudinal groove 360 extends from first side wall 356 to second side wall 358 and defines a proximal curved wall 362 adjacent proximal end 350 of locking button 304 and a distal curved wall 364 adjacent distal end 352 of locking button 304.

Figure 16:
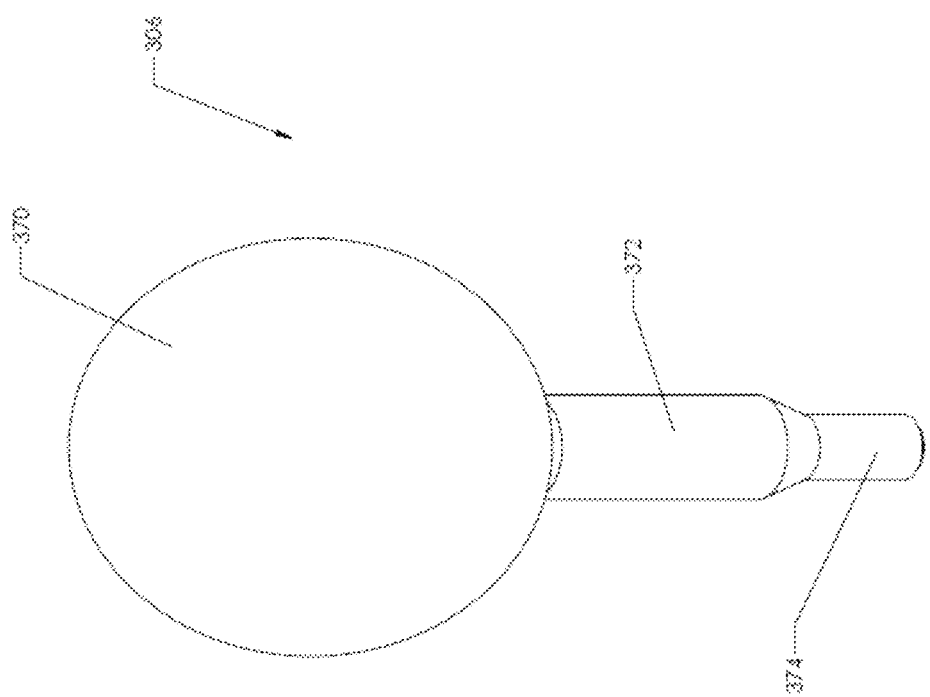
FIG. 16 is a simplified pictorial view illustration of a rotating button, which is configured to be partially inserted into the handle of FIGS. 14A-14C, according to some embodiments of the invention.

Reference is now made to FIG. 16, which is a simplified pictorial view illustration of rotating button 306, which is configured to be partially inserted into handle 302 of FIGS. 14A-14C, according to some embodiments of the invention.

It is seen in FIG. 16 that the rotating button 306 has a gripping portion 370, which is spherical in accordance with some embodiments of the present invention, but can alternatively be of any other shape. In some embodiments, rotating button 306 additionally has an intermediate generally cylindrical portion 372 of a first diameter and a connecting generally cylindrical longitudinal portion 374 of a second diameter, which is optionally smaller than the first diameter for connection with internal cutting element 314.

Figure 17A:
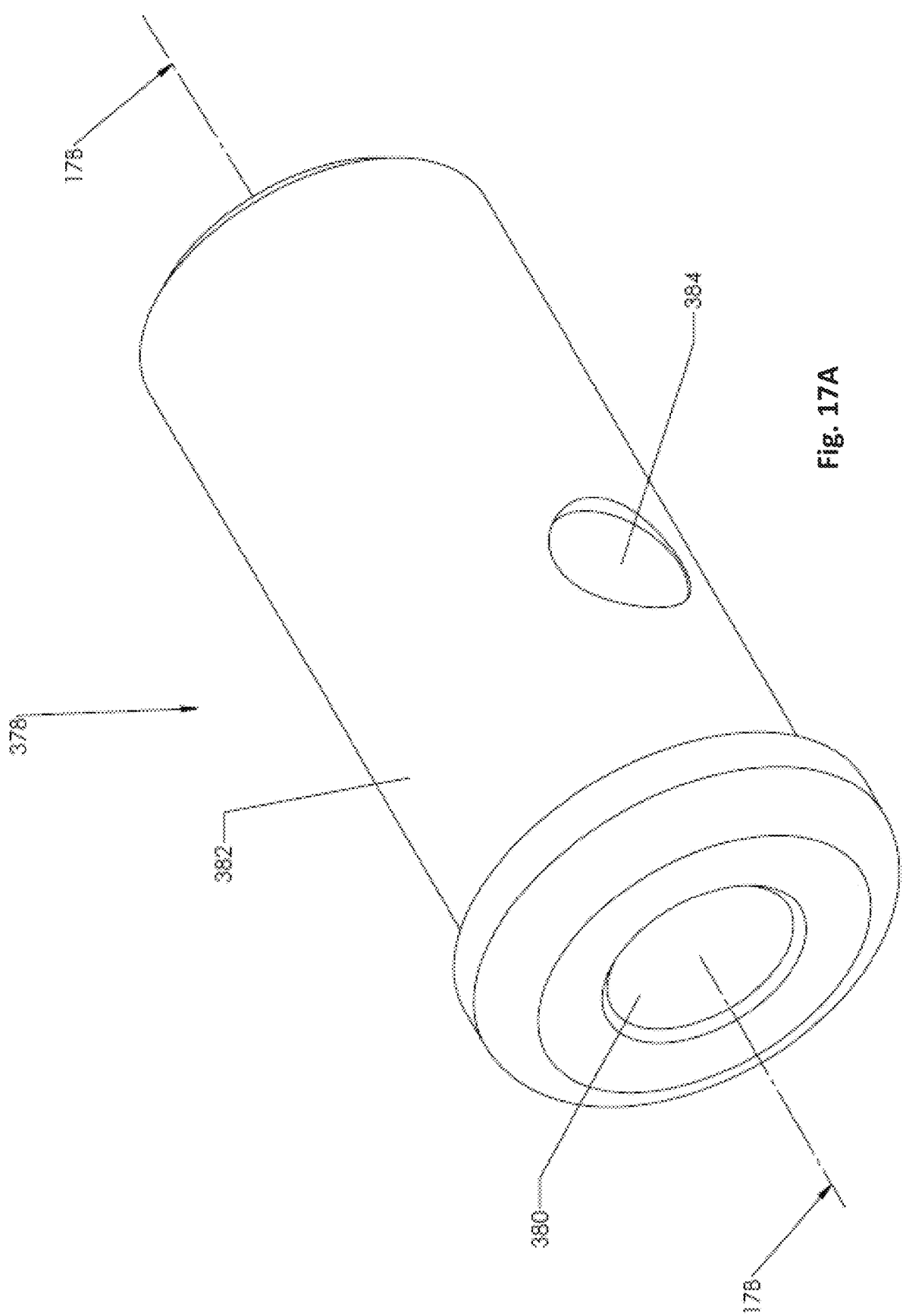
FIGS. 17A and 17B are simplified respective pictorial view and sectional view illustration of a bushing of the cutting device of FIG. 13, according to some embodiments of the invention.
Figure 17B:
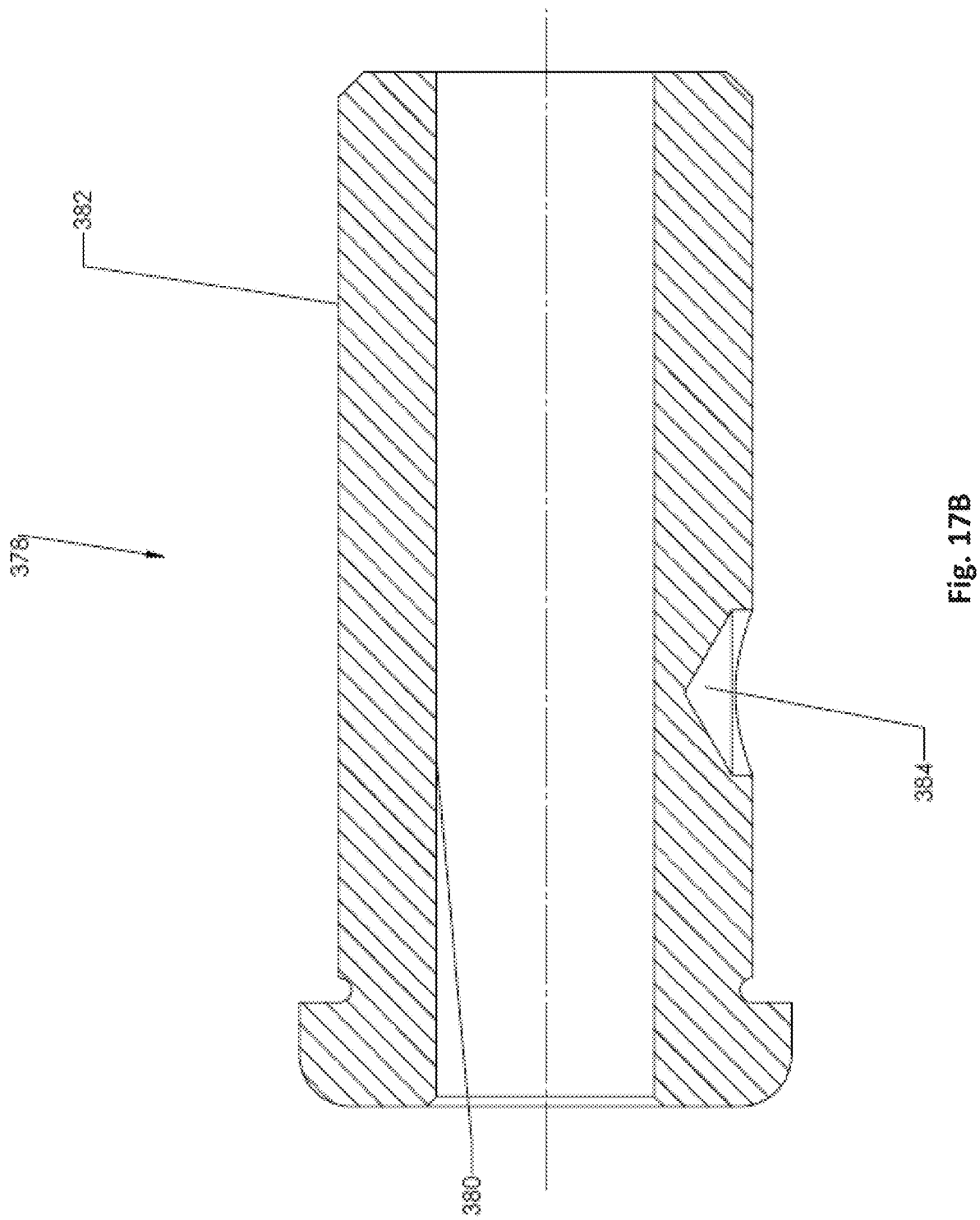

Reference is now made to FIGS. 17A and 17B, which are simplified respective pictorial view and sectional view illustrations of bushing 318 of the cutting device 300 of FIG. 13, according to some embodiments of the invention. FIG. 17B is taken along lines 17B-17B in FIG. 17A.

In some embodiments, bushing 318 is a generally cylindrical hollow element having an inner surface 380 and an outer surface 382. In some embodiments, a recess 384 is formed on the outer surface 382 of bushing 318 for engagement with connection pin 322.

Figure 18:
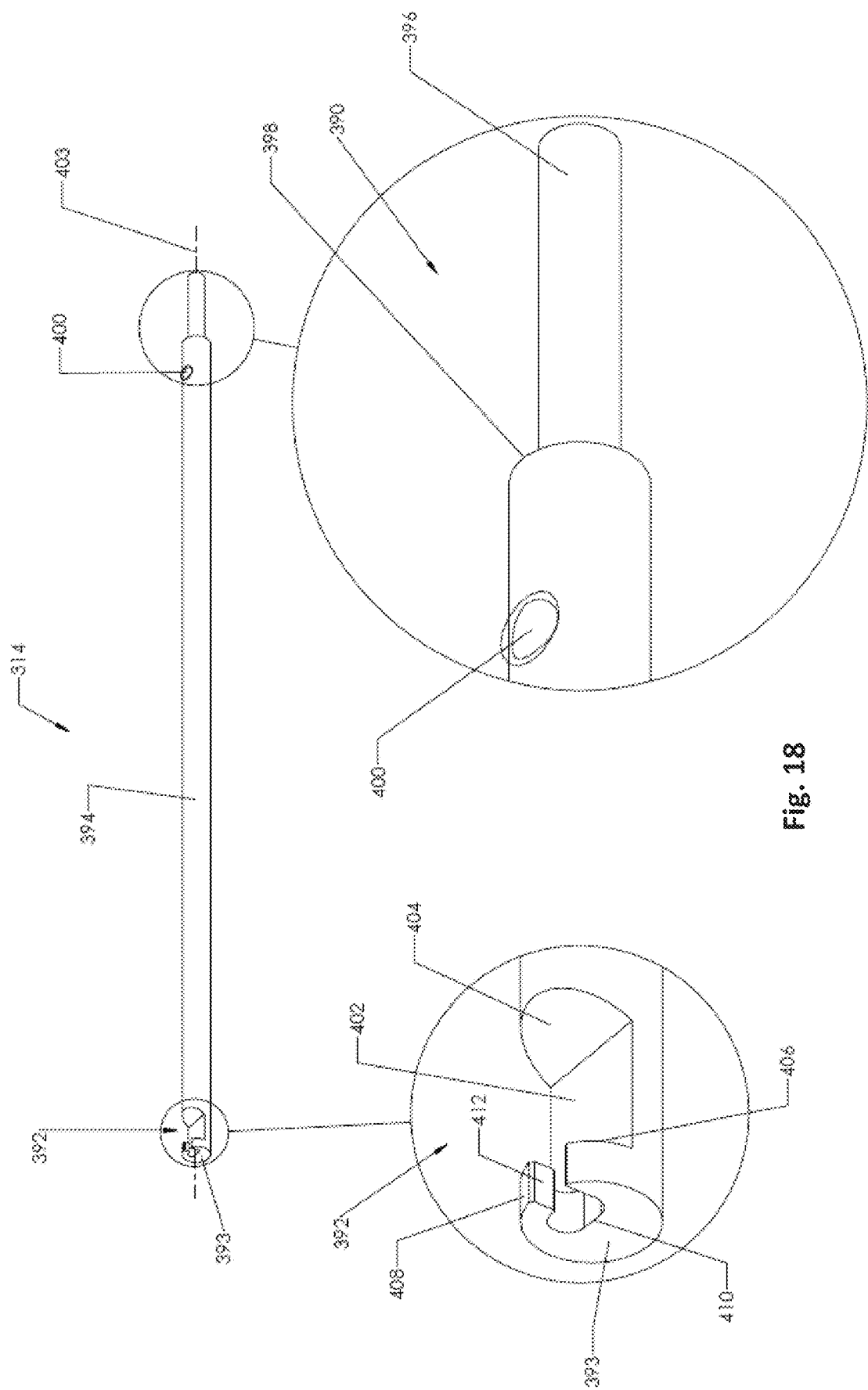
FIG. 18 is a simplified pictorial view illustration of an internal cutting element of the cutting device of FIG. 13 and partial enlargements thereof, according to some embodiments of the invention.

Reference is now made to FIG. 18, which is a simplified pictorial view illustration of the internal cutting element 314 of the cutting device 300 of FIG. 13 and partial enlargements thereof, according to some embodiments of the invention.

In some embodiments, the internal cutting element 314 has a proximal end 390, a distal end 392 having a distalmost wall surface 393 and an intermediate portion 394. In some embodiments, the cutting element 314 is an integrally formed longitudinal element, optionally made of metal.

According to some embodiments, the internal cutting element 314 is a generally cylindrical element of a first diameter having at its proximal end 390 a cylindrical shaft 396 of a second diameter, which is optionally smaller than the first diameter. In some embodiments, a proximally facing shoulder 398 is formed between the intermediate portion 394 and the cylindrical shaft 396.

According to some embodiments, there is a through bore 400 formed adjacent the cylindrical shaft 396, for example, for partial insertion of the rotating button 306 therethrough for allowing rotation of the internal cutting element 314.

It is additionally seen in FIG. 18 that in some embodiments, a recess 402 is formed in the distal end 392 of internal cutting element 314, adjacent the distalmost wall surface 393. In some embodiments, recess 402 is generally longitudinal extending along longitudinal axis 403 and defines a generally tapered distally facing wall 404 and a proximally facing wall 406. Optionally, the recess extends internally into the internal cutting element 314. In some embodiments, the recess 402 forms a distal flange 408.

In some embodiments, an opening 410 is formed within distal flange 408, which extends along a portion of flange 408 and forms a gap 412 at its circumference, for example, for insertion of a surgical suture therethrough.

Figure 19:
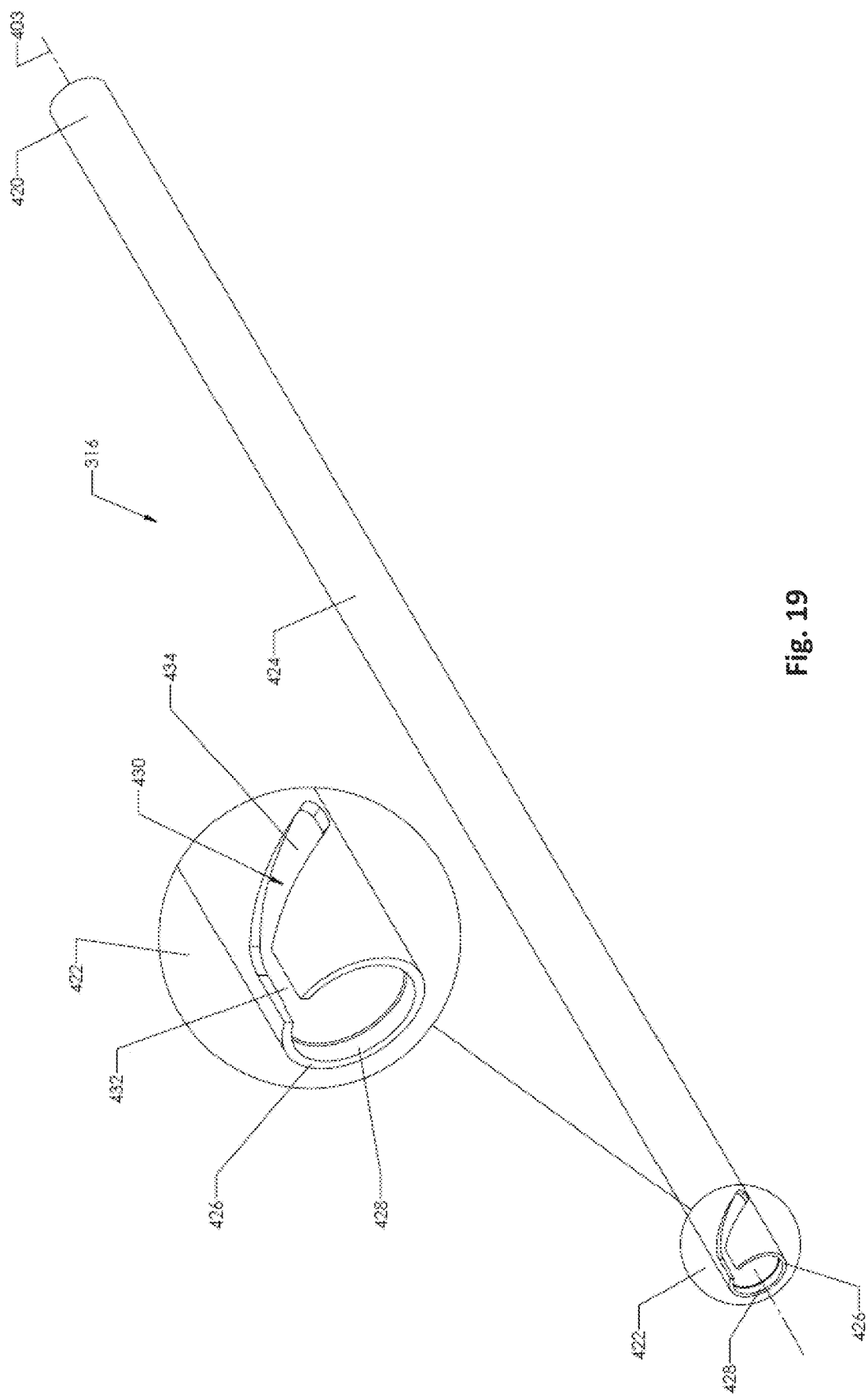
FIG. 19 is a simplified pictorial view illustration of an external cutting element of the cutting device of FIG. 13 and partial enlargements thereof, according to some embodiments of the invention.

Reference is now made to FIG. 19, which is a simplified pictorial view illustration of an external cutting element 316 of the cutting device 300 of FIG. 13 and partial enlargements thereof, according to some embodiments of the invention.

According to some embodiments, the external tubular element 316 has a proximal end 420, a distal end 422 and an intermediate portion 424. In some embodiments, the external tubular element 316 is an integrally formed longitudinal hollow element, optionally made of metal.

It is seen in FIG. 19 that in some embodiments, the distal end 422 has a distal circumferential edge 426. In some embodiments, an annular recess 428 extends slightly proximally from distal circumferential edge 426, for example, for partial insertion of the aligning element 324 therein.

According to some exemplary embodiments, a spirally shaped groove 430 is formed at the distal end 422 of external cutting element 316, extending slightly proximally from the distal circumferential edge 426. In some embodiments, the spirally shaped groove 430 includes a distal portion 432 which extends generally proximally longitudinally along axis 403 and a diagonally extending portion 434 extending from distal portion 432. Optionally, the spirally shaped groove 430 is adapted for insertion of a surgical suture therein.

Figure 20:
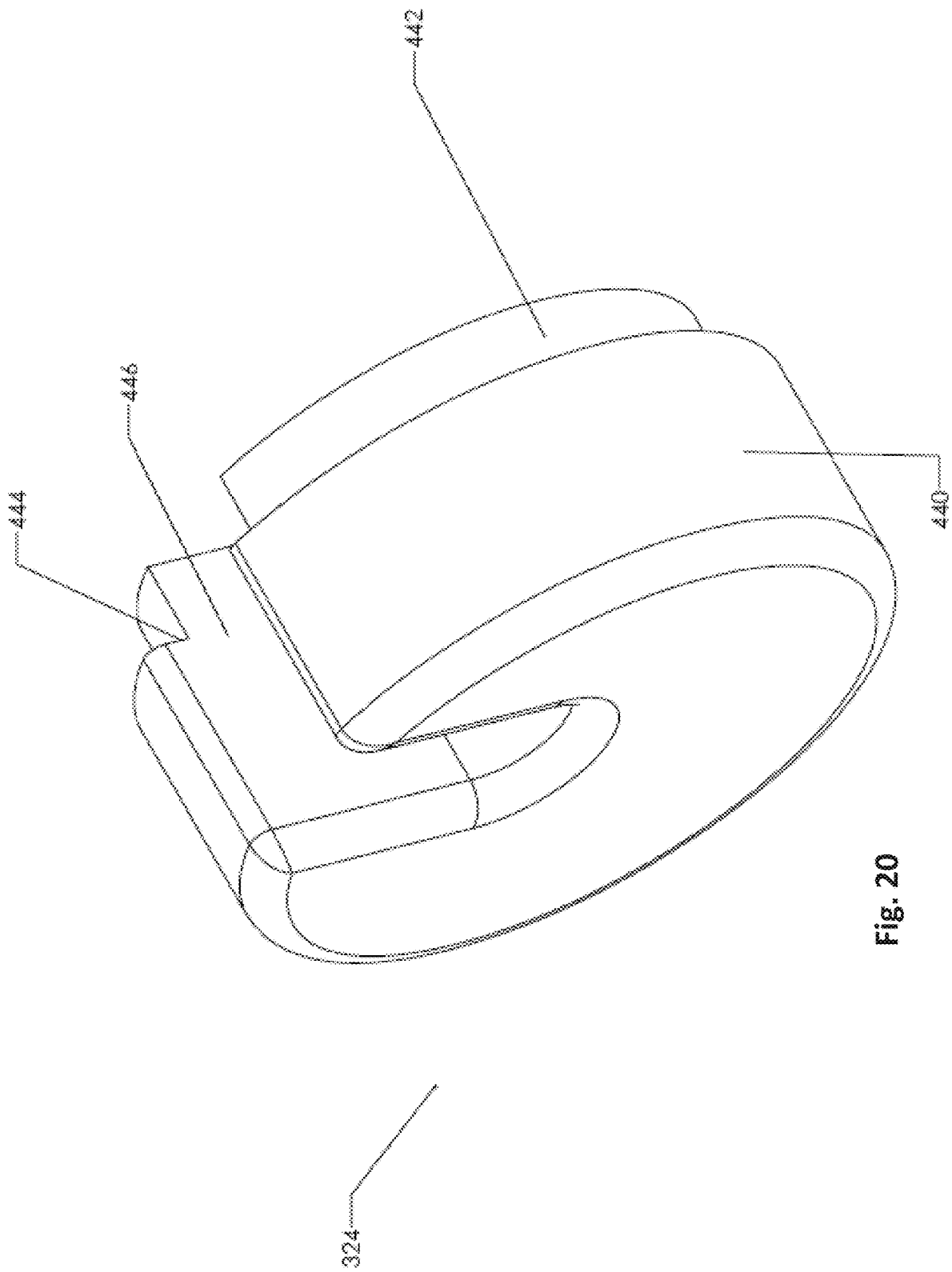
FIG. 20 is a simplified pictorial view illustration of an aligning element of the cutting device of FIG. 13, according to some embodiments of the invention.

Reference is now made to FIG. 20, which is a simplified pictorial view illustration of aligning element 324 of the cutting device 300 of FIG. 13, according to some embodiments of the invention.

According to some exemplary embodiments, the aligning element 324 is a generally annular element having a distal portion 440 of a first diameter and a proximal portion 442 of a second diameter, which is generally smaller than the first diameter. In some embodiments, a proximally facing shoulder 444 is defined between the distal portion 440 and the proximal portion 442.

Optionally, a U-shaped opening 446 is formed through distal portion 440 and proximal portion 442 for insertion of surgical suture therethrough.

Figure 21B:
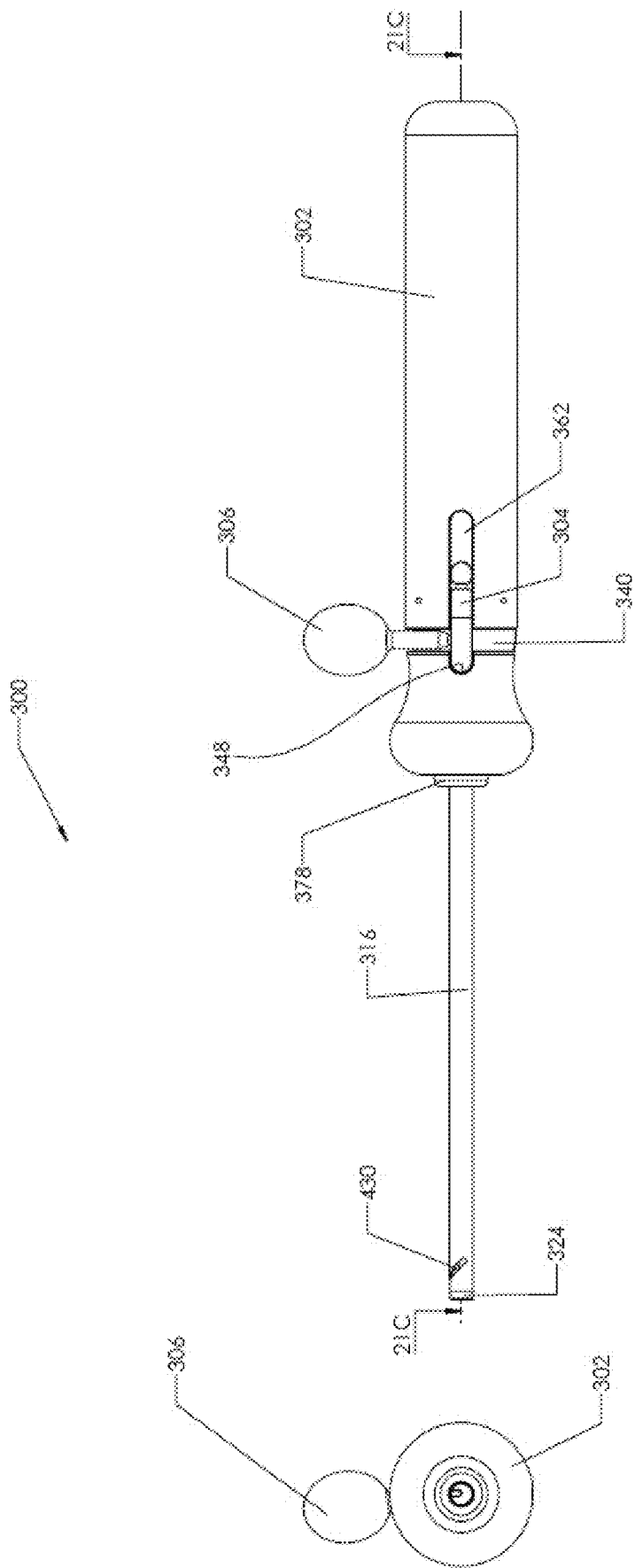
Figure 21C:
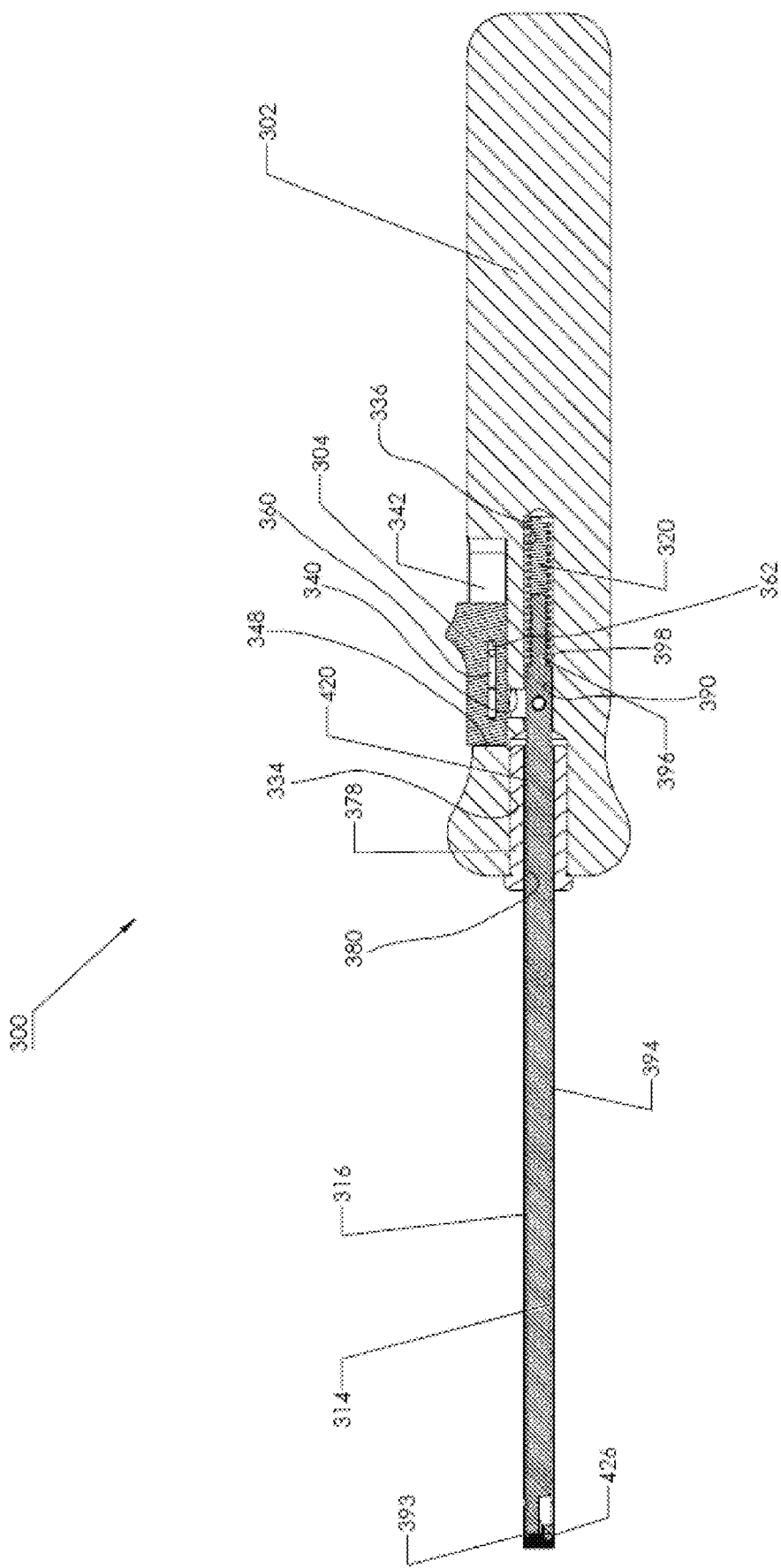
FIG. 21C is a simplified sectional illustration of the assembled cutting device of FIG. 21A in a non-actuated orientation, according to some embodiments of the invention; section being taken along lines 21C-21C in FIG. 21B.

Reference is now made to FIGS. 21A and 21B, which are simplified respective pictorial view and elevation view illustrations of an assembled cutting device 300 of FIG. 13 in a non-actuated orientation and to FIG. 21C, which is a simplified sectional illustration of the assembled cutting device 300 of FIG. 21A in a non-actuated orientation, according to some embodiments of the invention. Section being taken along lines 21C-21C in FIG. 21B.

It is a particular feature of some embodiments of the present invention that cutting device 300 can be introduced through the same portal of the surgical suture and the use of an additional portal is obviated due to the particular structure of cutting device 300, which receives the surgical suture within spirally shaped groove 430.

According to some exemplary embodiments, the cutting device 300 is shown in non-actuated orientation, in FIGS. 21A-21C. In some embodiments, the internal and external cutting elements 314 and 316 are arranged along a mutual longitudinal axis 403. In some embodiments, the internal cutting element 314 is inserted within the external cutting element 316 and aligning element 324 is fixedly attached to the external cutting element 316, such that proximal portion 442 of aligning element 324 lies within annular recess 428 of external cutting element 316. Additionally, the U-shaped opening 446 of aligning element 324 is aligned with the distal portion 432 of spirally-shaped groove 430 of external cutting element 316 and further aligned with gap 412 of internal cutting element 314.

According to some exemplary embodiments, proximal end 420 of external cutting element 316 is inserted into the interior of bushing 378 and lies against inner surface 380 thereof. In some embodiments, the bushing 378 is fixedly held within the distal cylindrical portion 334 of internal recess 332 of handle 302 by means of connecting pin 322 that engages recess 384 of bushing 378.

It is a particular feature of some embodiments of the present invention that distalmost wall surface 393 of internal cutting element 314 is coplanar with distal circumferential edge 426 of external cutting element 316.

According to some embodiments, the proximal end 390 of internal cutting element 314 protrudes proximally from the proximal end 420 of external cutting element 316, such that the proximal part of intermediate portion 394 and cylindrical shaft 396 is inserted within proximal cylindrical portion 336 of internal recess 332 of handle 302 and biasing element 320 is also inserted within proximal cylindrical portion 336 of handle 302 and encircles cylindrical shaft 396 of internal cutting element 314.

It is a particular feature of some embodiments of the present invention that the biasing element 320 exerts constant force on proximally facing shoulder 398 of internal cutting element 314 in order to assure that the distalmost wall surface 393 of internal cutting element 314 is coplanar with distal circumferential edge 426 of external cutting element 316 for enabling cutting of a surgical suture that is placed within the spirally-shaped groove 430 of external cutting element 316.

It is further seen in FIGS. 21A-21C that in some embodiments of the invention, intermediate cylindrical portion 372 of rotating button 306 is disposed within through bore 340 of handle 302 and cylindrical longitudinal portion 374 of rotating button 306 is inserted into through bore 400 of internal cutting element 314.

It is seen in FIGS. 21A-21C that in some embodiments, the rotating button 306 is disposed adjacent the first edge 341 of through bore 340 of handle 302 in the non-actuated position.

In some embodiments, locking button 304 is positioned within second longitudinal groove 342 of handle 302 adjacent distal curved wall 348 of second longitudinal groove 342 of handle 302. Additionally, locking button 304 is slidably connected to handle 302 by means of connecting pin 308, which is inserted into longitudinal groove 360 of locking button 304. In some embodiments, the connecting pin 308 is positioned adjacent proximal curved wall 362 of longitudinal groove 360 in the non-actuated orientation.

It is a particular feature of some embodiments of the present invention that in this non-actuated orientation gap 412 of opening 410 of internal cutting element 314 is aligned with the spirally-shaped groove 430 of external cutting element 316 and with opening 446 of aligning element 324, thus surgical suture can be placed within spirally-shaped groove 430, as specifically seen in FIG. 21A.

Figure 22A:
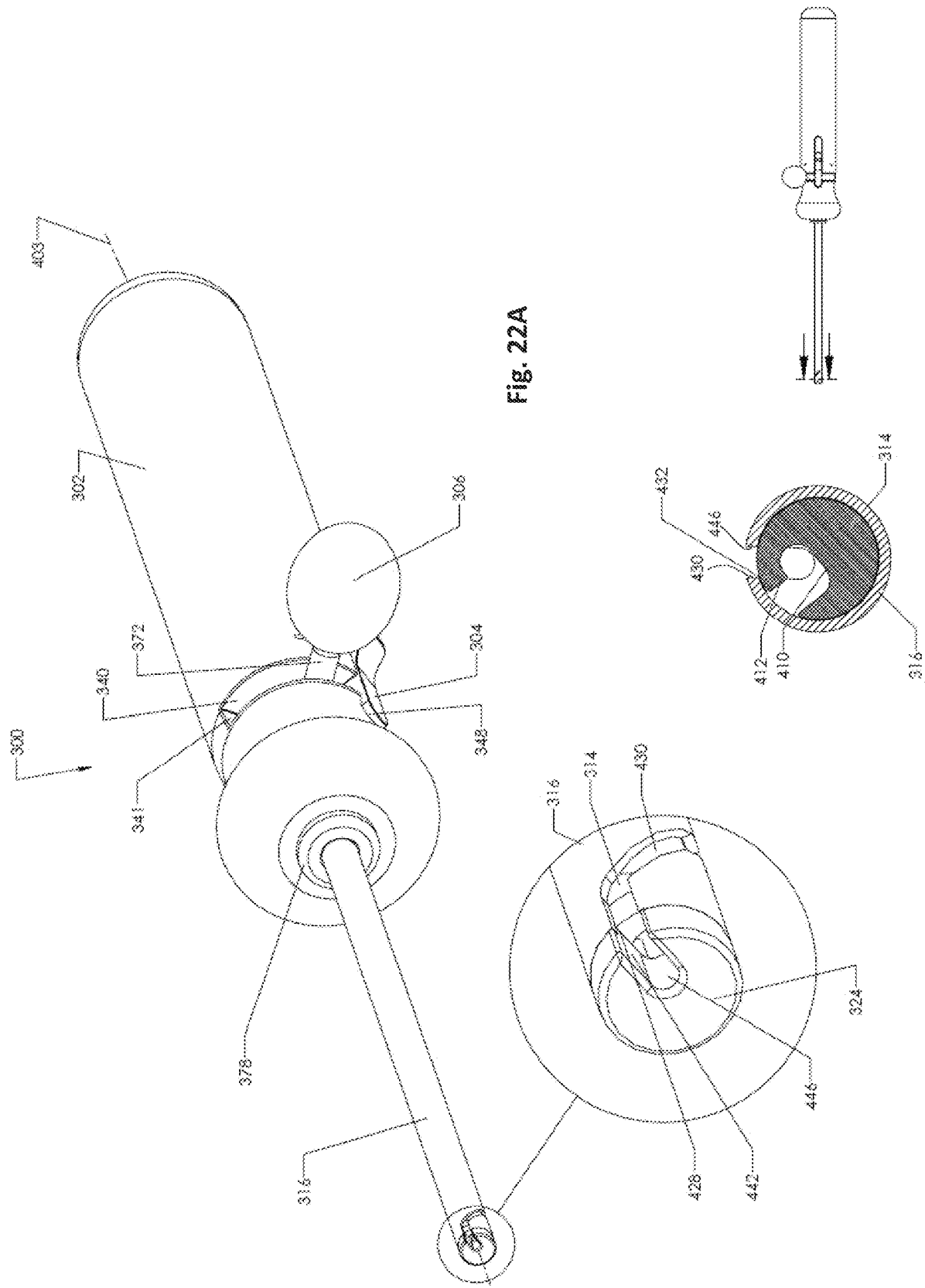
FIGS. 22A and 22B are simplified respective pictorial view and elevation view illustrations of an assembled cutting device of FIG. 13 in a partially-actuated orientation, according to some embodiments of the invention.
Figure 22B:
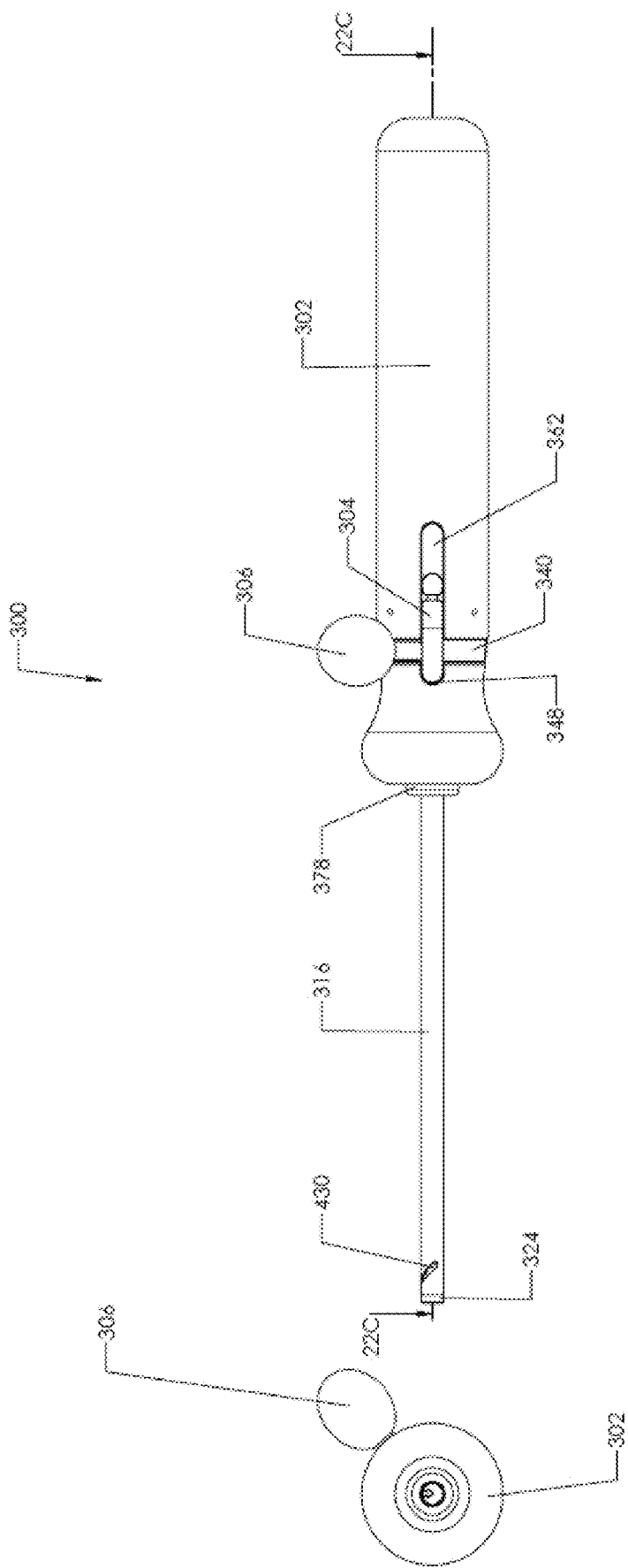
Figure 22C:
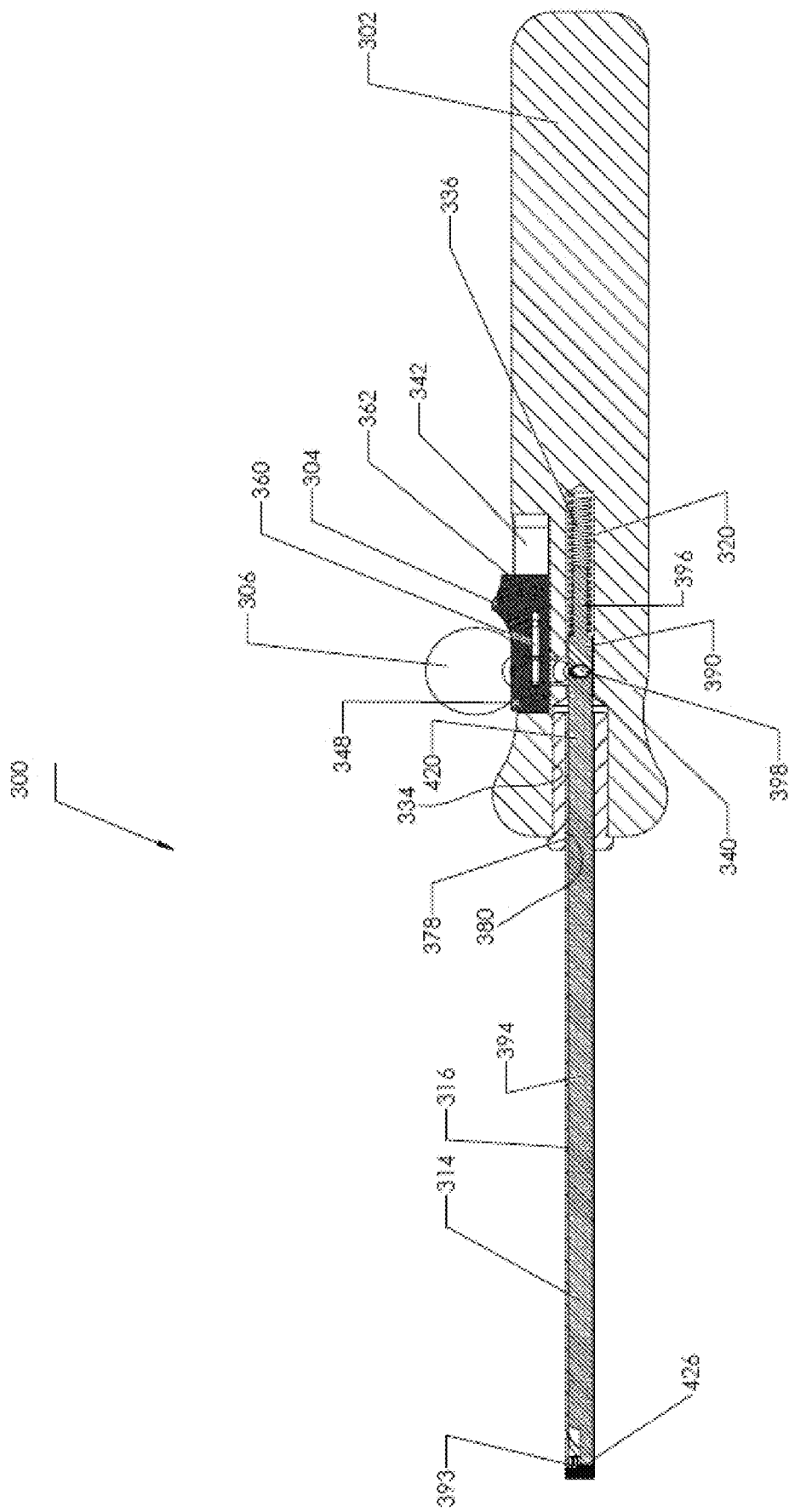
FIG. 22C is a simplified sectional illustration of the assembled cutting device of FIG. 22A in a partially-actuated orientation, according to some embodiments of the invention; section being taken along lines 22C-22C in FIG. 22B.

Reference is now made to FIGS. 22A and 22B, which are simplified respective pictorial view and elevation view illustrations of the assembled cutting device 300 of FIG. 13 in a partially-actuated orientation, and to FIG. 22C, which is a simplified sectional illustration of the assembled cutting device 300 of FIG. 22A in a partially-actuated orientation, according to some embodiments of the invention. Section being taken along lines 22C-22C in FIG. 22B.

According to some exemplary embodiments, the cutting device 300 is shown in partially-actuated orientation, for example in retention orientation, in FIGS. 22A-22C. In some embodiments, the internal and external cutting elements 314 and 316 are arranged along a mutual longitudinal axis 403. Additionally, the internal cutting element 314 is inserted within the external cutting element 316 and aligning element 324 is fixedly attached to the external cutting element 316, such that proximal portion 442 of aligning element 324 lies within annular recess 428 of external cutting element 316. In some embodiments, the U-shaped opening 446 of aligning element 324 remains aligned with the distal portion 432 of spirally-shaped groove 430 of external cutting element 316, however it is only partially aligned with opening 410 of internal cutting element 314 in this partially-actuated orientation.

According to some embodiments, proximal end 420 of external cutting element 316 remains inserted into the interior of bushing 378 and lies against inner surface 380 thereof. In some embodiments, the bushing 378 is fixedly held within the distal cylindrical portion 334 of internal recess 332 of handle 302 by means of connecting pin 322 that engages recess 384 of bushing 378.

It is a particular feature of some embodiments of the present invention that distalmost wall surface 393 of internal cutting element 314 is coplanar with distal circumferential edge 426 of external cutting element 316.

In some embodiments, the proximal end 390 of internal cutting element 314 protrudes proximally from the proximal end 420 of external cutting element 316, such that the proximal part of intermediate portion 394 and cylindrical shaft 396 is inserted within proximal cylindrical portion 336 of internal recess 332 of handle 302 and biasing element 320 is also inserted within proximal cylindrical portion 336 of handle 302 and encircles cylindrical shaft 396 of internal cutting element 314.

It is a particular feature of some embodiments of the present invention that the biasing element 320 exerts constant force on proximally facing shoulder 398 of internal cutting element 314 in order to assure that the distalmost wall surface 393 of internal cutting element 314 is coplanar with distal circumferential edge 426 of external cutting element 316 for enabling cutting of a surgical suture that is placed within the spirally-shaped groove 430 of external cutting element 316.

It is further seen in FIGS. 22A-22C that in some embodiments, intermediate cylindrical portion 372 of rotating button 306 is disposed within through bore 340 of handle 302 and cylindrical longitudinal portion 374 of rotating button 306 is inserted into through bore 400 of internal cutting element 314.

It is seen in FIGS. 22A-22C that in some embodiments, the rotating button 306 is spaced from the first edge 341 of through bore 340 of handle 302 and is disposed in the middle of through bore 340 in the partially-actuated orientation.

According to some embodiments, locking button 304 is positioned within second longitudinal groove 342 of handle 302 adjacent distal curved wall 348 of second longitudinal groove 342 of handle 302. Optionally, locking button 304 is slidably connected to handle 302 by means of connecting pin 308, which is inserted into longitudinal groove 360 of locking button 304. In some embodiments, the connecting pin 308 is positioned adjacent proximal curved wall 362 of longitudinal groove 360 in the partially-actuated orientation.

It is a particular feature of some embodiments of the present invention that the locking button 304 blocks further rotation of the rotating button 306 towards second edge 342 of through bore 340 of handle 302, thus prevents cutting of the surgical suture.

It is a further particular feature of some embodiments of the present invention that in this partially-actuated orientation gap 412 of opening 410 of internal cutting element 114 is rotated using the rotating button 306 and is now not aligned with the spirally-shaped groove 430 of external cutting element 316 and opening 446 of aligning element 324. In some embodiments, in this rotational position of the internal cutting element 314 spirally-shaped groove 430 of external cutting element 316 and opening 446 of aligning element 324 partially overlap with opening 410 of internal cutting element 314, thus creating an opening between the internal cutting element 314 and external cutting element 316 which is optionally, substantially identical in diameter to the diameter of a surgical suture, thus the surgical suture can be retained within the cutting device 300, but cutting is not enabled yet.

Figure 23A:
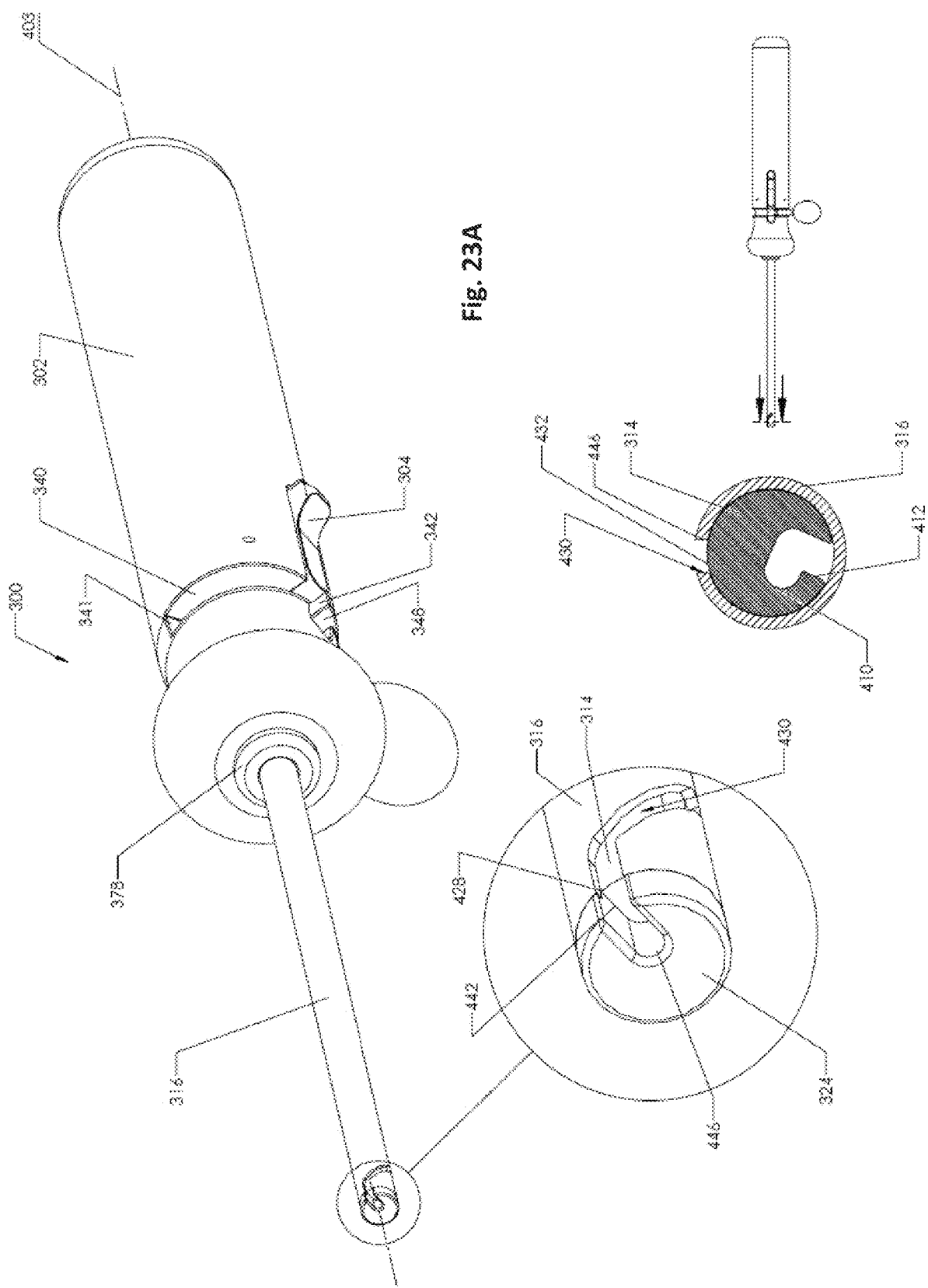
FIGS. 23A and 23B are simplified respective pictorial view and elevation view illustrations of an assembled cutting device of FIG. 13 in cutting orientation; according to some embodiments of the invention.
Figure 23B:
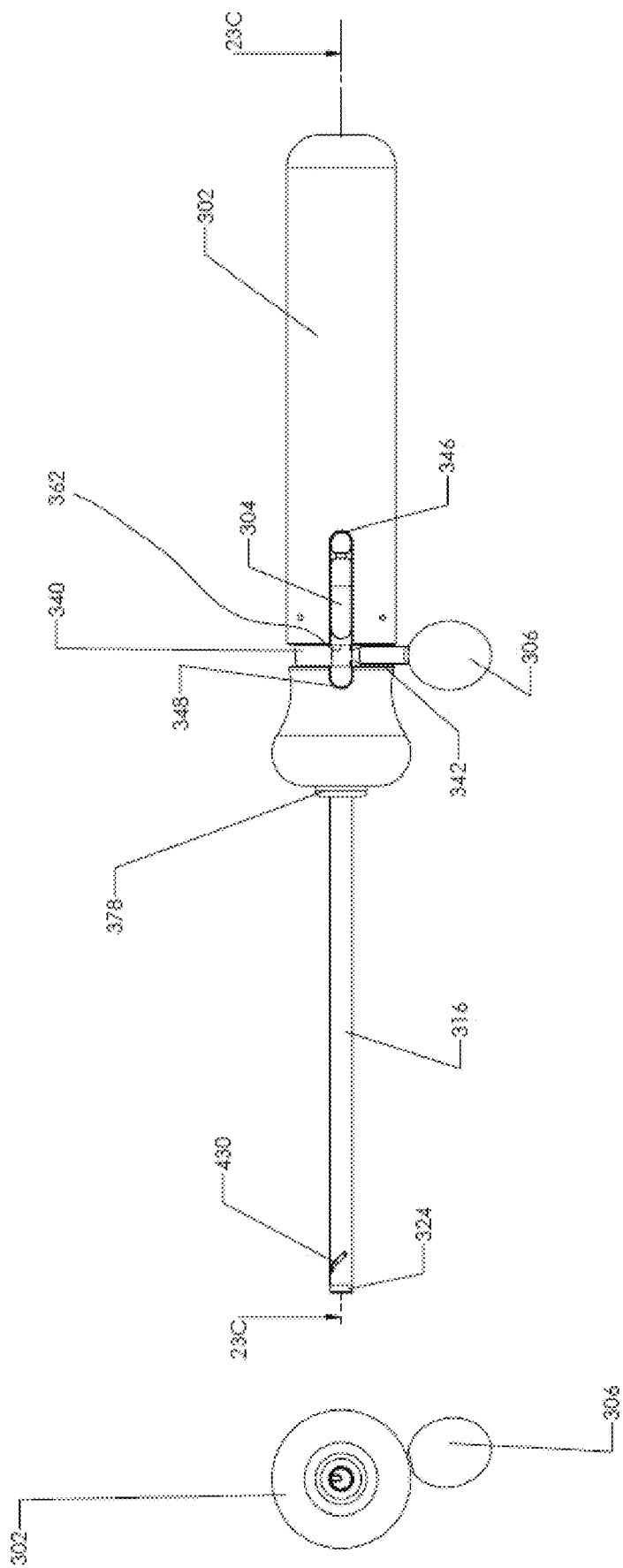
Figure 23C:
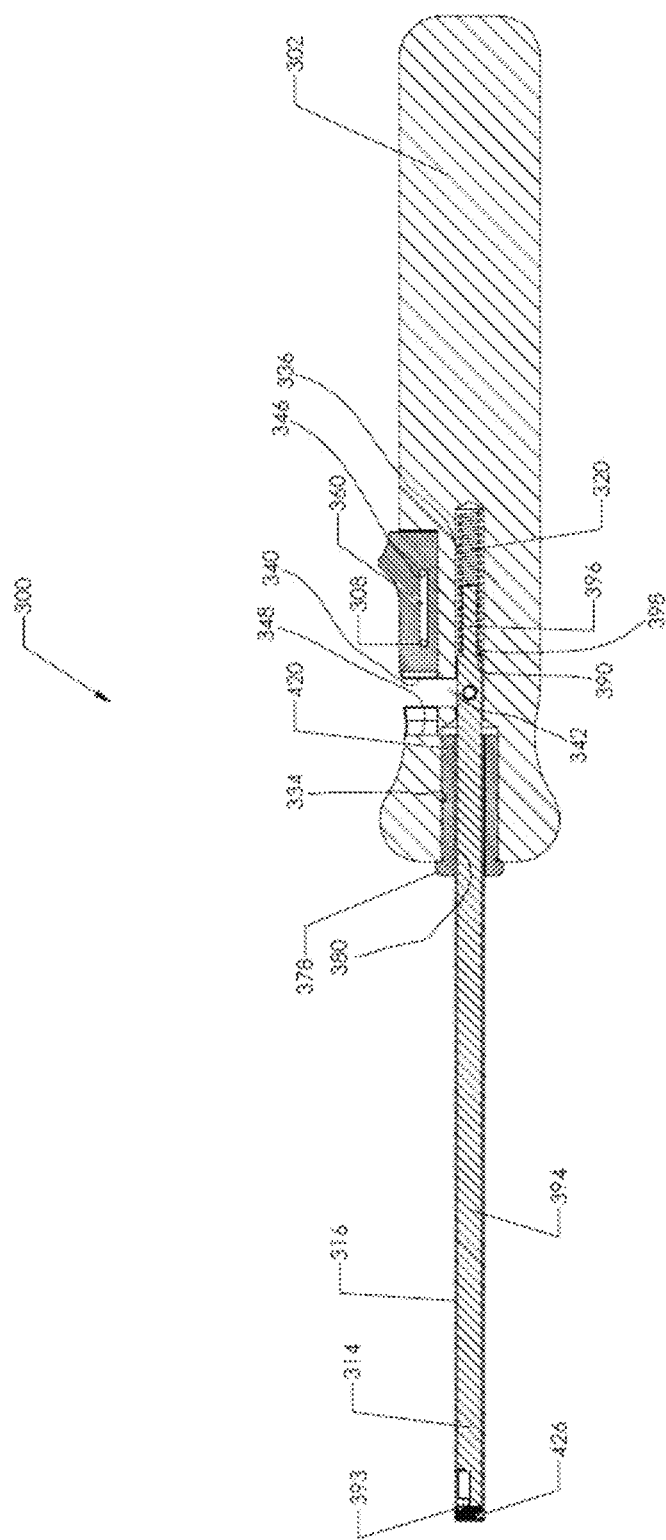
FIG. 23C is a simplified sectional illustration of the assembled cutting device of FIG. 23A in a cutting orientation, according to some embodiments of the invention; section being taken along lines 23C-23C in FIG. 23B.

Reference is now made to FIGS. 23A and 23B, which are simplified respective pictorial view and elevation view illustrations of assembled cutting device 300 of FIG. 13 in cutting orientation and to FIG. 23C, which is a simplified sectional illustration of the assembled cutting device 300 of FIG. 23A in a cutting orientation, according to some embodiments of the invention. Section being taken along lines 23C-23C in FIG. 23B.

According to some exemplary embodiments, the cutting device 300 is shown in cutting orientation in FIGS. 23A-23C. According to some embodiments, the internal and external cutting elements 314 and 316 are arranged along a mutual longitudinal axis 403. In some embodiments, the internal cutting element 314 is inserted within the external cutting element 316 and aligning element 324 is fixedly attached to the external cutting element 316, such that proximal portion 442 of aligning element 324 lies within annular recess 428 of external cutting element 316. In some embodiments, the U-shaped opening 446 of aligning element 324 remains aligned with the distal portion 432 of spirally-shaped groove 430 of external cutting element 316 aligned with the distal portion 432 of spirally-shaped groove 430 of external cutting element 316, however it is not aligned with gap 412 of internal cutting element 314.

According to some embodiments, proximal end 420 of external cutting element 316 remains inserted into the interior of bushing 378 and lies against inner surface 380 thereof. In some embodiments, the bushing 378 is fixedly held within the distal cylindrical portion 334 of internal recess 332 of handle 302 by means of connecting pin 322 that engages recess 384 of bushing 378.

It is a particular feature of some embodiments of the present invention that distalmost wall surface 393 of internal cutting element 314 is coplanar with distal circumferential edge 426 of external cutting element 316.

In some embodiments, the proximal end 390 of internal cutting element 314 protrudes proximally from the proximal end 420 of external cutting element 316, such that the proximal part of intermediate portion 394 and cylindrical shaft 396 is inserted within proximal cylindrical portion 336 of internal recess 332 of handle 302 and biasing element 320 is also inserted within proximal cylindrical portion 336 of handle 302 and encircles cylindrical shaft 396 of internal cutting element 314.

It is a particular feature of some embodiments of the present invention that the biasing element 320 exerts constant force on proximally facing shoulder 398 of internal cutting element 314 in order to assure that the distalmost wall surface 393 of internal cutting element 314 is coplanar with distal circumferential edge 426 of external cutting element 316 for enabling cutting of a surgical suture that is placed within the spirally-shaped groove 430 of external cutting element 316.

It is further seen in FIGS. 23A-23C that in some embodiments, intermediate cylindrical portion 372 of rotating button 306 is disposed within through bore 340 of handle 302 and cylindrical longitudinal portion 374 of rotating button 306 is inserted into through bore 400 of internal cutting element 314.

It is seen in FIGS. 23A-23C that in some embodiments, the rotating button 306 is now disposed adjacent the second edge 342 of through bore 340 of handle 302 in the cutting orientation.

Additionally, locking button 304 is now positioned within second longitudinal groove 342 of handle 302 adjacent proximal curved wall 346 of second longitudinal groove 342 of handle 302. Optionally, locking button 304 is slidably connected to handle 302 by means of connecting pin 308, which is inserted into longitudinal groove 360 of locking button 304. In some embodiments, the connecting pin 308 is positioned adjacent distal curved wall 364 of longitudinal groove 360 in the cutting orientation.

It is a particular feature of some embodiments of the present invention that the locking is displaced proximally in order to allow, for example, further rotation of the rotating button 306 towards second edge 342 of through bore 340 of handle 302, thus allowing cutting of the surgical suture.

It is a further particular feature of some embodiments of the present invention that in this cutting orientation gap 412 of opening 410 of internal cutting element 114 is further rotated using the rotating button 306 and is now not aligned with the spirally-shaped groove 430 of external cutting element 316 and opening 446 of aligning element 324. In some embodiments, in this rotational position of the internal cutting element 314 spirally-shaped groove 430 of external cutting element 316 and opening 446 of aligning element 324 do not overlap with opening 410 of internal cutting element 314, thus the surgical suture is cut during rotation of the internal cutting element 314 relative the external cutting element 316.

It is a yet further particular feature of some embodiments of the present invention that the surgical suture is cut by means of shear forces produced by rotation of two substantially coplanar surfaces one against each other, namely the distalmost wall surface 393 of internal cutting element 314 and the distal circumferential edge 426 of external cutting element 316.

Figure 24:
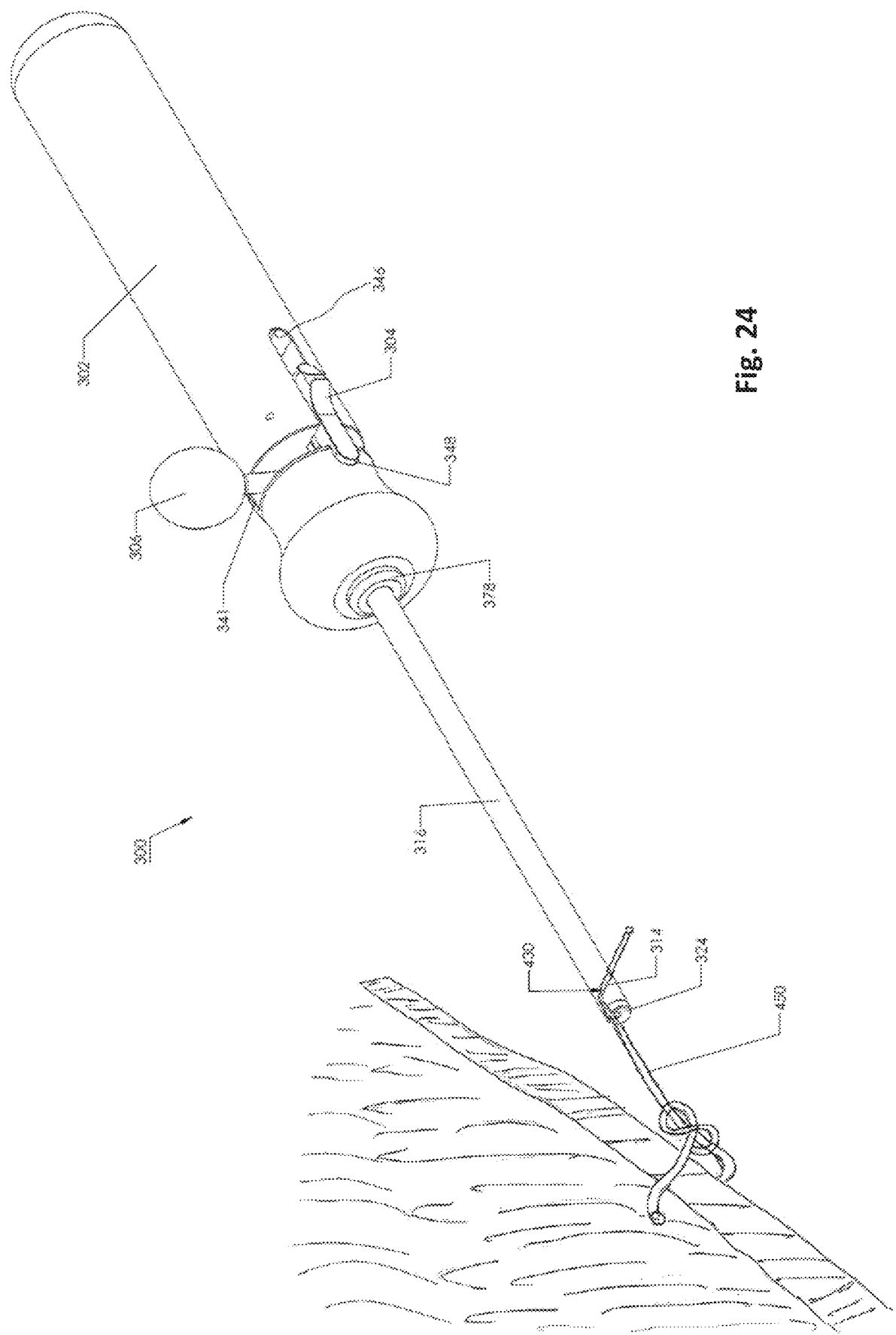
FIG. 24 is a simplified pictorial view illustration showing the cutting device of FIG. 13 in a non-actuated operative orientation, showing the surgical suture passed through the tissue, according to some embodiments of the invention.

Reference is now made to FIG. 24, which is a simplified pictorial view illustration showing the cutting device 300 of FIG. 13 in a non-actuated operative orientation, showing the surgical suture passed through the tissue, according to some embodiments of the invention.

It is seen in FIG. 24 that in some embodiments, the locking button 304 is disposed adjacent distal curved wall 348 of second longitudinal groove 342 of handle 302 and thus partially blocking rotation of rotating button 306 which allows, for example, cutting of surgical suture 450.

In some embodiments, surgical suture 450 is passed through the tissue of a patient and is placed through the opening 446 of aligning element 324, gap 412 of internal cutting element 314 and spirally-shaped groove 430 of external cutting element 316 in this non-actuated orientation.

Figure 25:
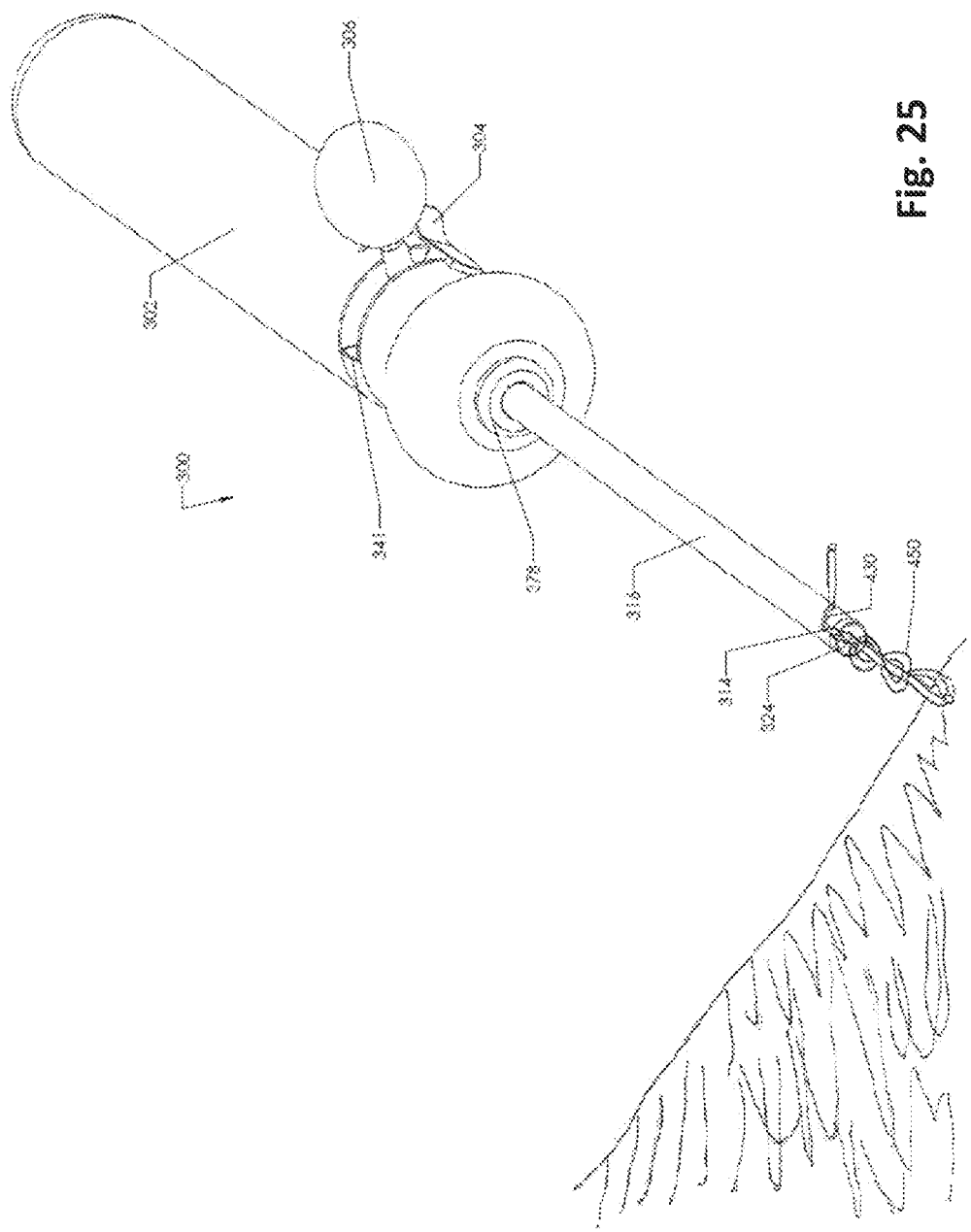
FIG. 25 is a simplified pictorial view illustration showing the cutting device of FIG. 13 in a partially-actuated operative orientation, showing the surgical suture passed through the tissue and retained within the cutting device of FIG. 13, according to some embodiments of the invention.

FIG. 25 is a simplified pictorial view illustration showing the cutting device 300 of FIG. 13 in a partially-actuated operative orientation, showing the surgical suture 450 passed through the tissue and retained within the cutting device 300 of FIG. 13, according to some embodiments of the invention.

It is seen in FIG. 25 that in some embodiments, the locking button 304 is disposed adjacent distal curved wall 348 of second longitudinal groove 342 of handle 302 and thus partially blocking rotation of rotating button 306 which allows cutting of surgical suture 450. In some embodiments, rotating button 306 is partially rotated towards locking button 304 and thus causing rotation of internal cutting element 314 relative external cutting element 316 and retaining of surgical suture 450 therebetween.

According to some embodiments, surgical suture 450 is passed through the tissue of a patient and is retained between the opening 446 of aligning element 324, gap 412 of internal cutting element 314 and spirally-shaped groove 430 of external cutting element 316 in this partially-actuated orientation.

In some embodiments, following the partially-actuated orientation, the locking button is displaced proximally, rotating button 306 is further rotated and causing cutting of surgical suture 450.

It is further noted that in some embodiments of the invention, the cutting device 300 can be disposable and may be used for a single procedure.

Exemplary Cutting Device Operated by a Linear Movement of a Handle

Figure 26A:
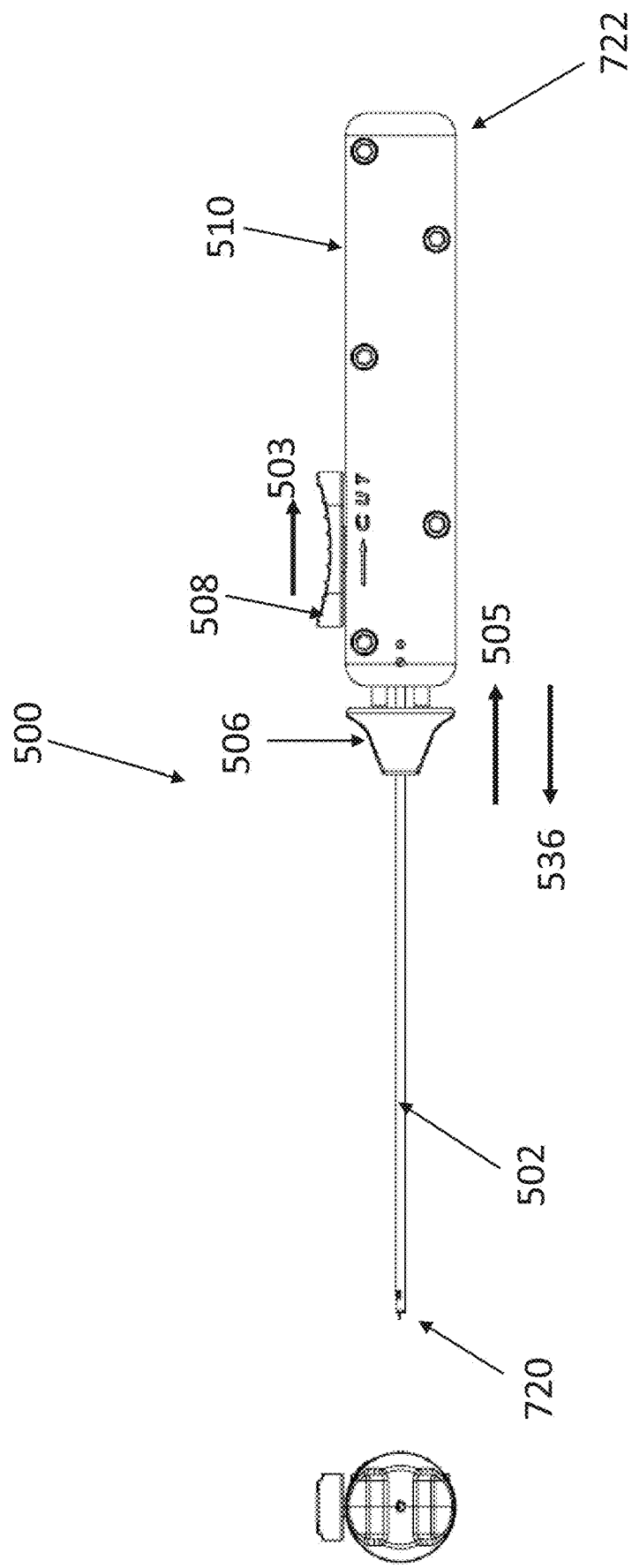
FIG. 26A is a side view illustration depicting a suture cutting device, according to some embodiments of the invention.

Reference is now made to FIG. 26A depicting a suture cutting device, according to some exemplary embodiments of the invention.

According to some embodiments, a cutting device 500 having a distal end 720 and a proximal end 722 comprises an external element, for example external cutting element 502 connected to a handle 510. In some embodiments, external cutting element 502 is inserted through a bushing 506 into handle 510. In some embodiments, handle 510 comprises a cutting control element, for example slidable button 508, configured to activate a cutting mechanism of cutting device 500 when it is moved linearly in direction 503.

According to some embodiments, bushing 506 controls the suture capturing and retention processes. In some embodiments, when bushing 506 moves in direction 505, a thread can be inserted into external cutting element 502. In some embodiments, once the thread is within external cutting element 502, movement of bushing 506 in direction 536 traps the thread within cutting device 500, for example by creating a closed loop which surrounds the thread.

Figure 26B:
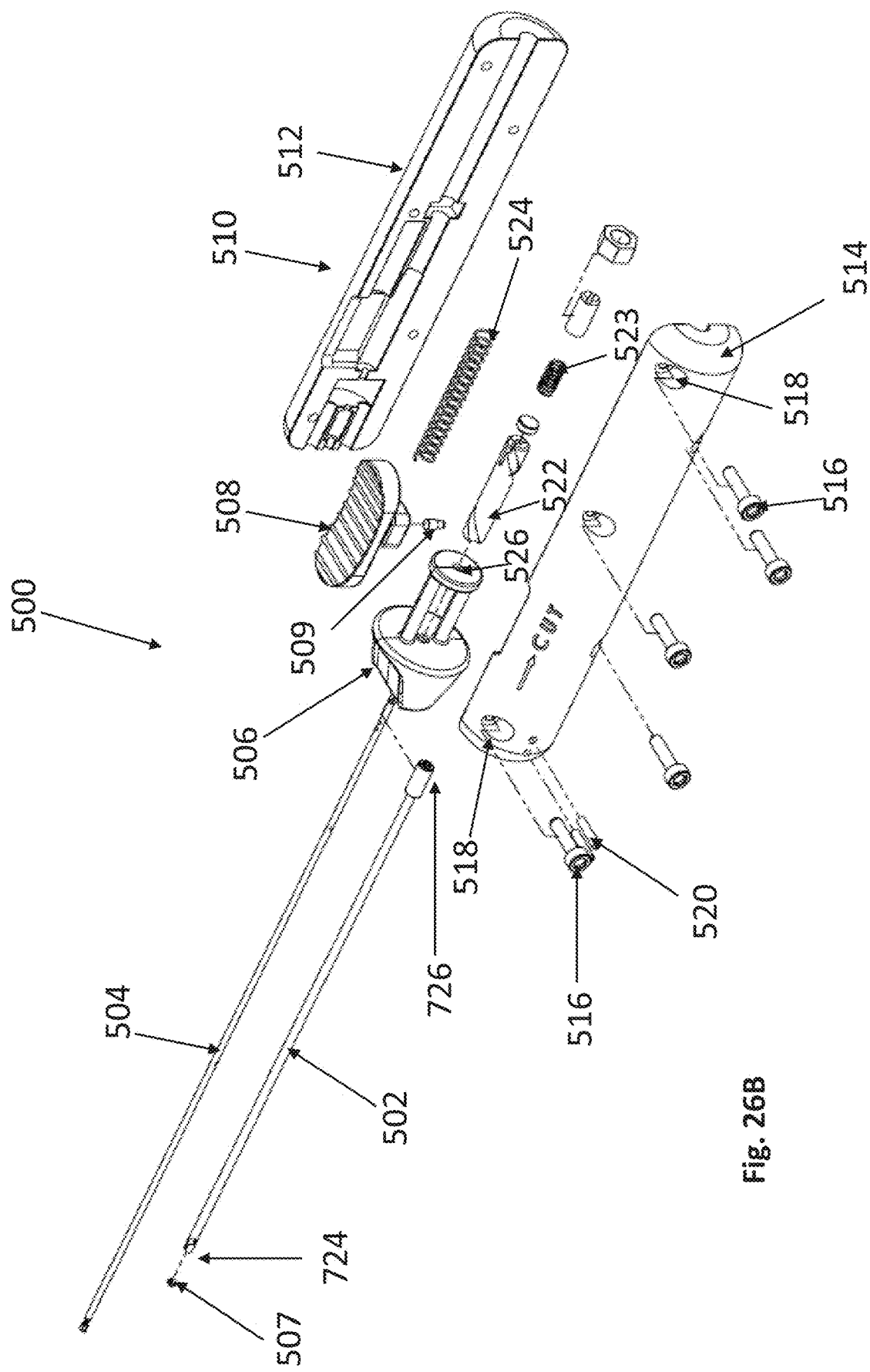
FIG. 26B is an exploded view illustration depicting the cutting device of FIG. 26A, according to some embodiments of the invention.

Reference is now made to FIG. 26B, depicting an exploded view of device 500, according to some exemplary embodiments of the invention.

According to some embodiments, cutting device 500 comprises an internal cutting element 504 having a distal end 724 and a proximal end 726, placed within an external cutting element 502. In some embodiments, internal cutting element 504 is configured to slidably move and rotate within external element 502. Optionally, external cutting element is a fixed cutting element.

In some embodiments, internal cutting element 504 is partially inserted through bushing 506, into handle 510. In some embodiments, internal cutting element 502 is connected to a movement converter 522, which converts for example, a linear movement of slidable button 508 into a rotational movement of internal cutting element 504. Optionally, a biasing element, for example a coil spring 523 controls the linear movement of cutting element 502. Optionally, coil spring 523 allows, for example to return of internal cutting element 504 to a forward position, for example closer to the distal end of the cutting device, when biasing element 523 is at least partially relaxed.

In some embodiments, an aligning element 507 is connected to the distal end 724 of external cutting element 502.

According to some exemplary embodiments, handle 510 is made of two symmetrical portions, which are attached to each other using bolts 516, or using any other connection means.

According to some embodiments, slidable button 508 is partially inserted into handle 510. In some embodiments, slidable button 508 is connected to movement converter 522 via connecting member 509 which travels within a spiral circumferential groove of movement converter 522. In some embodiments, movement of connecting member 509 within the circumferential groove of movement converter 522, converts the linear movement of slidable button 508 into a rotational movement of movement converter 522 and internal cutting element 502. Optionally, the sliding movement of slidable button 508 is controlled by a biasing element for example, coil spring 524. In some embodiments, slidable button 508 is moved to a forward position for example, closer to the distal end of the cutting device when coil spring 524 is relaxed.

Reference is now made to FIG. 26C describing an external cutting element 502 of the cutting device 500 of FIG. 26A and partial enlargements thereof, according to some embodiments of the invention.

According to some embodiments, the external cutting element 502 has a proximal end 726, a distal end 724 and an intermediate portion 725. In some embodiments, the external cutting element 502 is an integrally formed longitudinal hollow element, optionally made of metal. In some embodiments, the external element is a stationary external element, optionally a tubular external element with a diameter 301 in the range of 2-4 mm.

According to some embodiments, an aligning element 507 having a front opening, for example U-shaped opening 532, is connected to the distal end 724 of external cutting element 502.

According to some exemplary embodiments, a groove, for example spirally shaped groove 539 is formed at the distal end 722 of external cutting element 502, extending slightly proximally from the front opening, for example U-shaped opening 532 of aligning element 507. In some embodiments, the spirally shaped groove 539 comprises a distal portion 740 which optionally, extends generally proximally longitudinally along axis 727 and a diagonally extending portion 534 extending from distal portion 740. Optionally, the spirally shaped groove 430 is adapted for insertion of a surgical suture therein.

Figure 26D:
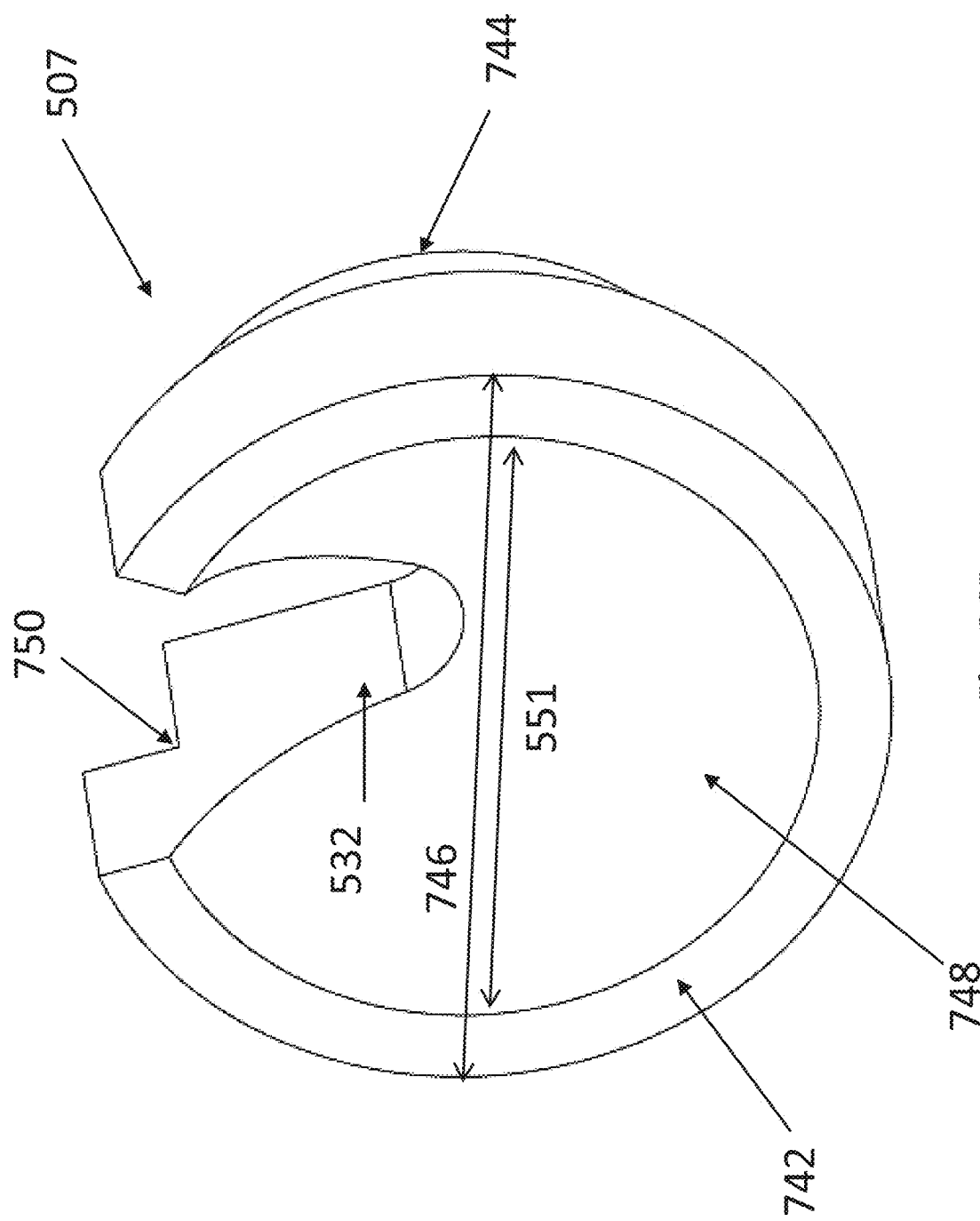
FIG. 26D is a schematic view depicting an aligning element of the cutting device, according to some embodiments of the invention.

Reference is now made to FIG. 26D describing an alignment element 507 of the cutting device 500 of FIG. 26A, according to some embodiments of the invention.

According to some exemplary embodiments, aligning element 507 is an annular element, optionally a concave annular element, having a distal portion 742 of a first diameter and a proximal portion 744 of a second diameter. In some embodiments, the second diameter is smaller than the first diameter. In some embodiments the first diameter 746 of the distal portion is in a range of 2-4 mm. In some embodiments, the concave shaped portion 748 of aligning element 507 has a third diameter 551 in a range of 1.7-3.3 mm. In some embodiments, the concave-shaped portion 748 of aligning element 507 allows for example, to push a knot of the surgical suture to a desired location.

In some embodiments, a proximally facing shoulder 750 is defined between the distal portion 742 and the proximal portion 442. Optionally, a U-shaped opening is formed through distal portion 742 and proximal portion 744 for example, for insertion of surgical suture therethrough.

Figure 26E:
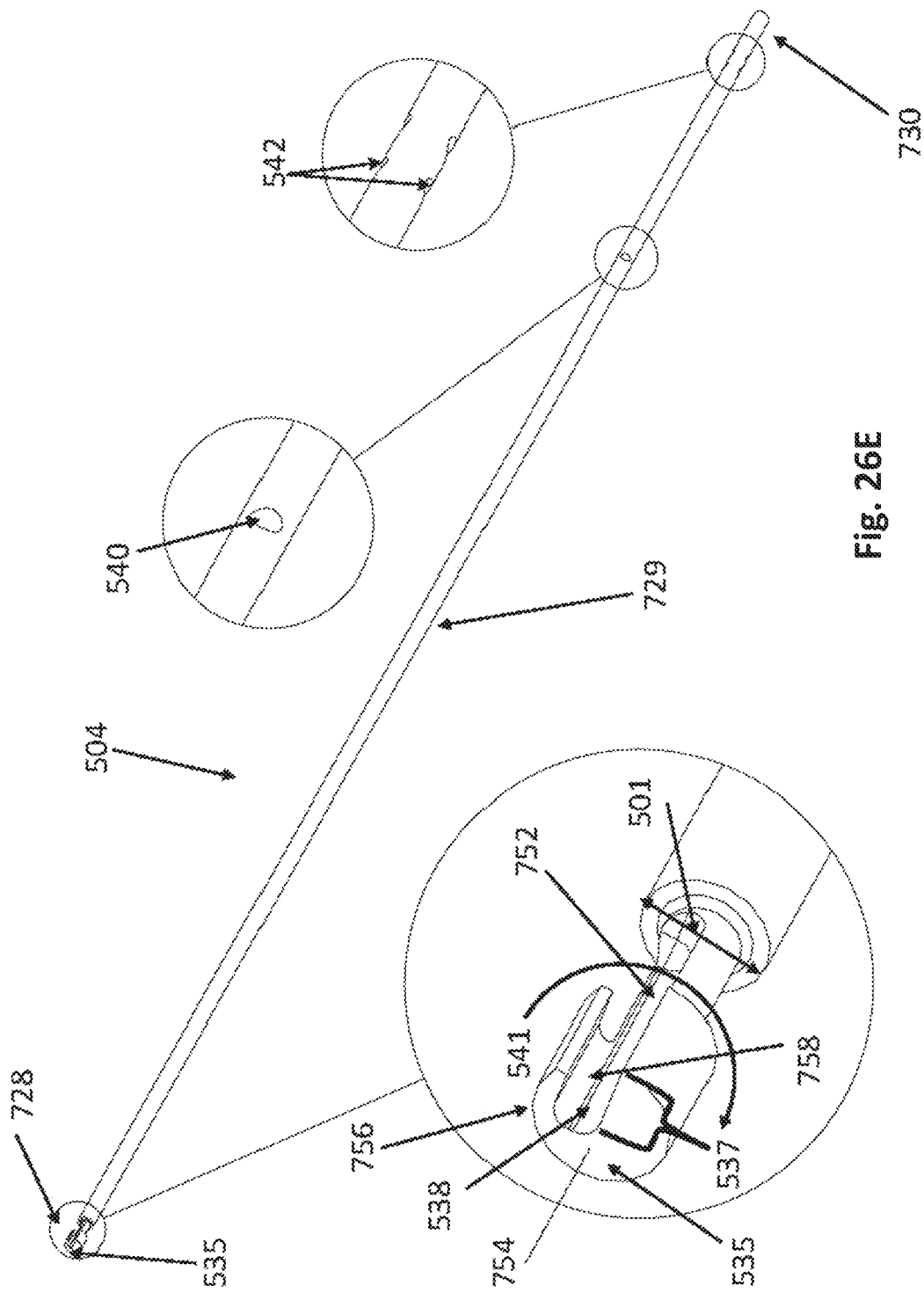
FIG. 26E is a schematic illustration depicting the internal cutting element of the cutting device, according to some embodiments of the invention.
Figure 26F:
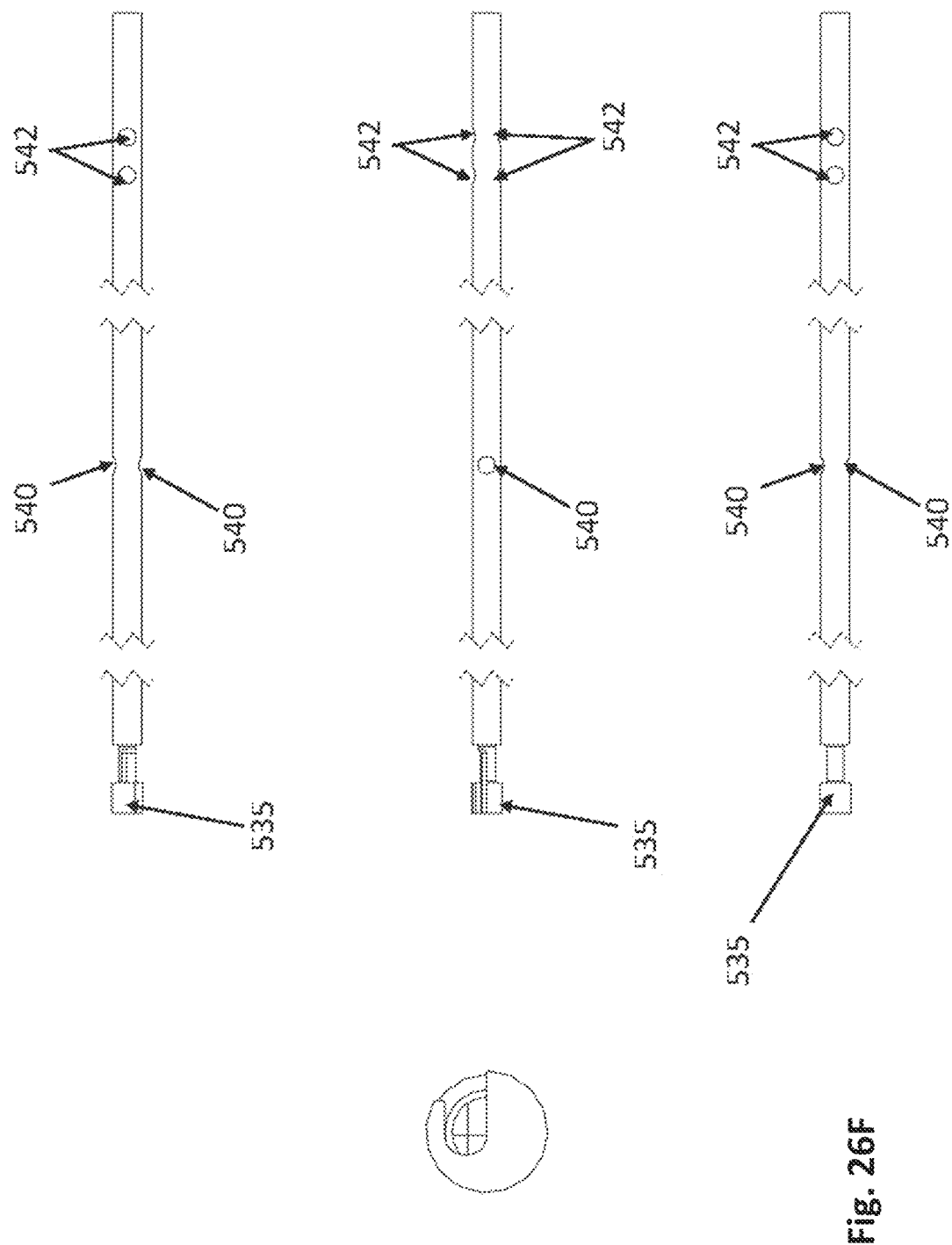
FIG. 26F is a schematic illustration depicting the internal cutting element in different orientations, according to some embodiments of the invention.

Reference is now made to FIGS. 26E and 26F describing an internal cutting element 504 of cutting device 500, according to some embodiments of the invention.

In some embodiments, the internal cutting element 504 has a proximal end 730, a distal end 728 having a distalmost wall surface 535 and an intermediate portion 729. In some embodiments, the internal cutting element 504 is an integrally formed longitudinal element, optionally made of metal. In some embodiments, the diameter 501 of internal cutting element 504 is in a range of 1.6-3.8 mm.

In some embodiments, a recess 752 is formed in the distal end 728 of internal cutting element 504, adjacent the distalmost wall surface 535. In some embodiments, recess 752 is generally longitudinal extending along longitudinal axis 754. Optionally, the recess extends internally into the internal cutting element 504. In some embodiments, the recess 752 forms a distal flange 756 at the distal end 728 of internal cutting element 504.

In some embodiments, an opening 538, optionally a U-shaped opening, is formed within distal flange 756, which extends along a portion of flange 756 and forms a gap 758 at its circumference, for example, for insertion of a thread of a surgical suture therethrough.

In some embodiments, opening 538 comprises a cutting edge 537 configured to cut a thread by applying, for example, shear forces on the thread. In some embodiments, cutting edge 537 cuts the thread when flange 756 rotates at least 90° degrees, for example 90° degrees or 180° degrees in direction 541. In some embodiments, the length of cutting edge 537 is in a range of 0.7-1 mm, for example 0.8 mm, 0.85 mm, 0.9 mm.

According to some embodiments, internal cutting element 504 comprises a bore 540 at the intermediate portion, for example to allow the connection of bushing 506 to the internal cutting element 504. Optionally, connection of bushing 506 allows to control the linear movement of internal cutting element 504.

Additionally, internal cutting element 504 comprises at least one set of spaced-apart bores 542 adjacent to the proximal end 730. In some embodiments, bores 542 allow, for example to connect internal cutting element 504 to a movement converter, for example movement converter 522. Optionally, movement converter 522 controls the rotation movement of internal cutting element 504.

Figure 26G:
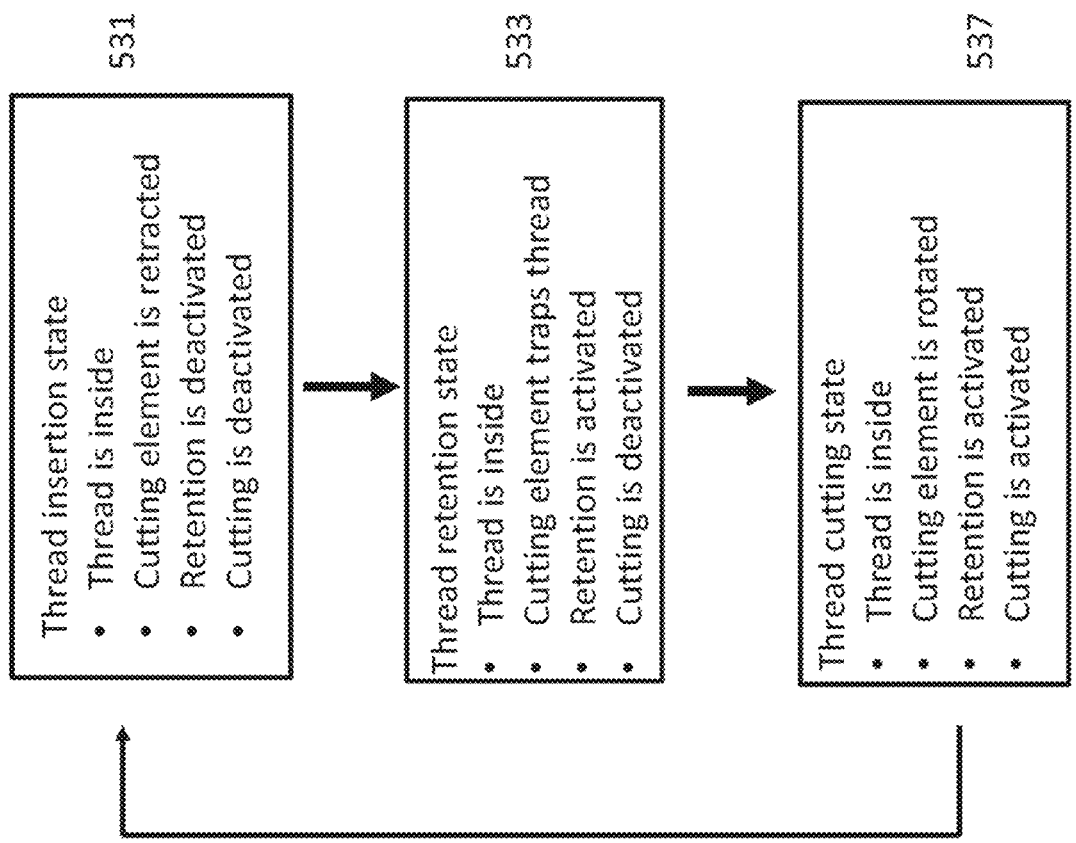
FIG. 26G is a state diagram depicting the primary states of the cutting device of FIG. 26A, according to some embodiments of the invention.
Figure 32A:
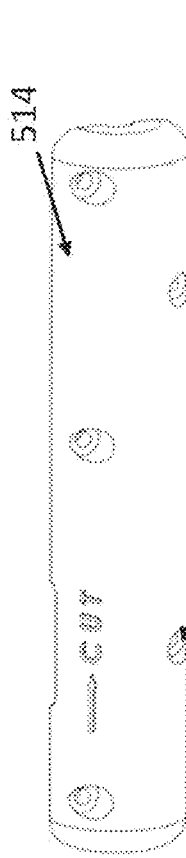
FIGS. 32A-32D are schematic side views illustrations depicting parts of a cutting device handle, according to some embodiments of the invention.
Figure 32B:
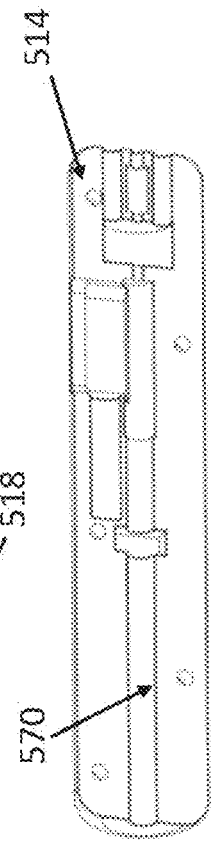
Figure 32C:
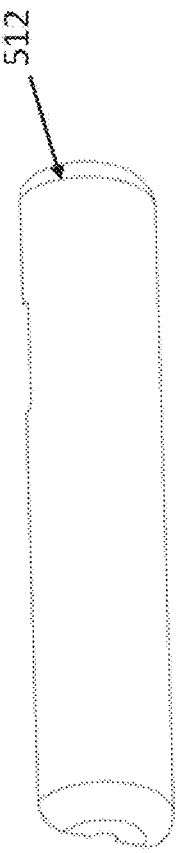
Figure 32D:
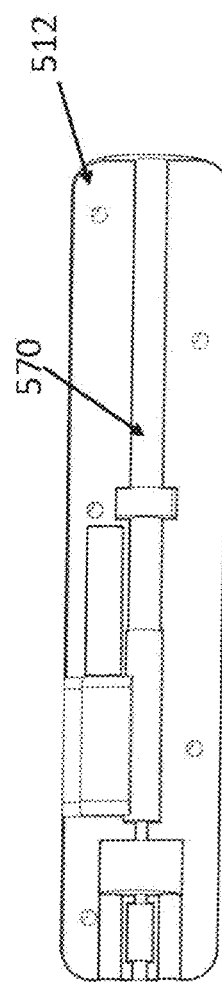

Reference is now made to FIG. 26G depicting the three main activation states of the suture cutting device, according to some exemplary embodiments of the invention.

According to some exemplary embodiments, in a non-actuated orientation, for example thread insertion state 531, a surgical suture thread is inserted or loaded and unloaded into the suture cutting device, optionally through at least one opening or a groove, for example a spirally shaped groove at the distal end of the cutting device. In some embodiments, in a non-actuated orientation, for example thread insertion state 531, the cutting element, for example internal cutting element 502 is retracted, for example to allow the insertion of a suture thread through the at least one opening or the groove. In some embodiments, internal cutting element 502 is retracted by moving bushing 506 in an opposite direction to the distal end 724 of external cutting element 504, for example in direction 505 as seen in FIG. 26A. In some embodiments, in the thread insertion state 531, both retention and cutting mechanisms are deactivated.

According to some embodiments, in a partially-actuated orientation of the cutting device for example, thread retention state 533, the thread is positioned within the cutting device. In some embodiments, the internal cutting element is placed in a forward position and traps the thread within the device. In some embodiments, the thread is trapped in a loop formed for example, by the internal cutting element and the external cutting element of the cutting device. In some embodiments, during thread retention state 533, the retention mechanism is activated and prevents the release of the thread from the cutting device. In some embodiments, the formation of a loop around the thread allows, for example to slide the cutting device along the thread, for example to a desired cutting position. In some embodiments, during thread retention state 533 the cutting mechanism is deactivated.

According to some embodiments, in a cutting orientation of the cutting device for example, a thread cutting state 537, the thread is placed within the cutting device, and the cutting element is moved linearly or rotationally, for example to apply shear forces on the thread. Application of shear forces on the thread lead, in some embodiments, to thread cutting. In some embodiments, in a thread cutting state both retention and cutting mechanisms are activated.

Reference is now made to FIGS. 27A-27D depicting a cutting device 500, as seen in FIG. 26A in a non-actuated orientation, for example, thread insertion state 531, according to some embodiments of the invention.

According to some exemplary embodiments, in a thread insertion state a retention control element, for example bushing 506 is pushed towards the proximal end 722 of the cutting device, for example in direction 505. In some embodiments, when bushing 506 is pushed the internal cutting element is retracted and a suture thread, for example thread 530 is inserted into the cutting device. In some embodiments, the suture thread is inserted through an opening at the front end of the device for example, U-shaped opening 532. In some embodiments, the suture thread passes through the spirally shaped groove 539, and optionally exits through diagonally extending portion 534.

Reference is now made to FIGS. 28A-28D depicting a cutting device 500 of FIG. 26A in a partially-actuated orientation, for example thread retention state 533, according to some exemplary embodiments of the invention.

According to some embodiments, in a thread retention state the retention control element, for example bushing 506 is pushed towards the distal end 720 of the cutting device, for example in direction 536. In some embodiments, bushing 506 is moved manually in direction 536. Alternatively, bushing 506 is pushed by a biasing element, for example, coil spring 523. In some embodiments, in a thread retention state the distalmost wall surface 535 of internal cutting element 504 is pushed against the proximal portion 744 of aligning element 507 for example, to trap a portion of thread 530 within cutting device 500. Optionally, when thread 530 is captured, the cutting device can slide along the thread, for example, to a desired cutting position.

Reference is now made to FIGS. 29A-29D depicting cutting device 500 of FIG. 26A in a cutting orientation, for example thread cutting state 537, according to some embodiments of the invention.

According to some embodiments, in a thread cutting state, slidable button 508 is manually moved in direction 800 towards the proximal end 722 of cutting device 500. In some embodiments, movement of the slidable button 508 in direction 800 rotates internal cutting element 504 and distal flange 756 in direction 541. In some embodiments, slidable button 508 range of movement is up to 15 mm, for example 13 mm. In some embodiments, the linear movement of slidable button 508 rotates distal flange 756 in a range of 150°-210° degrees, for example 170° degrees, 185° degrees, or 195° degrees.

According to some embodiments, slidable button 508 moves in an axial direction away from the thread to cut the thread. In some embodiments, the movement of the slidable button in an axial direction away from the thread rotates the internal cutter, for example internal cutting element 504. Optionally, the movement of the movable button in an axial direction away from the thread rotates the internal cutter by rotating a movement converter, for example movement converter 522 connected to the movable button by a connecting member.

Exemplary Cutting and Retention Mechanisms

Reference is now made to FIGS. 30A and 30B describing a cutting device in a thread insertion state, according to some embodiments of the invention.

According to some exemplary embodiments, the retention control, for example bushing 506 is manually pushed in direction 505, for example to retract internal cutting element 504 within external cutting element 502. In some embodiments, movement of bushing 506 in direction 505, retracts distal flange 756 to allow, for example, insertion of thread 530 through an opening aligning element 507 of the external cutting element 502. In some embodiments, the moving of bushing 506 in direction 505, compresses a biasing element, for example coil spring 523 placed within handle 510.

Reference is now made to FIGS. 30C and 30D describing a cutting device in a thread retention state, according to some embodiments of the invention.

According to some exemplary embodiments, after insertion of thread 530 into the cutting device, the retention control element, for example bushing 506 is manually moved in direction 536, for example, towards the distal end 720 of cutting device 500. Alternatively, coil spring 526 relaxes and pushes bushing 506 in direction 536.

According to some embodiments, movement of bushing 506 in direction 536 moves distalmost wall surface 535 of flange 756 against the proximal portion of aligning element 507. In some embodiments, flange 756 and aligning element 507 capture a portion of thread 530 within cutting device 500 by for example, surrounding the thread. In some embodiments, the capturing prevents the release of thread 530 from the cutting device. Optionally, the capturing allows sliding the device along thread 530, for example towards a knot.

Reference is now made to FIGS. 30E and 30F describing cutting device 500 of FIG. 26A in a cutting orientation, for example thread cutting state, according to some embodiments of the invention.

According to some embodiments, slidable button 508 is manually moved in direction 800 towards the proximal end 722 of cutting device 500. In some embodiments, the linear movement of slidable button 508 is converted to a rotational movement of internal cutting element 504 and flange 756. In some embodiments, the linear movement of slidable button 508 is converted to a rotational movement by movement converter 522 located within handle 510 of the device. In some embodiments, when slidable button 508 is moves in direction 800, it compresses a biasing element of the cutting mechanism, for example coil spring 524. In some embodiments, when thread cutting is over, cutting control 508 is manually moved in direction 536. Alternatively, coil spring 524 relaxes and pushes slidable button 508 in direction 536. In some embodiments, movement of slidable button 508 in direction 536 rotates internal cutting element 504 and flange 756 in an opposite direction to direction 541, as shown in FIG. 29C.

Reference is now made to FIGS. 31A and 31B describing a slidable button 508 and a connecting member 509 of cutting device 500, according to some embodiments of the invention.

According to some exemplary embodiments, slidable button 508 comprises an upper surface 559 configured to have an increased surface area, for example, to allow better contact between the surface and at least one finger of a user of the cutting device. Additionally, cutting control 508 comprises a protrusion 555, for example for connecting slidable button 508 via connecting member 509 to a movement conversion component.

According to some exemplary embodiments, connecting member 509 comprises an upper portion 760 for example, for connecting to slidable button 508. In some embodiments, connecting member 509 comprises a lower portion 762, for example, for connecting to movement converter 522.

Reference is now made to FIGS. 31C and 31D, describing a movement conversion component of a suture cutting device, according to some embodiments of the invention.

According to some exemplary embodiments, movement converter 522 is a cylindrical elongated component, with a spiral circumferential groove 560 on the outer surface. Additionally, movement converter 522 comprises a central tubular channel 564, for example, to allow the insertion of the proximal end of internal cutting element 504 into movement converter 522.

In some embodiments, the lower portion 762 of connecting member 509 is configured to travel within groove 560. In some embodiments, the travelling of connecting member 509 within groove 560 leads, for example, to rotation of movement converter 522 which in turn rotates internal cutting element 502.

Reference is now made to FIGS. 32A-32D, describing a cutting device 500 handle casing, according to some embodiments of the invention.

According to some exemplary embodiments, a handle casing of a cutting device is comprised from at least two parts, for example handle casing parts 512 and 514, optionally symmetrical. In some embodiments, handle casing parts 512 and 514 are interconnected by insertion of threaded members, for example pins or screws through openings 518 located in at least one part of the handle casing. In some embodiments, handling casing parts 512 and 514 comprising at least one indentation or groove 570 in the internal surface, configured to fit internal mechanisms components, for example the retention and/or cutting mechanism components.

Figure 33:
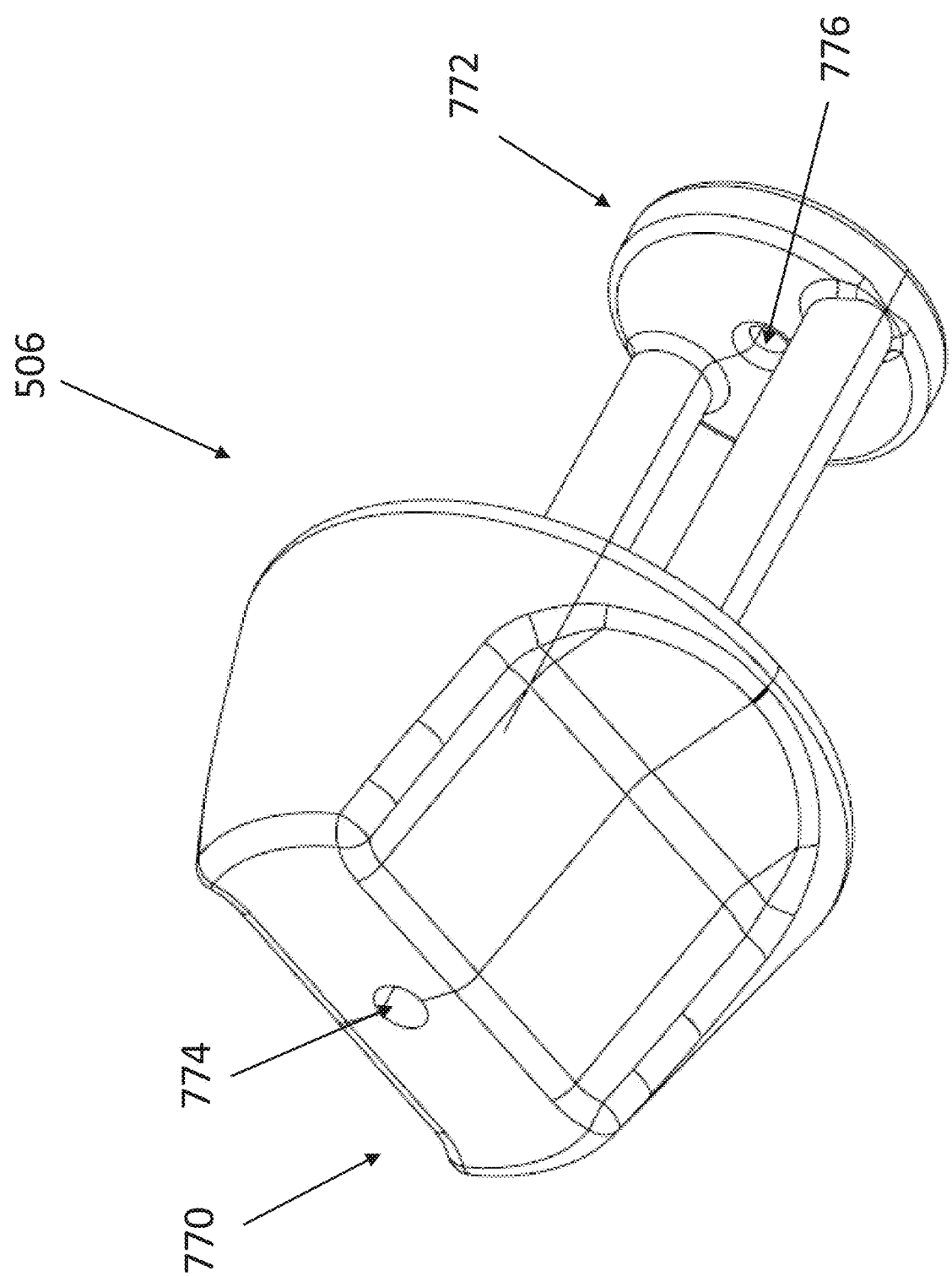
FIG. 33 is a schematic illustration depicting a retention control element of the cutting device, according to some embodiments of the invention.

Reference is now made to FIG. 33, describing a retention control element of a suture thread cutting device, according to some embodiments of the invention.

According to some embodiments, a retention control of a cutting device, for example bushing 506 comprises a distal end 770 and a proximal end 772 configured to be inserted into the handle of the cutting device. In some embodiments, distal end 770 comprises an opening 774 for insertion of the proximal end of internal cutting element into bushing 506. In some embodiments, internal cutting element is partially inserted through opening 774 and passed through opening 776 into the handle.

Exemplary Cutting Device Activation Process

Figure 34:
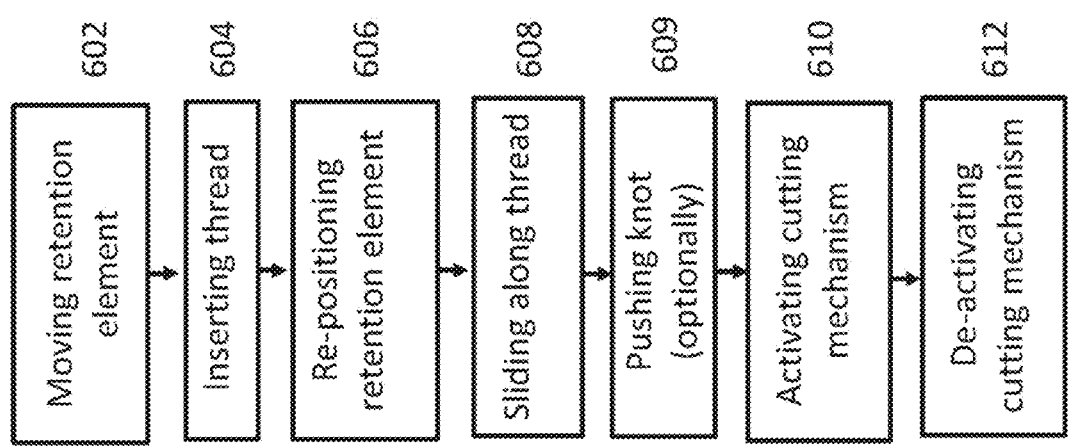
FIG. 34 is a detailed flow chart describing the thread cutting process using the cutting device, according to some embodiments of the invention.

Reference is now made to FIG. 34 depicting a detailed activation process of a cutting device, according to some exemplary embodiments of the invention.

According to some embodiments, a retention element is moved at 602, for example to allow the insertion of a thread or a suture into the cutting device. In some embodiments a retention mechanism is moved by aligning an opening in an external element, for example an external cutting element with an opening in an internal cutting element. Alternatively, a retention mechanism is activated by retracting an internal cutting element, for example to open at least one opening in the external element.

According to some exemplary embodiments, a suture thread is inserted through at least one opening in the external tube at 604. In some embodiments, the suture thread is inserted through an opening at the front distal end of the external element and exits through an opening at the side of the external element. Alternatively, the suture thread is inserted through an opening in one side of the external element and exits through an opening in the opposite side of the external element. Optionally, the thread is inserted and exits through the same opening or through two openings located at the same side of the external element.

According to some exemplary embodiments, the retention element is re-positioned at 606. In some embodiments, once the retention element is re-positioned, a portion of the thread is retained within the cutting device. In some embodiments, when retained, the suture thread crosses the external tube. In some embodiments, the inner cutting element and the external cutting element create surrounds the thread and allows for example, sliding the cutting device along the thread.

According to some exemplary embodiments, the cutting device slides along the thread. Optionally, the cutting device slides along the thread until a desired cutting point is reached at 608. In some embodiments, the desired cutting point is in a close proximity to the thread knot.

According to some exemplary embodiments, when the device slides along the retained thread, the knot can be pushed to a desired location at 609, for example to a location closer to the sutured tissue.

According to some exemplary embodiments, the cutting mechanism is activated, for example, at a desired cutting point at 610. In some embodiments, safety means are deactivated prior to activation of the cutting mechanism. In some embodiments, the cutting mechanism is activated by moving an internal cutting element located in the external element of the device through a portion of the suture thread that is located within the external element. In some embodiments, the movement of the inner cutting component is linear, for example a linear movement towards the distal end of the external tube of the cutting device. Alternatively, the inner cutting component is rotated for example, to allow cutting of the suture thread.

According to some exemplary embodiments, the cutting mechanism is deactivated at 612. In some embodiments, the cutting mechanism is deactivated by returning the internal cutting element to its position prior to activation at 610. In some embodiments, the cutting mechanism is deactivated by manually turning a knob or a handle in an opposite direction to the direction used for activation of the cutting mechanism. Alternatively, deactivation of the cutting mechanism is performed by a biasing element, for example a spiral spring that pushes the inner cutting element to its position prior to cutting mechanism activation at 610.

Exemplary Cutting Element Positions

Figure 35:
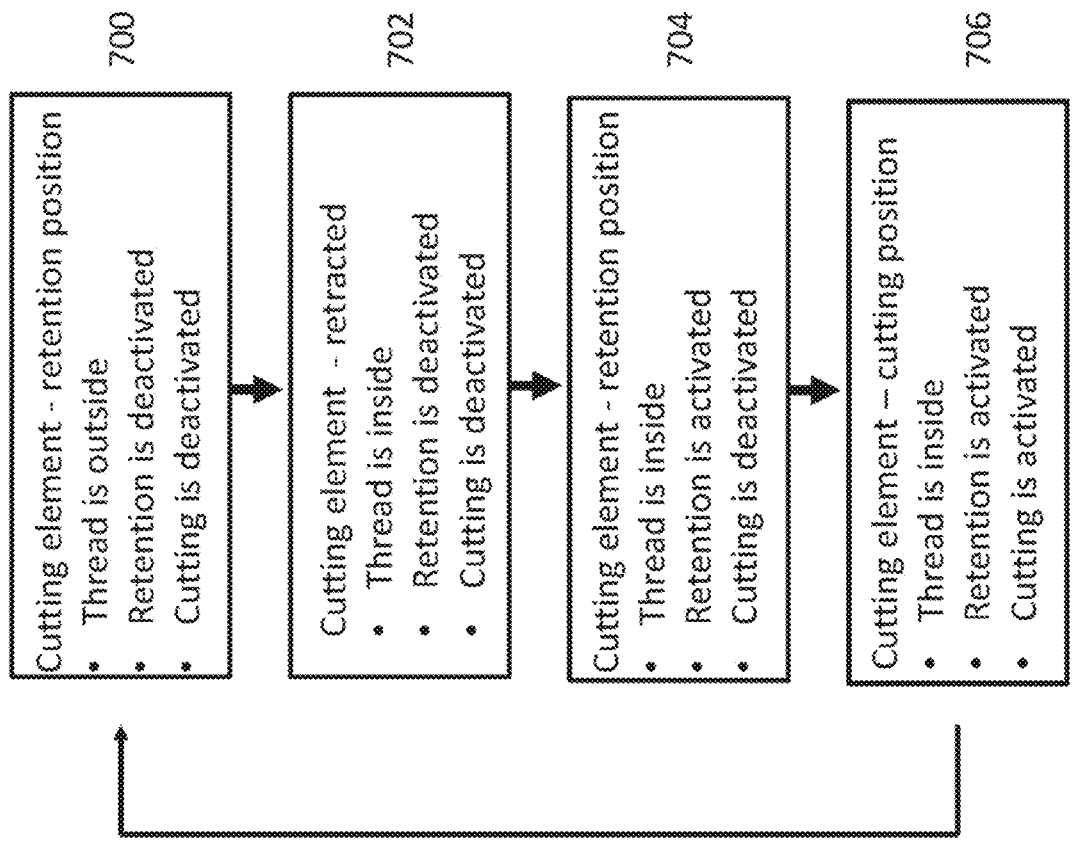
FIG. 35 is a state diagram depicting the different states of the cutting element of the cutting device, according to some embodiments of the invention.

Reference is now made to FIG. 35 depicting the cutting element states, according to some embodiments of the invention.

According to some exemplary embodiments, when a thread is not inserted or loaded into the device, the cutting element is in a pre-insertion state at 700. In some embodiments, in a pre-insertion state, the cutting element is pushed forward towards the distal end of the cutting device. Alternatively, the cutting element is pushed towards the proximal end of the device. In some embodiments, in a pre-insertion state the thread is outside. Additionally, retention and cutting mechanisms are deactivated.

According to some exemplary embodiments, the cutting element is in a retracted state at 702, for example to allow the insertion of a thread into the cutting device. In some embodiments, in a retracted state the thread is inside the cutting device. Additionally, both retention and cutting mechanisms are deactivated.

According to some exemplary embodiments, the cutting element is in a retention state at 704, for example to capture and retain a portion of the thread within the device. In some embodiments, in a retention state the thread is inside the cutting device and the retention mechanism is activated. Additionally, the cutting mechanism is deactivated.

According to some exemplary embodiments, when the cutting element is in a cutting state at 706, the thread is inside the cutting device, and both retention and cutting mechanisms are activated.

It is expected that during the life of a patent maturing from this application many relevant suture thread cutting devices will be developed; the scope of the terms retention and cutting is intended to include all such new technologies a priori.

As used herein with reference to quantity or value, the terms "in approximation" and "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for suture thread cutting, comprising:
   a handle;
   a stationary external element having a groove at the distal end, and a proximal end connected to said handle, said groove being fitted and shaped for holding a suture thread;
   a movable cutter having a cutting edge, and wherein said cutter is operatively connected to said handle to move between a first position and a second position with respect to said external element as a result of manipulation of said handle;
   an aligning element, connected to a distal end of said stationary external element and comprising a U-shaped opening fitted to the distal end of said groove;
   a distal flange on said cutter, said flange having a gap bounded by said cutting edge, and wherein in said first position, the channel is configured to retain the suture thread, and in said second position, the cutting edge and the groove are positioned to cut the suture.

2. The cutting device of claim 1, wherein said gap opens to a U-shaped opening in said flange.

3. The cutting device of claim 1, wherein said gap of said flange is aligned with said opening of said aligning element for insertion of said thread into said channel.

4. The cutting device of claim 1, wherein said cutting edge of said flange is rotated in at least 90° degrees relative to said U-shaped opening of said aligning element when cutter is in a first position to retain said thread.

5. The cutting device of claim 1, wherein said cutting edge of said flange is rotated in at least 180° degrees relative to said U-shaped opening of said aligning element when the cutter is in a second position to cut said thread.

6. The cutting device of claim 5, wherein said cutting edge is configured to apply shear forces on said thread when said flange is rotated in at least 180° degrees relative to said U-shaped opening of said aligning element to cut said thread.

7. The cutting device of claim 6, wherein said cutting edge of said movable cutter moves to a third position, wherein in said third position, said cutting device is configured to receive the suture thread.

8. The cutting device of claim 1, wherein in said first position to retain said thread, said flange is moved towards said aligning element of said stationary external element.

9. The cutting device of claim 1, wherein said groove extends diagonally across said stationary external element.

10. The cutting device of claim 1, wherein said handle further comprises a lever configured to selectively move said cutter to said first position and to said second position upon force exertion on said lever.

11. The cutting device of claim 10, further comprising a locking button operative to retain said cutter in said first position for retaining said thread.

12. The cutting device of claim 11, wherein said locking button is displaced sideway to move said cutter to said second position for cutting said thread.

13. The cutting device of claim 11, wherein said lever further comprises a recess for locking said locking button when said cutter is in said first position for retaining said thread.

14. The device of claim 1, further comprising a bushing connected to said cutter; wherein said movement of said bushing in a proximal direction retracts said cutter to assume a thread insertion state.

* * * * *